(12) United States Patent
Huntsman et al.

(10) Patent No.: US 9,309,323 B2
(45) Date of Patent: Apr. 12, 2016

(54) METHODS FOR DETECTING AND TREATING CANCER

(75) Inventors: David Huntsman, Vancouver (CA); Helen Merkens, Burnaby (CA); Aruna Somasiri, Vancouver (CA); Kelly M. McNagny, Vancouver (CA); Calvin Roskelley, Vancouver (CA)

(73) Assignee: The University of British Columbia, Vancouver (CA)

( * ) Notice: Subject to any disclaimer, the term of this patent is extended or adjusted under 35 U.S.C. 154(b) by 564 days.

(21) Appl. No.: 12/508,849

(22) Filed: Jul. 24, 2009

(65) Prior Publication Data

US 2010/0061978 A1    Mar. 11, 2010

Related U.S. Application Data

(63) Continuation-in-part of application No. 10/560,103, filed as application No. PCT/CA2004/000857 on Jun. 9, 2004, now Pat. No. 7,833,733.

(60) Provisional application No. 60/476,622, filed on Jun. 9, 2003, provisional application No. 60/537,018, filed on Jan. 20, 2004.

(51) Int. Cl.
| | |
|---|---|
| *A61K 39/395* | (2006.01) |
| *G01N 33/574* | (2006.01) |
| *C07K 16/30* | (2006.01) |
| *A61K 31/7105* | (2006.01) |

(52) U.S. Cl.
CPC ......... *C07K 16/3092* (2013.01); *A61K 31/7105* (2013.01)

(58) Field of Classification Search
None
See application file for complete search history.

(56) References Cited

U.S. PATENT DOCUMENTS

| | | | |
|---|---|---|---|
| 5,869,045 | A * | 2/1999 | Hellstrom et al. ......... 424/130.1 |
| 6,395,882 | B1 | 5/2002 | Rosen et al. |
| 6,613,515 | B1 | 9/2003 | Xu et al. |
| 8,828,387 | B2 | 9/2014 | Kajikawa et al. |
| 2004/0002067 | A1 | 1/2004 | Erlander et al. |

FOREIGN PATENT DOCUMENTS

WO    02/079492    10/2002

OTHER PUBLICATIONS

Schopperle, W.M. et al., Human Embryonal Carcinoma Tumor Antigen, Gp200/GCTM-2, is podocalyxin, Biochem. Biophys. Res. Comm., vol. 300, No. 2, Jan. 10, 2003, pp. 285-290.
Fieger, C.B. et al., Endoglycan, A member of the CD34 family, functions as an L-selectin ligand through modification with tyrosine sulfation and sialyl Lewis x., J. Biol. Chem., vol. 278, No. 30, May 16, 2003.
Somasiri, A. et al., Overexpression of the anti-adhesin podocalyxin is an independent predictor of breast cancer progression, Cancer Res., vol. 64, Aug. 1, 2004, pp. 5068-5073.
Tockman, M.S. et al, Considerations in Bringing a Cancer Biomarker to Clinical Application, Cancer Research, vol. 52, May 1, 1992, pp. 2711S-2718S.
Nielsen, J.S and McNagny, K.M., Novel functions of the CD34 family, Journal of Cell Science, vol. 121, No. 22, 2008, pp. 3683-3692.
McNagny, K., "The CD34 Family as Essential Regulations of Adhesion in Development and Disease", (PowerPoint Presentation)—Chicago Symposium, Oct. 23, 2008.
Hsu, Y.H., et al., "Podocalyxin EBP50 Ezrin Molecular Complex Enhances the Metastatic Potential of Renal Cell Carcinoma Through Recruiting Rac1 Guanine Nucleotide Exchange Factor ARHGEF7", The American Journal of Pathology, 2010, pp. 1-12, vol. 176, No. 6.
Tan, H.L. et al., "mAb 84, a cytotoxic antibody that kills undifferentiated human embryonic stem cells via oncosis", Stem Cells, 2009, pp. 1792-1801, vol. 27.
Tornos et al., "Expression of WT1, CA 125, and GCDFP-15 as useful markers in the differential diagnosis of primary ovarian carcinomas versus metastatic breast cancer to the ovary", Am. J. Surg. Pathol., 29(11), pp. 1482-1489, 2005.

* cited by examiner

*Primary Examiner* — Mark Halvorson
(74) *Attorney, Agent, or Firm* — Bereskin & Parr LLP; Melanie Szweras

(57) ABSTRACT

Methods and kits for detecting cancer and monitoring cancer progression are described. The method involves analyzing a sample containing nucleic acids or proteins from a patient for decreased expression of endoglycan and/or increased expression of podocalyxin.

4 Claims, 17 Drawing Sheets

Figure 2
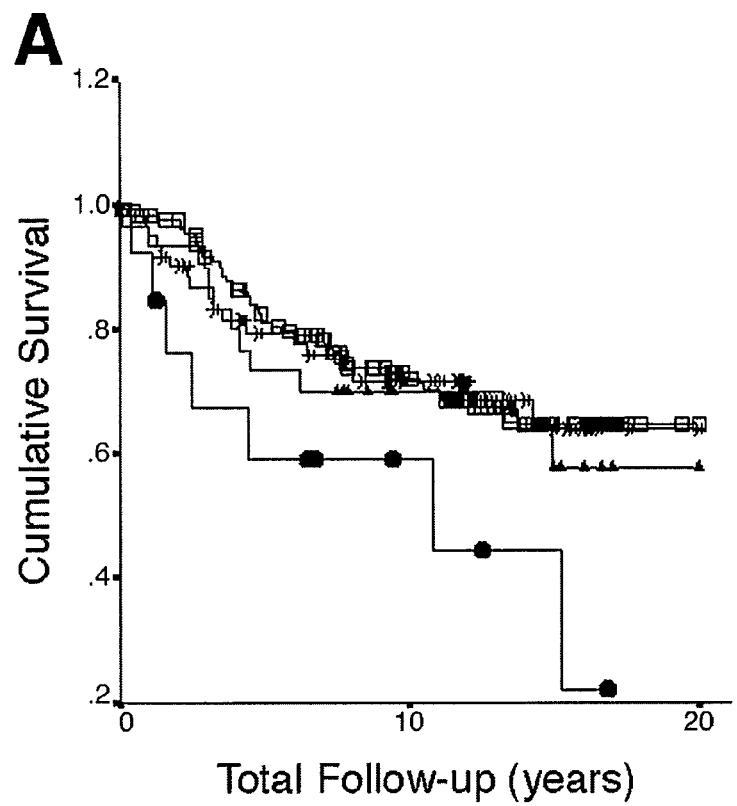
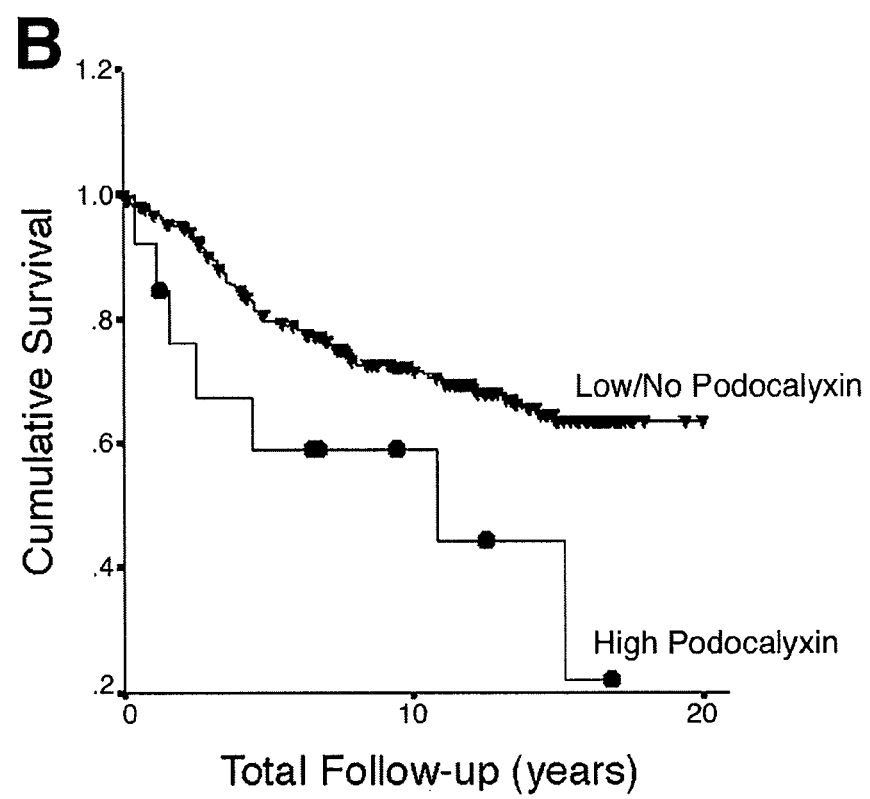

Figure 4: Genomic loci, motifs and splicing
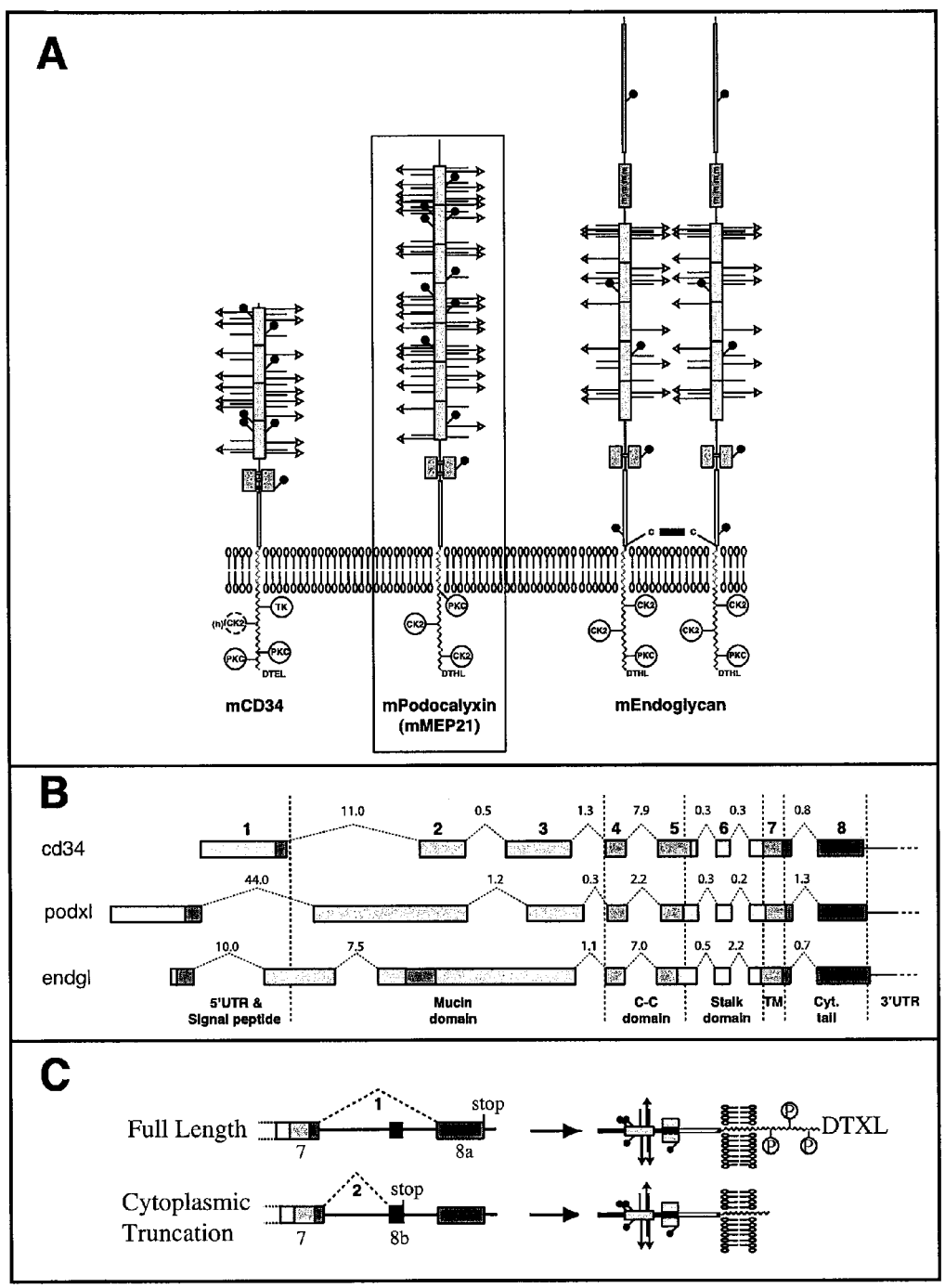

Fig. 5 : homologies

Endoglycan

```
hEndgl  MGRLLRAARLPPLLSPLLLLLVGGAFLGACVAGSDEPGPEGLTSTSLLDLLLPTGLEPLD  60
mEndgl  MARPLRAARLPP---PLLLLLAAGASLGAYAVGVDEPGPEGLTSTSLLDLLLPTDFEPLD  57
        *.* ********   ******..** ***..* *******************.:****

hEndgl  SEEPSETMGLGAGLGAPGSGFPSEENEESRILQPPQYFWEEEEELNDSSLDLGPTADYVF 120
mEndgl  SEEPSEAMGLDAGL-APGSGFPSEDSEESRLLQPPQYFWEEEE-LNGSSLDLGPTADYVF 115
        ****:*.* ****:.:******** .************* hEndgl  PDLTEKAGSIEDTSQAQELPNLPSPLPKMNLVEPPWHMPPREEEEEEEEEEE-REKEEVE 179
mEndgl  PDLTEKVASMEDPGQAPDLPNLPSILPKMDLAEPPWHMPLQEEEEEEEEEEEEREEEERE 175
        ******..*:.. :**** **:*.***** :****** :** * hEndgl  KQEEEEEEE---LLPVNGSQEEAKPQVRDFSLTSSS----QTPGATKSRHEDSGDQASSG 232
mEndgl  KEAEEEEEKGKSLLPVNRVPKEPPAQAHAPSPSTSSSTSSQSPGATRHRQEDSGDQATSG 235
        *: *****:    *****  :*..*.:  *  ::**    *:****: *:*******:**

hEndgl  VEVESSMGPSLLLPSVTPTTVTPGDQDSTSQEAEATVLPAAGLGVEFEAPQEASEEATAG 292
mEndgl  MEVESSVKPTLSVPSVTPSTVAPGVQN-YSQESGGTEWPTGGLGVQSEVPQGAGEGATVG 294
        :*****.*:* :***::** *: ***..*  *:.****: *.** *.* **.* hEndgl  AAGLSGQHEEVPALPSFPQTTAPSGAEHPDEDPLGSRTSASSPLAPGDMELTPSSATLGQ 352
mEndgl  AADFDGQQGALPSS-SLPQTVPPSGTEVPSEGPLYPRIPDSLPPGPQDTESTPSSATWGQ 353
        .:.:  :*: *:*..*:*.*..:** .*  *.*  * * .**** hEndgl  EDLNQQLLEGQAAEAQSRIPWDSTQVICKDWSNLAGKNYIILNMTENIDCEVFRQHRGPQ 412
mEndgl  EGLSEQPLEGQAAEAHSLTPWDSTQVICKDWSNLAGKSYIILNMTENIDCEVFRRHRGLR 413
        *.*.:* ********:*  **********************.**********:*** :

hEndgl  LLALVEEVLPRHGSGHHGAWHISLSKPSEKEQHLLMTLVGEQGVVPTQDVLSMLGDIRRS 472
mEndgl  LLALVEEVLPRHRSGHRGDWHISLSKPSEKEQHLLMTLVGEQGVVPTQDVLSMLSGIRRS 473
        ************ ***:* *********************************..****

hEndgl  LEEIGIQNYSTTSSCQARASQVRSDYGTLFVVLVVIGAICIIIIALGLLYNCWQRRLPKL 532
mEndgl  LEEIGIQNYSTTSSCQARATQVRSDYGTLFVVLVIIGVICFIIIVLGLLYNCWQRRMPKL 533
        *****************:**********:.:*.********:* hEndgl  KHVSHGEELRFVENGCHDNPTLDVASDSQSEMQEKHPSLNGGGALNGPGSWGALMGGKRD 592
mEndgl  KHVSHGEELRFVENGCHDNPTLDVASDSQSEMQEKQPSLNGG-AINGPSSWSALMGSKRD 592
        ********************************:**** *:*..**.* hEndgl  PEDSDVFEEDTHL 605
mEndgl  PEDSDVFEEDTHL 605
        *************
```

| overall % homology: | 76% |
|---|---|
| extracellular % homology: | 72% |
| cytoplasmic % homology: | 92% |

Fig. 5 : homologies          Cont'd

Podocalyxin

```
hPodxl  MRCALALSALLLLLSTPPLLPSSPSPSPSPSPSQNATQTTTDSSNKTAPTPASSVTIMAT  60
mPodxl  MPPTTALSALLLLLLSP----ASHSHNGN-ETSTSAIKSSTVQSHQSATTSTEVTTGHPV  55
        *  : *********.:*      :* * ....* .* :::* .*:::*.*.:. .*  ..

hPodxl  DTAQQSTVPTSKANEILASVKATTLGVSSDSPGTTTLAQQVSGPVNTTVARGGGSGNPTT  120
mPodxl  ASTLASTQPS----------NPTPFTTSTQSP-----SMPTSTPNPTSNQSGGNLTSSVS  100
        ::   ** *:          :.*.: .*::**     : .* * *:   **. ...:

hPodxl  TIESPKSTKSADTTTVATSTATAKPNTTSSQ-NGAEDTTNSGGKSSHSVTTDLTSTKAEH  179
mPodxl  EVDKTKTSSPSSTAFTSSSGQTASSGGKSGDSFTTAPTTTLGLINVSSQPTDLN-TTSKL  159
        ::...*::..:.*:  .::*  **... .*.:   : **. *  . * .***. *.::

hPodxl  LTTPHPTSPLSPRQPTLTHPVATPTSSGHDHLMKISSSS-STVAIPGYTFTSPGMTTTLP  238
mPodxl  LSTPTTDNTTSPQQPVDSSPSTASHPVGQHTPAAVPSSSGSTPSTDNSTLTWK--PTTHK  217
        *:**  .  .. **:**. : * ::. . *:.    :.*** ** :  . *:*    .**

hPodxl  SSVISQRTQQTSSQMPASSTAPSSQETVQPTSPATALRTPTLPETMSSSPTAASTTHRYP  298
mPodxl  PLGTSEATQPLTSQTPGITTLPVS--TLQQSMASTVGTTTEEFTHLISNGTPVAPPG--P  273
        .   *:   : *.:* * *  *:* : ..:*. *.    : *. *..:..   * hPodxl  KTPSPTVAHESNWAKCEDLETQTQSEKQLVLNLTGNTLCAGGASDEK--LISLICRAVKA  356
mPodxl  STPSPIWAFGNYQLNCEPPIRPD--EELLILNLTRASLCERSPLDEKEKLVELLCHSVKA  331
        .****  *. .   :**    *:  *:. *:** :.    ***  *::.*::.*** hPodxl  TFNPAQDKCGIRLASVPGSQTVVVKEITIHTKLPAKDVYERLKDKWDELKEAGVSDMKLG  416
mPodxl  SFKPAEDLCTLHVAPILDNQAVAVKRIIIETKLSPKAVYELLKDRWDDLTEAGVSDMKLG  391
        :*:**:* *  :::*. .: ..*:*.**.*  *.* * ..* ;:*.********** hPodxl  DQGPPEEAEDRFSMPLIITIVCMASFLLLVAALYGCCHQRLSQRKDQQRLTEELQTVENG  476
mPodxl  KEGPPEVNEDRFSLPLIITIVCMASFLLLVAALYGCCHQRISQRKDQQRLTEELQTVENG  451
        .:**  :.********************:******************* hPodxl  YHDNPTLEVMETSSEMQEKKVVSLNGELGDSWIVPLDNLTKDDLDEEEDTHL  528
mPodxl  YHDNPTLEVMETPSEMQEKKVVNLNGELGDSWIVPLDNLTKDDLDEEEDTHL  503
        ************.********.******************************
```

| overall % homology: | 43% |
|---|---|
| extracellular % homology: | 30% |
| cytoplasmic % homology: | 96% |

Fig. 5 : homologies
Cont'd

CD34

```
hCD34  ------------MPRGWTALCLLSLLPSGFMSLDNNGTATPELPTQGTFSNVSTNVSYQE  48
mCD34  MQVHRDTRAGLLLPWRWVALCLMSLLH-----LNNLTSATTETSTQGISPSVPTNESVEE  55
        :*  *.**:*           *:*  :**.* .***  ..*.** * :* hCD34  TTTPSTLGSTSLHPVSQHGNEATTNITETTVKFTSTSVITSVYGNTNSSVQSQTSVISTV  108
mCD34  NITSSIPGSTSHYLIYQDSSKTTPAISETMVNFTVTSGIPSGSGTPHTFSQPQTSPTGIL  115
        . *.*  ****  : :  *...::*.  *:** *:** ** *.*  *..::  *.***  . :

hCD34  FTTPANVSTPETTLKPSLSPGNVSDLSTTSTSLAT-SPTKPYT-SSSPILSDIKAEIKCS  166
mCD34  PTTSDSISTSEMTWKSSLPSINVSDYSPNNSSFEMTSPTEPYAYTSSSAPSAIKGEIKCS  175
        . .:.* * *... ** *...:*:    *:: :**.  * .*** hCD34  GIREVKLTQGICLEQNKTSSCAEFKKDRGEGLARVLCGEEQADADAGAQVCSLLLAQSEV  226
mCD34  GIREVRLAQGICLELSEASSCEEFKKEKGEDLIQILCEKEEAEADAGASVCSLLLAQSEV  235
        *****:*:**** .::* **::.*  :;** :*:*:*** .******** hCD34  RPQCLLLVLANRTEISSKLQLMKKHQSDLKKLGILDFTEQDVASHQSYSQKTLIALVTSG  286
mCD34  RPECLLMVLANSTELPSKLQLMEKHQSDLRKLGIQSFNKQDIGSHQSYSRKTLIALVTSG  295
        :*:** :. ****:** :**  .*.:*: .****:******** hCD34  ALLAVLGITGYFLMNRRSWSPTGERLGEDPYYTENGGGQGYSSGPGTSPEAQGKASVNRG  346
mCD34  VLLAILGTTGYFLMNRRSWSPTGERLGEDPYYTENGGGQGYSSGPGASPETQGKANVTRG  355
        .***:**  *****************************************:***.****.*.**

hCD34  AQKNGTGQATSRNGHSARQHVVADTEL  373
mCD34  AQENGTGQATSRNGHSARQHVVADTEL  382
        **:***********************
```

| overall % homology: | 65% |
|---|---|
| extracellular % homology: | 55% |
| cytoplasmic % homology: | 93% |

Fig. 5 : homologies

Cont'd

```
mPodxl      ------EDRFSLPLIITIVCMASFLLLVAALYGCCHQRISQRKDQQRLTEELQTVENGYH  54
mEndgl      -----RSDYGTLFVVLVIIGVICFIIIVLGLLYNCWQRRMPKLKHVSHGEELRFVENGCH  55
mCD34       KQDIGSHQSYSRKTLIALVTSGVLLAILGTTGYFLMNRRSWSPTGERLGEDPYYTENGGG  60
                 :   ::.::    :: ::          :*            *:   .*** mPodxl      DNPTLEVMETP-SEMQEKKVVNLNGELG--DSWIVPLDNLTKDDLDE----EEDTHL  104
mEndgl      DNPTLDVASDSQSEMQEKQPSLNGGAINGPSSWSALMG--SKRDPEDSDVFEEDTHL  110
mCD34       QGYSSGPGASP--ETQGKANVTRGAQENGTGQATSRNGHSARQHVVA------DTEL  109
            :. :       . * *    .. .  ..     . ::  .       **.*
```

Figure 8 Failure of Endo to inhibit mast cell aggregation

FIGURE 9
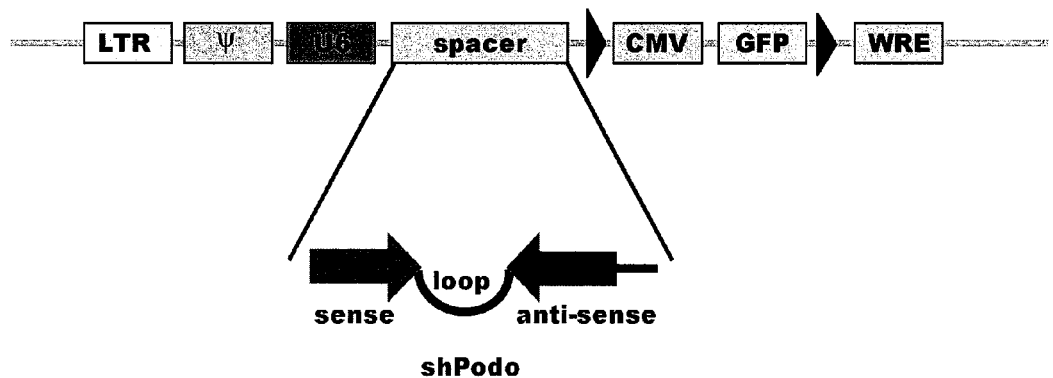
| Sequences | -------- SENSE ---------- LOOP ------- ANTISENSE ------------- |
|---|---|
| shPodoA | 5'-TGAGACTGGCCTATCATTTATTCAAGAGATAAATCATAGGCCAGTCTCTTTTTTC-3' |
| shPodoB | 5'-TGTATTCTTGTGGTATAAGTTTCAAGAGAACTTATACCACAAGAATACTTTTTTC-3' |
| shPodoC | 5'-TGAATGTAAATGTCTATTTATTCAAGAGATAAATAGACATTTACATTCTTTTTTC-3' |
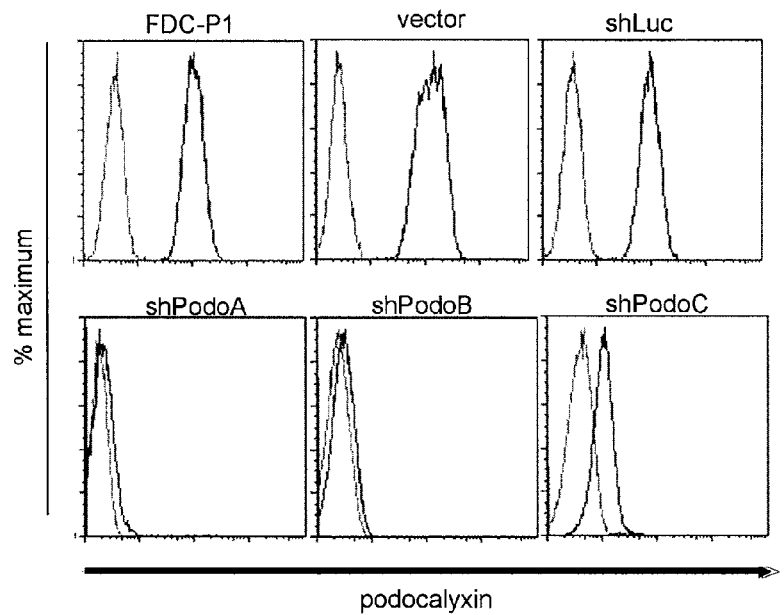

Figure 12
A
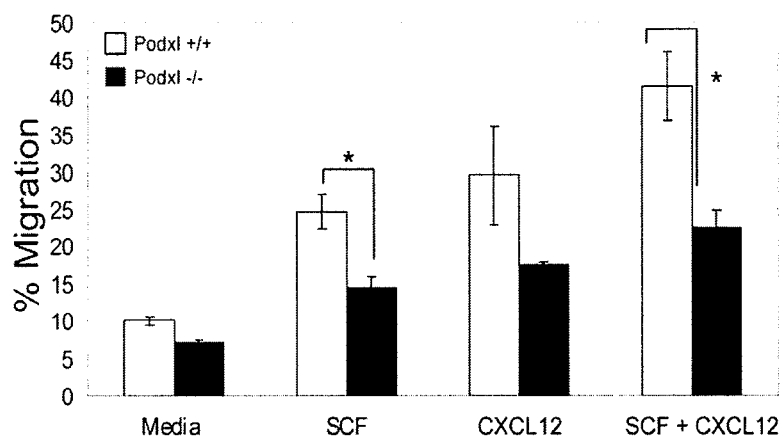
B
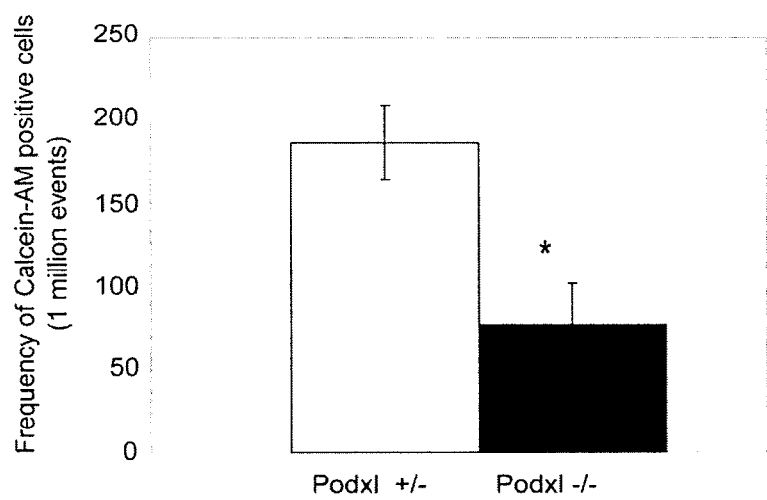

Figure 14
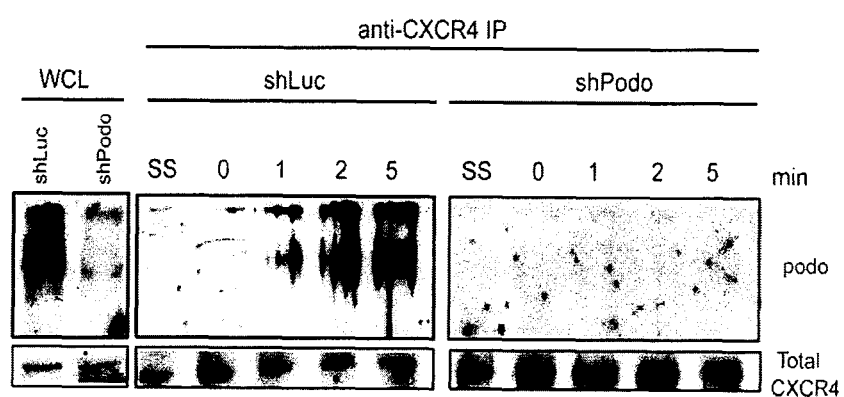
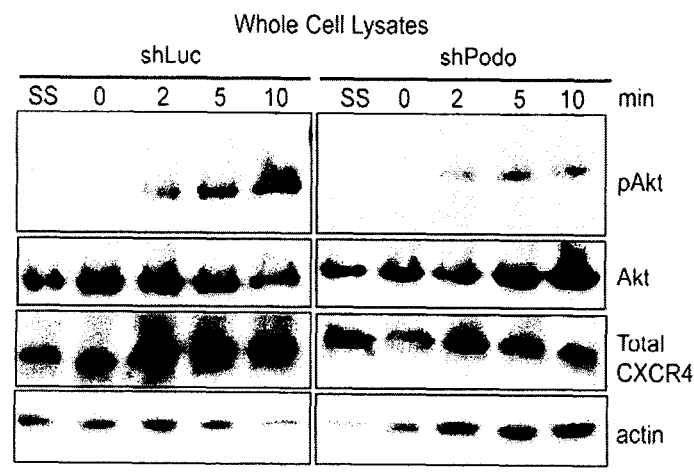

METHODS FOR DETECTING AND TREATING CANCER

This application is a continuation-in-part of U.S. application Ser. No. 10/560,103 filed Dec. 9, 2005 (pending), which is a national phase entry of PCT application No. PCT/CA2004/000857 filed Jun. 9, 2004 which claims the benefit of U.S. Provisional Application Ser. No. 60/537,018 filed Jan. 24, 2004 (now abandoned) and U.S. Provisional Application Ser. No. 60/476,622 filed Jun. 9, 2003 (now abandoned), all of which are incorporated by reference in their entirety.

FIELD OF THE DISCLOSURE

The disclosure relates to methods and kits for detecting and monitoring the progression of cancer, in particular breast cancer. The disclosure also includes methods of treating cancer.

BACKGROUND OF THE DISCLOSURE

Metastatic breast cancer is the leading cause of death among women between the ages of 15 and 54 and affects approximately 13% of women during their lifespan. These can be grossly categorized as ductal or lobular depending on their site of origin in normal breast tissue. Tumors usually begin as non-invasive cells at the site of tumor origin, spread to surrounding tissue in the breast and eventually become fully metastatic and migrate to the lymph nodes and other parts of the body.

There is increasing evidence that cell-cell adhesion is a potent suppressor of metastatic breast cancer progression (Berx and Van Roy, 2001). For example, in infiltrating lobular breast carcinomas E-cadherin is often lost and the resulting disruption of adherens junctions initiates a complete dissolution of cell-cell adhesion which allows single cells to break away from the primary tumor and invade the stroma in a single file pattern (Cleton Jansen et al., 2002). Alterations in cell adhesion are more subtle in infiltrating ductal carcinomas where invasion is characterized by the movement of clusters of cells into the stroma (Page and Simpson, 2000). In the latter situation adherens junctions are often present (Acs et al., 2001; Gillett et al., 2001) but there appears to be a general loss of polarity that is characterized by the mislocalization of apical markers such as MUC-1 (McGuckin et al., 1995; Mommers et al., 1999; Diaz et al., 2001; Rahn et al., 2001) that may be fueled by the disruption of tight junctions (Hoover et al., 1997; Kramer et al., 2000; Kominsky et al., 2003). While transcriptional repressors of E-cadherin expression have been identified (Cano et al., 2000; Guaita et al., 2002), little is known about the mechanism responsible for the disruption of tight junctions during breast tumor progression.

In adult vertebrates, blood homeostasis is maintained by a pool of predominantly quiescent (Cheshier et al., 1999), multipotent hematopoietic stem cells (HSC) and more mature hematopoietic progenitors cells (HPC) that reside in specific microenvironmental niches in the bone marrow (reviewed by Scadden (Scadden, 2006)). These hematopoietic cells have an intrinsic homing mechanism to facilitate their retention and maintenance in this microenvironment (Whetton and Graham, 1999). Furthermore, when appropriately triggered to mobilize to the circulation (perhaps by host injury), HSC/P homing allows these cells to re-localize to the appropriate niche once blood homeostasis has been restored (Nervi et al., 2006). In the clinic, this homing property is exploited in everexpanding hematopoietic stem cell transplant (HSCT) (Thomas et al., 1957) treatment modalities for leukemia and lymphoma (Mehta and Davies, 2008; Shenoy and Smith, 2008; Sierra et al., 2008; Stein and Forman, 2008; Tse et al., 2008), autoimmune disorders (Alderuccio et al., 2006), inherited immunodeficiency and metabolic disorders (Dvorak and Cowan, 2008; Prasad and Kurtzberg, 2008), hemaglobinopathies (Pinto and Roberts, 2008; Ullah et al., 2008) and various forms of bone marrow failure (Barrett and Savani, 2008; Gluckman and Wagner, 2008; Perez-Albuerne et al., 2008). Successful treatment relies on the long-term engraftment of the donor HSCs, which, in turn, demands a faithful execution of a complex progression of cell movements including: vascular adhesion, diapedesis, migration towards a chemokine gradient and then adhesion and stable lodgment of donor HSC to the niche (Hart et al., 2004; Kaplan et al., 2007).

The processes of homing and engraftment are directed and influenced by a variety of constituents (reviewed by Laird, von Andrian and Wagers (Laird et al., 2008) and Kaplan, Psaila and Lyden (Kaplan et al., 2007)) some of these include: cell-cell and cell-matrix adhesion molecules and their ligands, soluble and cell-bound chemoattractants and survival factors, proteases, extracellular matrix components and extracellular calcium ion (Ca2+) (Adams et al., 2006). When in the bone marrow circulation, HSCs initiate tethering and rolling via interaction with selectins and subsequently sense a chemotactic gradient that, when combined with additional cell-adhesion signals, lead to diapedesis through the bone marrow vasculature followed by directional chemotaxis to reach the niche (Papayannopoulou and Craddock, 1997; Williams et al., 1991). This α4-integrin mediated migration is well coordinated in a way that permits cells to adhere and yet also to remain mobile and migratory. Accordingly, equilibrium is established between activated and non-activated integrins at the cell surface in order to propel the cell forward during this migration.

CXCL12 (formerly known as stromal-derived factor or SDF-1α) is a vital chemoattractant in HSC/P homing that is produced by cells of the bone marrow stroma—a term describing a heterogeneous component of the bone marrow niche (Cheshier et al., 1999). Alone or in concert with other factors, CXCL12 has pleiotropic effects on HSC/Ps including modulation of motility, regulation of HSC homing to and retention within the bone marrow niche, promotion of survival (Broxmeyer, 2008; Lee et al., 2002); and, stimulation of proliferation (Aiuti et al., 1997; Aiuti et al., 1999). CXCL12 exerts is effects via CXCR4, a seven-pass transmembrane G protein-coupled receptor (GPCR) that is expressed by diverse immature and mature blood cells (Broxmeyer, 2008; Tavor et al., 2004; Weissman, 1996). In addition to playing a role in the normal trafficking of a variety of blood cell types, CXCR4 has also been shown to play an important role in tumor cell metastasis (Burger and Kipps, 2006; Burger and Burkle, 2007; Hartmann et al., 2005). There is considerable evidence that the CXCR4-CXCL12 axis is central to maintaining the HSC pool in the marrow niche. For example, inducible deletion of CXCR4 in adult mice causes HSC depletion and increased sensitivity to 5-fluorouracil (Sugiyama et al., 2006) and small molecule CXCR4-specific agonists, CXCL12-mimetic peptides (recently reviewed by Pelus and Fukuda (Pelus and Fukuda, 2008)), antibodies to CXCR4, and, inhibitors of CXCL12 proteolytic activation (Campbell and Broxmeyer, 2008) can all induce mobilization of hematopoietic precursor cells to the peripheral blood or block homing to the bone marrow.

Another factor produced by stromal cells of the bone marrow niche is stem-cell factor (SCF), an essential factor in hematopoiesis that binds and activates the receptor tyrosine kinase c-Kit (Blechman et al., 1993; Blechman and Yarden, 1995; Broudy, 1997). Expressed as either a secreted soluble factor or a membrane-bound factor, SCF not only aids in the homing and maintenance of HSCs (Driessen et al., 2003) within the niche, but also the survival and proliferation of HSCs (Hart et al., 2004). Since SCF and CXCL12 exert both distinct and overlapping effects on hematopoietic cells and share many of the same intracellular signaling pathways to mediate their effects, they work together to enhance HSC cell motility, proliferation and survival (Cancelas et al., 2006; Glodek et al., 2007; Kapur et al., 2001; Williams et al., 2008).

CD34 was initially identified over 20 years ago as an hematopoietic stem cell and vascular endothelial marker and has alternatively been proposed to act as an: 1) enhancer of proliferation, 2) a blocker of differentiation, 3) bone marrow homing receptor, 4) cell adhesion molecule, and 5) a blocker of cell adhesion (Fackler et al, 1996, Krause et al. Blood, 1996, Baumhueter et al. 1993). The CD34 antigen has long been used as a marker to identify and enrich donor-derived HSC with long-term repopulating potential in clinical applications of HSCT. CD34 is the founding member of a family of related HSC sialomucins including podocalyxin and endoglycan (Furness and McNagny, 2006) (Nielsen JS and McNagny J Cell Sci. 2008 Nov. 15; 121(Pt 22):3683-92). In mice, CD34 is expressed by a subset of mature blood cells and immature progenitors as well as all vascular endothelia including specialized endothelial cells (termed high endothelial venules or HEV) in lymph nodes. CD34 gene knockout mice are relatively normal with very subtle defects in hematopoietic and vascular function. The function of CD34 has been widely debated, but the current data suggest that it (and its relatives) can either promote (Baumheter et al., 1993; Hiraoka et al., 1999; Puri et al., 1995; Sassetti et al., 1998b) or obstruct cell-cell adhesion interactions (Blanchet et al., 2007; Drew et al., 2002; Drew et al., 2005) depending on the context and tissue type (reviewed in Nielsen and McNagny, J Cell Sci. 2008 Nov. 15; 121(Pt 22):3683-92). The most clear-cut experiments suggest that CD34-type proteins can act as either pro-adhesive or anti-adhesive molecules depending on their glycosylation status (Satomaa, 2002, Baumhueter et al., 1993 and Bistrup et al., 1999).

Additional evidence for an anti-adhesive function for this family of molecules comes from mutational analysis of CD34's closest relative, podocalyxin. Podocalyxin, which was named for its prominent expression on kidney podocytes (Dekan et al., 1991; Horvat et al., 1986; Kerjaschki et al., 1984) is also expressed by HSCs and all vasculature.

Podocalyxin, (also called podocalyxin-like protein 1 (PCLP-1), Myb-Ets-transformed progenitor (MEP21) or thrombomucin) is a heavily sialylated and sulfated integral membrane glycoprotein that interacts with the actin cytoskeleton. It belongs to the CD34 family of sialomucins and is highly expressed on the surface of hematopoeitic progenitors, vascular endothelia and podocytes which form a tight junction-free epithelial meshwork that surrounds glomerular capillaries in the kidney (Kerjaschki et al., 1984; Kershaw et al., 1995; McNagny et al., 1997). Evidence suggests that the primary function of this molecule is to act as a type of molecular "Teflon™" to block inappropriate cell adhesion. For example, as kidney podocytes begin to express podocalyxin they undergo a dramatic morphological shift from adherent, tight junction-associated monolayers surrounding the glomerular capillaries to a more modified cell layer lacking tight junctions and with extensive fully-interdigitated foot processes that are separated from each other by slit diaphragms. These podocalyxin-covered slit diaphragms form the primary filtration apparatus of the kidney. Deletion of the podocalyxin-encoding gene in mice results in the persistence of tight-junctions between podocytes, a lack of foot process formation and perinatal death due to anuria and high blood pressure (Doyonnas et al., 2001). In this context, podocalyxin acts as an anti-adhesive to facilitate the dissolution of cell-cell junctions and drive the formation of the extensive podocyte foot processes required for renal filtration (Doyonnas et al., 2001). Conversely, when podocalyxin is ectopically expressed in kidney epithelial cell monolayers, tight junctions and adherens junctions are both disrupted (Takeda et al., 2000). In this context, podocalyxin decreases cell-cell adhesion by expanding the apical cell domain and marginalizing junctional complexes between cells in monolayers (Takeda et al., 2000). Thus, both gain-of-function and loss-of-function experiments suggest that podocalyxin acts as a tissue-specific anti-adhesin during normal kidney development (Takeda et al., 2001, Doyonnas et al., 2001).

Circumstantial evidence suggests that podocalyxin expression may be upregulated in a variety of neoplastic scenarios. For example podocalyxin was recently identified as the peanut agglutinin-binding tumor antigen gp200 expressed on human embryonal carcinomas. (Schopperle et al., 2002). In addition, the human podocalyxin gene (PODXL) has been assigned to chromosome 7q32-q33 (Kershaw et al., 1997), which places PODXL very close to the 7q35ter region that has been identified as a gain site by comparative genomic hybridization in ductal carcinoma in situ, infiltrating ductal carcinoma and in lymph node metastasis (Aubele et al., 2000). Thus, while it is not yet clear whether the PODXL gene is amplified in breast carcinoma, its expression may be unduly influenced by a nearby amplicon. Under anemic conditions the inventors have recently shown that Podocalyxin expression is upregulated in mouse erythroid progenitor cells (McNagny submitted unpublished obs). Therefore, podocalyxin expression may be similarly upregulated in necrotic breast carcinomas where hypoxia-regulated genes are transcriptionally activated (Adeyinka et al., 2002). If this is indeed the case, it would have functionally important implications as tumor hypoxia helps to drive solid tumor progression generally (Knowles and Harris, 2001) and ductal carcinoma progression specifically (Bos et al., 2003; Helczynska et al., 2003). Up-regulated podocalyxin expression has been found to mark the most invasive human epithelial tumours of prostate and breast (Casey et al., 2006; Sizemore et al., 2007; Somasiri et al., 2004).

Podocalyxin expression has been detected on a limited set of non-cancerous hematopoietic cells in adult mammals including activated platelets (Miettinen et al., 1999), anemia-induced stress reticulocytes and erythroblasts (Doyonnas et al., 2005; Sathyanarayana et al., 2007), and, importantly, on a subset of primitive bone marrow resident hematopoietic progenitors with long-term repopulating capacity (Doyonnas et al., 2005). Despite its limited expression in mammalian adult hematopoietic tissue, podocalyxin is highly-expressed on the surface of definitive hematopoietic cells derived from the fetal liver of E15.5 mouse embryos (Doyonnas et al., 2005). This expression is first detected in hematopoietic progenitors and primitive erythroid progenitors of the yolk sac and is maintained on multi-potential blood progenitors and multi-lineage hematopoietic cells of embryonic fetal liver. Podocalyxin expression declines dramatically before birth and then is expressed again at high levels for a brief window as adult hematopoiesis is established in the marrow (Doyonnas et al., 2005).

The present inventors have previously hypothesized that podocalyxin behaves as a regulator of cell adhesion during hematopoietic cell migration or hematopoietic stem/progenitor cell engraftment since its expression correlates with the ontogenetical migration and engraftment of HSCs in developing mouse embryos (Doyonnas et al., 2005), and, because it is expressed on a subset of lineage-sca-1+c-kit+ (LSK) cells with enhanced long-term HSC-repopulating potential (Doyonnas et al., 2005).

Using homologies present in the cytoplasmic tails of CD34 and podocalyxin, endoglycan was identified as a novel member of this family of glycoproteins. Endoglycan mRNA and protein were detected in both endothelial cells and CD34+ bone marrow cells (Sassetti et al., 2000). Endoglycan, like CD34 and podocalyxin can function as a L-selectin ligand. Endoglycan utilizes a different binding mechanism, interacting with L-selectin through sulfation on two tyrosine residues and O-linked sLex structures (Fieger et al., 2003).

SUMMARY OF THE DISCLOSURE

The inventors have shown that podocalyxin is a prognostic indicator of tumor metastasis and that it plays an active role in making cells less adherent and more invasive. The present inventors have also shown that endoglycan is an antagonist of podocalyxin.

Accordingly, in one embodiment, the present disclosure provides a method for detecting cancer in a patient comprising:

(a) determining the level of podocalyxin in a sample from the patient; and (b) comparing the level of podocalyxin in the sample to a control, wherein increased levels of podocalyxin as compared to the control indicates that the patient has cancer.

In another embodiment, the present disclosure provides a method for detecting cancer in a patient comprising:

(a) determining the level of endoglycan in a sample from the patient; and (b) comparing the level of endoglycan in the sample to a control, wherein decreased levels of endoglycan as compared to the control indicates that the patient has cancer.

In a further embodiment, the present disclosure provides a method for detecting cancer in a patient comprising:

(a) determining the level of endoglycan and podocalyxin in a sample from the patient; and (b) comparing the ratio of endoglycan to podocalyxin in the sample to a control, wherein a decreased ratio of endoglycan to podocalyxin as compared to the control indicates that the patient has cancer.

In yet another embodiment, the present disclosure provides a method for monitoring the progression of cancer in a patient, comprising:

(a) determining the level of podocalyxin in a sample from the patient; and (b) repeating step (a) at a later point in time and comparing the result of step (a) with the result of step (b) wherein a difference in the level of podocalyxin expression is indicative of the progression of the cancer in the patient.

In another embodiment, the present disclosure provides a method for monitoring the progression of cancer in a patient, comprising:

(a) determining the level of endoglycan in a sample from the patient; and (b) repeating step (a) at a later point in time and comparing the result of step (a) with the result of step (b) wherein a difference in the level of endoglycan expression is indicative of the progression of the cancer in the patient.

In a further embodiment, the present disclosure provides a method for monitoring the progression of cancer in a patient comprising:

(a) determining the level of endoglycan and podocalyxin in a sample from the patient; and (b) repeating step (a) at a later point in time and comparing the result of step (a) with the result of step (b) wherein a difference in the ratio of endoglycan to podocalyxin is indicative of the progression of the cancer in the patient.

In another embodiment, the present disclosure provides a method for determining whether or not a cancer is metastatic in a patient comprising:

(a) detecting the level of podocalyxin in a sample from the patient; and (b) comparing the level of podocalyxin in the sample to a control, wherein increased levels of podocalyxin as compared to the control indicates that the cancer is metastatic.

In yet another embodiment, the present disclosure provides a method for determining whether or not a cancer is metastatic in a patient comprising:

(a) detecting the level of endoglycan in a sample from the patient; and (b) comparing the level of endoglycan in the sample to a control, wherein decreased levels of endoglycan as compared to the control indicates that the cancer is metastatic.

In a further embodiment, the present disclosure provides a method for determining whether or not a cancer is metastatic in a patient comprising:

(a) detecting the level of endoglycan and podocalyxin in a sample from the patient; and (b) comparing the ratio of endoglycan to podocalyxin in the sample to a control, wherein a decreased ratio of endoglycan to podocalyxin as compared to the control indicates that the cancer is metastatic.

In an embodiment of the disclosure, the above methods are used to detect breast cancer, ovarian cancer, prostate cancer, hepatocellular cancer, hematologic malignancies, lung metastasis, osteosarcoma, melanoma, vaculogenic gliomas or glioblastoma. In one embodiment, the methods are used to detect breast cancer.

The present disclosure includes methods of treating cancer by modulating, optionally inhibiting, the levels of podocalyxin and/or CXCR4 on the cancer. The application also includes methods for the identification of compounds that modulate the biological activity of podocalyxin and/or CXCR4 that may be used for the treatment of cancers with increased expression of podocalyxin.

The present disclosure includes methods of treating cancer by modulating, optionally agonizing, the levels of endoglycan on the cancer. The application also includes methods for the identification of compounds that modulate the biological activity of endoglycan that may be used for the treatment of cancers with decreased expression of endoglycan.

Accordingly, the present disclosure provides a method of modulating cancer cell growth by administering an effective amount of an agent that modulates endoglycan and/or podocalyxin to a cell or animal in need thereof.

The present disclosure also includes screening assays for identifying agents that modulate endoglycan and/or podocalyxin and that are useful in modulating cancer cell growth. Agents that modulate include agents that stimulate (agonists) and agents that inhibit (antagonists).

Accordingly, the present disclosure provides a method for identifying a compound that modulates podocalyxin comprising:

(a) incubating a test compound with podocalyxin or a nucleic acid encoding podocalyxin; and (b) determining the effect of the compound on podocalyxin activity or expression and comparing with a control (i.e. in the absence of the test substance), wherein a change in the podocalyxin activity or expression as compared to the control indicates that the test compound modulates podocalyxin.

In another embodiment, the present disclosure provides a method for identifying a compound that modulates endoglycan comprising:

(a) incubating a test compound with endoglycan or a nucleic acid encoding endoglycan; and (b) determining the effect of the compound on endoglycan activity or expression and comparing with a control (i.e. in the absence of the test substance), wherein a change in the endoglycan activity or expression as compared to the control indicates that the test compound modulates endoglycan.

The present disclosure includes pharmaceutical compositions containing one or more modulators of endoglycan and/or podocalyxin. Accordingly, the present disclosure provides a pharmaceutical composition for use in modulating cancer cell growth comprising an effective amount of endoglycan/podocalyxin modulator in admixture with a suitable diluent or carrier.

In one embodiment, the present disclosure provides a pharmaceutical composition for use in treating cancer comprising an effective amount of a podocalyxin antagonist in admixture with a suitable diluent or carrier. In another embodiment, the present disclosure provides a pharmaceutical composition for use in treating cancer comprising an effective amount of an endoglycan agonist in admixture with a suitable diluent or carrier.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 2 consists of two graphs illustrating the prognostic significance of podocalyxin expression in breast tumors (Kaplan-Meier survival analysis). Disease specific survival at all expression levels indicates that only the high podocalyxin expression level (+3) is prognostically significant (A). Therefore, expression levels 0 to 2 were combined as "no or low podocalyxin" and +3 as was designated as "high podocalyxin" (B).

FIG. 3A shows the endogenous levels in three human breast carcinoma lines as assessed by Western blotting with an antibody specific for human podocalyxin. Note that podocalyxin was modestly expressed in well-behaved T47D and MCF-7 cells compared to the highly invasive MDA231 cell line.

FIG. 3B is a series of photographs showing MCF-7 cells that were control transfected or stably transfected with an expression vector containing both GFP and mouse podocalyxin. Control transfected MCF-7 cells formed classical cobblestone epithelial monolayers (top panel) while bulging cells were shed from the surface of the GFP/Podocalyxin transfected cells (middle panel). GFP (green) and mouse podocalyxin (red) were coordinately expressed in a heterogenous manner (lower panel). (upper two panels live phase microscopy, bar=50 µm; lower panel, Z-series confocal dual fluorescence microscopy for GFP and mouse-specific podocalyxin immunostaining; bar=15 µm).

FIG. 3C is a series of photographs of transfected MCF-7 cells that were triple stained for mouse podocalyxin (red), DNA/Nuclei (blue) and either the adherens junction protein E-cadherin or the tight junction protein occludin (green). Note that where podocalyxin was not expressed E-cadherin was localized basolaterally and occludin was localized at apical terminal bars. In contrast, where podocalyxin was expressed the cells bulged apically (note upward movement of blue nuclei) and both E-cadherin and occludin localization became depolarized (Z-series confocal microscopy, bar=15 µm)

FIG. 4 shows the CD34 family including their genomic loci, motifs and splicing. (A) Schematic showing the hypothetical structure of CD34, Podocalyxin, and Endoglycan based on predicted protein sequences and published data. Blue boxes=mucin domains, green boxes=the cysteine-rich domains, black circles=potential N-linked carbohydrates, horizontal bars with or without arrows=potential O-linked carbohydrates, arrows=potential sialic acid motifs on O-linked carbohydrates, PKC, CK2 and TK=potential phosphorylation sites. (B) Genomic organization of human cd34, podxl and endgl genes based on sequence contigs identified in the human sequence database. (C) Alternative splicing of CD34-family transcripts and their consequences for protein structure. Analyses of ESTs, primary cDNA clones and genomic loci suggest that, for all three family members, splicing between exons 7 and 8 results in longer cDNAs with premature translational stops that lead to truncation of the cytoplasmic domains.

FIG. 5 shows homologies between CD34 family orthologs and homologs (SEQ ID NOs:1-9).

FIG. 9 shows knock-down of podocalyxin expression in FDC-P1 cells. (A) Schematic of lentiviral construct used to silence podocalyxin expression. Abbreviations are as follows: LTR, long-terminal repeat; ψ, HIV packaging signal; U6, promoter; CMV, cytomegalovirus promoter; GFP, green fluorescent protein; WRE, woodchuck hepatitis virus response element. Three sequences designed to suppress podocalyxin expression are shown (shPodoA, B and C (SEQ ID NOs: 11-13, respectively)). (B) Flow cytometry analysis of podocalyxin expression (podocalyxin (blue) and isotype controls (red)). (C) Confocal microscope images (X-Y sections) of anti-podocalyxin labelled FDCP-1 infected with shLuc, shPodoA, shPodoB or empty lentiviral vectors. Bar is 10 μm. Sample labels for (B) and (C) are as follows: vector (lentiviral plasmid); shLuc (luciferase-suppressing sequence); shPodoA, B and C (podocalyxin knock-down target sequences).

FIG. 12 shows podocalyxin enhances migration of primary E15.5 fetal liver cells towards SCF+CXCL12 in vitro and short term homing to bone marrow in vivo. A) The ex vivo migration of Ter119-depleted FTL cells across fibronectin-coated transwells to media alone, or media with SCF, CXCL12 or SCF+CXCL12. Podxl$^{-/-}$ (open bars) and Podxl$^{+/+}$ controls (solid bars). Results are expressed as the % of total cells added to the upper chamber that cross into the lower chamber after 6 hrs. B) Calcein AM-labelled Ter119-depleted E15.5 FTL cells ($1\times10^6$) were injected into the tail vein of normal congeneic (C57Bl/6) recipients. Shown is the number of cells recovered from the bone marrow (2 femora) of recipient mice 3 hrs after injection. The frequency of Calcein AM positive cells were determined by flow cytometry and expressed as a frequency of $1\times10^6$ events. *Statistically significant difference; $p<0.05$.

FIG. 14 shows podocalyxin co-precipitates with CXCR4 and enhances Akt phosphorylation. FDCP-1 cells expressing shLuc or podocalyxin-knock down vector (shPodo) were deprived of IL-3 and then restimulated (or not) with a pre-mixed cocktail of SCF+CXCL12 for the indicated times. Results from FDC-P1 cells maintained in IL-3 culture media (SS, steady-state) are also shown. (A) Immunoblot of CXCR4 immunoprecipitates from starved and then restimulated (1-5 mins) as indicated. Whole cell lysates (WCL) prepared from non-stimulated FDC-P1 were fractionated in parallel as a control for immunoblotting. Membranes are probed with anti-podocalyxin (upper panel) and anti-CXCR4 (lower panel). (B) Immunoblots of WCL showing the level of phospho-Akt (S473) (upper panel), total cell Akt and CXCR4 (middle panels), and, total actin as a loading control (lower panel).

DETAILED DESCRIPTION OF THE DISCLOSURE

I. Diagnostic Methods

Figure 1:
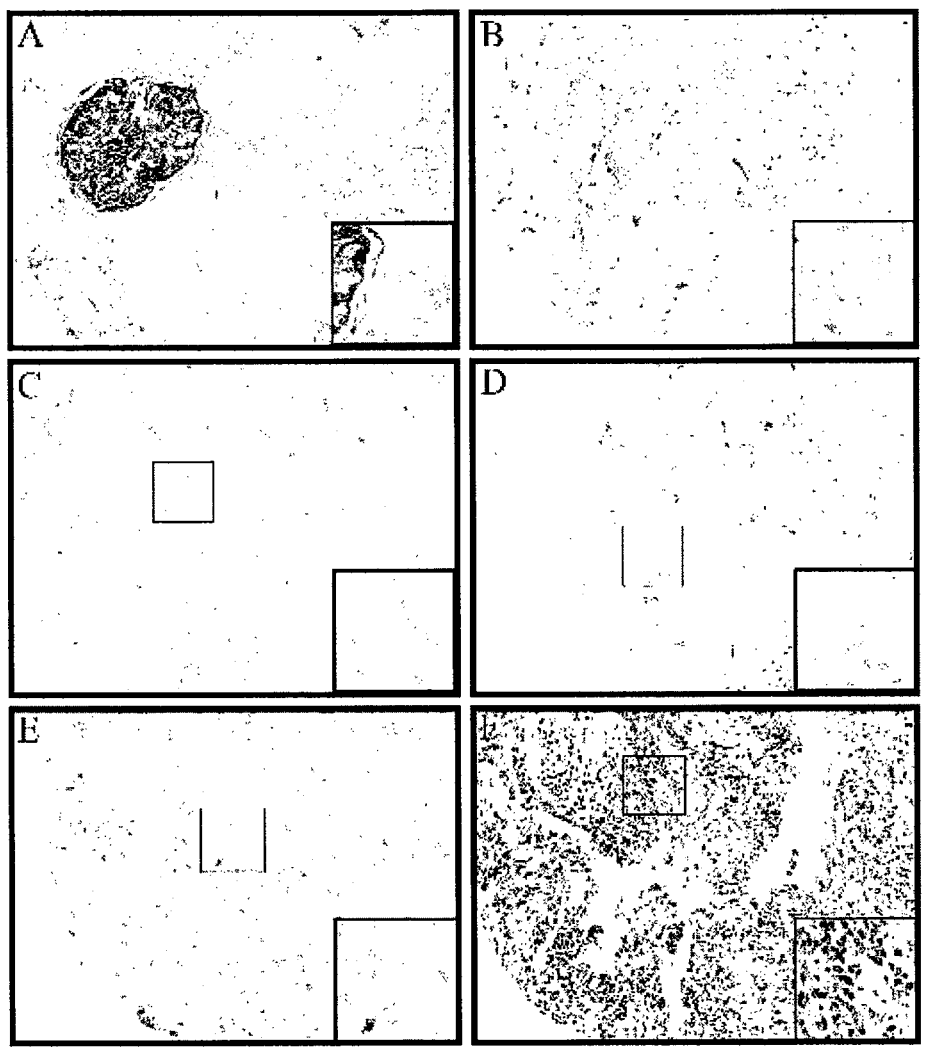
FIG. 1 shows podocalyxin immunostaining of normal tissues and the tumor microarray. In positive control kidney tissue (A) the podocytes within the glomerulus were highly positive while the tubular epithelium was negative (see inset). The vascular endothelium of the glomerulus and within the kidney cortex was also positive. In normal breast tissue (B) positive staining was observed in the vascular endothelium (arrows) and the apical regions of luminal breast epithelial cells (see inset; arrowheads). On the tissue microarray invasive breast carcinomas were scored as: '0' (ie. C) if there was no discernable staining on the carcinoma cells (see inset; positive staining is on endothelial cells); '1' (ie. D) if less than 10% of the cells stained positively; '2' (ie. E) if there was diffuse staining in more than 10% of the cells and/or strong cytoplasmic staining in less than 50% of the cells; or '3' if there was strong cytoplasmic staining in more than 50% of the cells (ie. F).

The present inventors have determined that podocalyxin is a functionally important molecule in tumor progression. Using a tissue microrray (TMA), the inventors assessed podocalyxin expression and localization in a series of 270 invasive human breast carcinomas for which full clinicopathologic follow up and outcome was present. Podocalyxin was found to be highly expressed and diffusely distributed in a small subset of these tumors. It was also found that high podocalyxin expression was a clear and independent prognostic indicator of poor outcome in this tumor subset. To test the functional consequences of this increased expression, murine podocalyxin was ectopically expressed in human MCF-7 breast carcinoma cells that normally grow as adherent monolayers with abundant adherens junctions and tight junctions. Low level ectopic podocalyxin expression lead to the disruption of both adherens and tight junctions while high cells expressing high levels of the protein were de-polarized and actively extruded from otherwise cohesive MCF-7 monolayers. The data demonstrates that podocalyxin is a prognostic indicator of tumor metastasis and that it plays an active role in making cells less adherent and more invasive. The inventors have also shown that podocalyxin is involved in decreasing the apical/basal cell polarity of breast tissues, a hallmark of solid tumor progression. The inventors have also shown that podocalyxin expression is dramatically increased during hypoxia, as the rapid proliferation of cells during tumor progression causes the tissue to become hypoxic. Therefore, podocalyxin is a marker of solid tumor progression and a marker of tumor hypoxia.

The present inventors have also determined that endoglycan and podocalyxin have a mirror image pattern of expression in breast cancer cells lines. Endoglycan levels are high in the relatively non-metastatic lines MCF-7 and T47D where podocalyxin levels are low. In contrast, endoglycan expression is negative in the MDA-231 metastatic tumor line compared to high levels of podocalyxin. Since endoglycan and podocalyxin have similar sequences in the cytoplasmic domain, endoglycan may be a natural antagonist of podocalyxin. Endoglycan may promote adhesion, maintain cell polarity and block metastasis whereas podocalyxin may block adhesion, decrease polarity and increase metastasis. Despite endoglycan's similarity to CD34 and podocalyxin (FIGS. 4 and 5), it does not block cell aggregation when ectopically expressed in CD34/CD43 deficient mast cells, a phenotype of ectopic expression of CD34. Podocalyxin is known to bind to the actin cytoskeleton through binding to NHERF (Li and Kershaw 2002, and Takeda 2001). Since endoglycan binds NHERF but lacks an anti-adhesive function, it may act as an antagonist of podocalyxin by competing with podocalyxin's ability to interact with the actin cytoskeleton and more specifically with NHERF.

Accordingly, evaluating endoglycan and/or podocalyxin levels may be used in the prognostic and diagnostic evaluation of cancers involving endoglycan and/or podocalyxin, the identification of subjects with a predisposition to such cancers, and in the monitoring of the progress of patients with endoglycan related cancers.

In an embodiment, a method is provided for detecting cancer in a patient comprising:

(a) detecting the level of podocalyxin in a sample from the patient; and (b) comparing the level of podocalyxin in the sample to a control, wherein increased levels of podocalyxin as compared to the control indicates that the patient has cancer.

In another embodiment, a method is provided for detecting cancer in a patient comprising:

(a) detecting the level of endoglycan in a sample from the patient; and (b) comparing the level of endoglycan in the sample to a control, wherein decreased levels of endoglycan as compared to the control indicates that the patient has cancer.

Evaluating endoglycan levels relative to podocalyxin levels may also be used in the prognostic and diagnostic evaluation of cancers involving endoglycan, the identification of subjects with a predisposition to such cancers, and in the monitoring of the progress of patients with endoglycan related cancers.

Accordingly, in another embodiment, a method is provided for detecting cancer in a patient comprising:

(a) determining the level of endoglycan and podocalyxin in a sample from the patient; and (b) comparing the ratio of endoglycan to podocalyxin in the sample to a control, wherein a decreased ratio as compared to control indicates that the patient has cancer.

The term "podocalyxin" as used herein is synonymous with podocalyxin-like protein 1 (PCLP-1), Myb-Ets-transformed progenitor (MEP21) or thrombomucin and is a heavily sialyated and sulfated integral membrane glycoprotein that interacts with the actin cytoskeleton. The term podocalyxin includes all of the known podocalyxin molecules including those deposited in GenBank under accession number U97519 or those referred to in Kershaw et al. (Kershaw D B, Beck S G, Wharram B L, Wiggins J E, Goyal M, Thomas P E, Wiggins R C., Molecular cloning and characterization of human podocalyxin-like protein. Orthologous relationship to rabbit PCLP1 and rat podocalyxin. J Biol Chem. 1997 Jun. 20; 272(25):15708-14) as well as any isoforms, variants, analogs, derivatives or fragments thereof that are useful in detecting cancer.

The term "endoglycan" includes all of the known endoglycan molecules including those deposited in GenBank under accession number AF219137 or those referred to in Sassetti et al. (Sassetti C, Van Zante A, and S D Rosen, (2000) Identification of Endoglycan, a Member of the CD34/Podocalyxin Family of Sialomucins, Journal of Biological Chemistry, 275 (12):9001) as well as any isoforms, variants, analogs, derivatives or fragments thereof that are useful in detecting cancer.

The phrase "detecting the level of endoglycan" and "detecting the level of podocalyxin" includes the detection of the levels of protein as well as detection of the levels of nucleic acid molecules encoding the protein. Methods for detecting proteins and nucleic acids are discussed in greater detail below.

Endoglycan and podocalyxin are alternatively spliced to give two isoforms of the protein core; one with a long cytoplasmic tail and one with a short cytoplasmic tail. Consequently, in a specific embodiment, the methods of the disclosure are used to detect the short form of endoglycan and/or podocalyxin.

The term "cancer" as used herein includes all cancers that are associated with decreased expression of endoglycan and/or increased expression of podocalyxin. In one embodiment, the cancer is breast cancer, optionally invasive breast carcinoma. In another embodiment, the cancer is breast cancer, ovarian cancer, prostate cancer, hepatocellular cancer, hematologic malignancies, lung metastasis, osteosarcoma, melanoma, vaculogenic gliomas or glioblastoma. In another embodiment, the cancer is teratoma inducing cells.

The term "sample from a patient" as used herein means any sample containing cancer cells that one wishes to detect including, but not limited to, biological fluids, tissue extracts, freshly harvested cells, and lysates of cells which have been incubated in cell cultures. In one embodiment, the sample is breast tissue.

The term "control" includes any predetermined value or sample that can be used to establish a base or normal level. The predetermined value may be established by testing control samples and establishing a known value that is found in healthy persons. In such an embodiment, use of a control sample is not required for each test. A control sample may include tissue samples taken from healthy persons or samples mimicking physiological fluid.

The method of the disclosure may be used in the diagnosis and staging of cancer, in particular breast cancer. The method may also be used to monitor the progression of a cancer and to monitor whether a particular treatment is effective or not. In particular, the method can be used to confirm the absence or removal of all tumor tissue following surgery, cancer chemotherapy, and/or radiation therapy. The methods can further be used to monitor cancer chemotherapy and tumor reappearance.

In an embodiment, the disclosure contemplates a method for monitoring the progression of cancer in a patient, comprising:

(a) determining the level of podocalyxin expression in a sample from the patient; and (b) repeating step (a) at a later point in time and comparing the result of step (a) with the result of step (b) wherein a difference in the level of podocalyxin expression is indicative of the progression of the cancer in the patient.

In particular, increased levels of podocalyxin at the later time point may indicate that the cancer is progressing and that the treatment (if applicable) is not being effective. In contrast, decreased levels of podocalyxin at the later time point may indicate that the cancer is regressing and that the treatment (if applicable) is effective.

In another embodiment, the disclosure contemplates a method for monitoring the progression of cancer in a patient, comprising:

(a) determining the level of endoglycan expression in a sample from the patient; and (b) repeating step (a) at a later point in time and comparing the result of step (a) with the result of step (b) wherein a difference in the level of endoglycan expression is indicative of the progression of the cancer in the patient.

In particular, decreased levels of endoglycan at the later time point may indicate that the cancer is progressing and that the treatment (if applicable) is not being effective. In contrast, increased levels of endoglycan at the later time point may indicate that the cancer is regressing and that the treatment (if applicable) is effective.

In a further embodiment, the disclosure contemplates a method for monitoring the progression of cancer in a patient, comprising:

(a) determining the level of endoglycan and podocalyxin in a sample from the patient; and (b) repeating step (a) at a later point in time and comparing the result of step (a) with the result of step (b) wherein a difference in the ratio of endoglycan to podocalyxin is indicative of the progression of the cancer in the patient.

The inventors have also shown that endoglycan and/or podocalyxin is a marker of tumor metastasis. Accordingly, the present disclosure provides a method of determining whether or not a cancer is metastatic in a patient comprising:

(a) detecting the level of podocalyxin in a sample from the patient; and (b) comparing the level of podocalyxin in the sample to a control, wherein increased levels of podocalyxin as compared to the control indicates that the cancer is metastatic.

In another embodiment, the present disclosure provides a method of determining whether or not a cancer is metastatic in a patient comprising:

(a) detecting the level of endoglycan in a sample from the patient; and (b) comparing the level of endoglycan in the sample to a control, wherein decreased levels of endoglycan as compared to the control indicates that the cancer is metastatic.

In a further embodiment, the present disclosure provides a method of determining whether or not a cancer is metastatic in a patient comprising:

(a) detecting the level of endoglycan and podocalyxin in a sample from the patient; and (b) comparing the ratio of endoglycan to podocalyxin in the sample to a control, wherein a decreased ratio of endoglycan to podocalyxin as compared to the control indicates that the cancer is metastatic.

A variety of methods can be employed for the above-described diagnostic and prognostic evaluation of cancers involving endoglycan and/or podocalyxin, and the identification of subjects with a predisposition to such disorders. Such methods may rely on, for example, the detection of nucleic acid molecules encoding endoglycan and/or podocalyxin, and fragments thereof, or the detection of the endoglycan protein and/or podocalyxin protein using, for example, antibodies directed against endoglycan and/or podocalyxin, including peptide fragments. Each of these is described below.

(a) Methods for Detecting Nucleic Acid Molecules

In one embodiment, the methods of the disclosure involve the detection of nucleic acid molecules encoding endoglycan and/or podocalyxin. Those skilled in the art can construct nucleotide probes for use in the detection of nucleic acid sequences encoding endoglycan and/or podocalyxin in samples. Suitable probes include nucleic acid molecules based on nucleic acid sequences encoding at least 5 sequential amino acids from regions of endoglycan and/or podocalyxin, optionally they comprise 15 to 30 nucleotides. A nucleotide probe may be labeled with a detectable substance such as a radioactive label which provides for an adequate signal and has sufficient half-life such as $^{32}$P, $^{3}$H, $^{14}$C or the like. Other detectable substances which may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect genes, optionally in human cells, that encode endoglycan and/or podocalyxin. The nucleotide probes may also be useful in the diagnosis of disorders involving an endoglycan and/or a podocalyxin in monitoring the progression of such disorders; or monitoring a therapeutic treatment. In an embodiment, the probes are used in the diagnosis of, and in monitoring the progression of cancer, optionally breast cancer.

The probe may be used in hybridization techniques to detect genes that encode endoglycan and/or podocalyxin proteins. The technique generally involves contacting and incubating nucleic acids (e.g. recombinant DNA molecules, cloned genes) obtained from a sample from a patient or other cellular source with a probe under conditions favorable for the specific annealing of the probes to complementary sequences in the nucleic acids. After incubation, the non-annealed nucleic acids are removed, and the presence of nucleic acids that have hybridized to the probe if any are detected.

The detection of nucleic acid molecules may involve the amplification of specific gene sequences using an amplification method such as polymerase chain reaction (PCR), followed by the analysis of the amplified molecules using techniques known to those skilled in the art. Suitable primers can be routinely designed by one of skill in the art.

Hybridization and amplification techniques described herein may be used to assay qualitative and quantitative aspects of expression of genes encoding endoglycan and/or podocalyxin. For example, RNA may be isolated from a cell type or tissue known to express a gene encoding endoglycan and/or podocalyxin, and tested utilizing the hybridization (e.g. standard Northern analyses) or PCR techniques referred to herein. The techniques may be used to detect differences in transcript size which may be due to normal or abnormal alternative splicing. The techniques may be used to detect quantitative differences between levels of full length and/or alternatively splice transcripts detected in normal individuals relative to those individuals exhibiting symptoms of a cancer involving an endoglycan and/or podocalyxin protein or gene.

The primers and probes may be used in the above described methods in situ i.e. directly on tissue sections (fixed and/or frozen) of patient tissue obtained from biopsies or resections.

Accordingly, the present disclosure provides a method of detecting cancer in a patient comprising:

(a) extracting nucleic acid molecules comprising the podocalyxin gene or portion thereof from a sample from the patient;

(b) amplifying the extracted nucleic acid molecules using the polymerase chain reaction;

(c) determining the presence of nucleic acid molecules encoding podocalyxin; and (d) comparing the level of podocalyxin in the sample to a control, wherein increased levels of podocalyxin as compared to the control indicates that the patient has cancer.

In another embodiment, the present disclosure provides a method of detecting cancer in a patient comprising:

(a) extracting nucleic acid molecules comprising the endoglycan gene or portion thereof from a sample from the patient;

(b) amplifying the extracted nucleic acid molecules using the polymerase chain reaction;

(c) determining the presence of nucleic acid molecules encoding endoglycan; and (d) comparing the level of endoglycan in the sample to a control, wherein decreased levels of endoglycan as compared to the control indicates that the patient has cancer.

In a further embodiment, the present disclosure provides a method of detecting cancer in a patient comprising:

(a) extracting nucleic acid molecules comprising the endoglycan gene or portion thereof from the sample and the podocalyxin gene or portion thereof from a sample from the patient;

(b) amplifying the extracted nucleic acid molecules using the polymerase chain reaction;

(c) determining the presence of nucleic acid molecules encoding endoglycan and podocalyxin; and (d) comparing the ratio of endoglycan to podocalyxin in the sample to a control, wherein a decreased ratio of endoglycan to podocalyxin as compared to the control indicates that the patient has cancer.

(b) Methods for Detecting Proteins

In another embodiment, the methods of the disclosure involve the detection of the endoglycan and/or podocalyxin protein. In one embodiment, the endoglycan protein is detected using antibodies that specifically bind to endoglycan and/or the podocalyxin protein is detected using antibodies that specifically bind to podocalyxin.

Antibodies to the endoglycan and/or podocalyxin may also be prepared using techniques known in the art. For example, by using a peptide of an endoglycan or podocalyxin, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the protein or peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated.

The inventors have created a monoclonal antibody to endoglycan (Example 2). Accordingly, in another embodiment, the endoglycan protein is detected using a monoclonal antibody raised against a peptide having the sequence V A S M E D P G Q A P D L P N L P S I L P K M D L A E P P W H M P L Q G C (SEQ ID NO:10) that specifically binds to endoglycan.

The term "specifically binds to endoglycan" means reactivity against endoglycan is clearly distinguishable from any reactivity against CD34 or podocalyxin.

The term "specifically binds to podocalyxin" means reactivity against podocalyxin is clearly distinguishable from any reactivity against CD34 or endoglycan.

The term "antibody" as used herein is intended to include fragments thereof which also specifically react with an endoglycan or fragments thereof or a podocalyxin or fragments thereof. Antibodies can be fragmented using conventional techniques and the fragments screened for utility in the same manner as described above. For example, F(ab')$_2$ fragments can be generated by treating antibody with pepsin. The resulting F(ab')$_2$ fragment can be treated to reduce disulfide bridges to produce Fab' fragments.

Chimeric antibody derivatives, i.e., antibody molecules that combine a non-human animal variable region and a human constant region are also contemplated within the scope of the disclosure. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of endoglycan/podocalyxin antigens of the disclosure (See, for example, Morrison et al., Proc. Natl. Acad. Sci. U.S.A. 81, 6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with a protein of the disclosure as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, such as, but not limited to, single-chain Fv monoclonal antibodies reactive against endoglycan or podocalyxin may also be generated by screening expression libraries encoding immunoglobulin genes, or portions thereof, expressed in bacteria with peptides produced from the nucleic acid molecules of endoglycan. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)). Alternatively, a SCID-hu mouse, for example the model developed by Genpharm, can be used to produce antibodies or fragments thereof.

Antibodies specifically reactive with endoglycan and/or podocalyxin, or derivatives, such as enzyme conjugates or labeled derivatives, may be used to detect endoglycan and/or podocalyxin in various samples (e.g. biological materials). They may be used as diagnostic or prognostic reagents and they may be used to detect abnormalities in the level of protein expression, or abnormalities in the structure, and/or temporal, tissue, cellular, or subcellular location of an endoglycan and/or podocalyxin. In vitro immunoassays may also be used to assess or monitor the efficacy of particular therapies. The antibodies of the disclosure may also be used in vitro to determine the level of expression of a gene encoding endoglycan and/or podocalyxin in cells genetically engineered to produce an endoglycan and/or podocalyxin protein.

The antibodies may be used in any known immunoassays which rely on the binding interaction between an antigenic determinant of endoglycan and/or podocalyxin and the antibodies. Examples of such assays are radioimmunoassays, enzyme immunoassays (e.g. ELISA), immunofluorescence, immunoprecipitation, latex agglutination, hemagglutination, and histochemical tests. The antibodies may be used to detect and quantify endoglycan and/or podocalyxin in a sample in order to determine its role in cancer and to diagnose the cancer.

In particular, the antibodies of the disclosure may be used in immuno-histochemical analyses, for example, at the cellular and sub-subcellular level, to detect an endoglycan protein and/or a podocalyxin protein, to localize it to particular cells and tissues, and to specific subcellular locations, and to quantitate the level of expression.

Cytochemical techniques known in the art for localizing antigens using light and electron microscopy may be used to detect endoglycan and/or podocalyxin. Generally, an antibody of the disclosure may be labeled with a detectable substance and an endoglycan and/or podocalyxin protein may be localised in tissues and cells based upon the presence of the detectable substance. Examples of detectable substances include, but are not limited to, the following: radioisotopes (e.g., $^3H$, $^{14}C$, $^{35}S$, $^{125}I$, $^{131}I$), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

The antibody or sample may be immobilized on a carrier or solid support which is capable of immobilizing cells, antibodies etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against endoglycan and/or podocalyxin protein. By way of example, if the antibody having specificity against endoglycan protein is a rabbit IgG antibody, the second antibody may be goat anti-rabbit gammaglobulin labeled with a detectable substance as described herein.

Where a radioactive label is used as a detectable substance, endoglycan and/or podocalyxin may be localized by radioautography. The results of radioautography may be quantitated by determining the density of particles in the radioautographs by various optical methods, or by counting the grains.

Labeled antibodies against endoglycan and/or podocalyxin protein may be used in locating tumor tissue in patients undergoing surgery i.e. in imaging. Typically for in vivo applications, antibodies are labeled with radioactive labels (e.g. iodine-123, iodine-125, iodine-131, gallium-67, technetium-99, and indium-111). Labeled antibody preparations may be administered to a patient intravenously in an appropriate carrier at a time several hours to four days before the tissue is imaged. During this period unbound fractions are cleared from the patient and the only remaining antibodies are those associated with tumor tissue. The presence of the isotope is detected using a suitable gamma camera. The labeled tissue can be correlated with known markers on the patient's body to pinpoint the location of the tumor for the surgeon.

Accordingly, in another embodiment the present disclosure provides a method for detecting cancer in a patient comprising:

(a) contacting a sample from the patient with an antibody that binds to podocalyxin;

(b) detecting the level of podocalyxin in a sample from the patient; and (c) comparing the level of podocalyxin in the sample to a control, wherein increased levels of podocalyxin as compared to the control indicates that the patient has cancer.

In another embodiment the present disclosure provides a method for detecting cancer in a patient comprising:

(a) contacting a sample from the patient with an antibody that binds to endoglycan;

(b) detecting the level of endoglycan in a sample from the patient; and (c) comparing the level of endoglycan in the sample to a control, wherein decreased levels of endoglycan as compared to the control indicates that the patient has cancer.

In a further embodiment, the present disclosure provides a method for detecting cancer in a patient comprising:

(a) contacting a sample from the patient with a first antibody that binds to endoglycan and a second antibody that binds to podocalyxin;

(b) detecting the level of endoglycan and podocalyxin in the sample; and (c) comparing the ratio of endoglycan to podocalyxin in the sample to a control, wherein a decreased ratio of endoglycan to podocalyxin as compared to the control indicates that the patient has cancer.

In a specific embodiment, breast tissue samples can be screened using an anti-endoglycan antibody, such as the monoclonal antibody of Example 2 and/or an anti-podocalyxin antibody. Antibody binding is detected using an appropriate detection system, optionally the Envision detection system, and staining is scored based on the intensity of cellular staining and the proportion of cells stained. Tissue samples are designated "0" (strong endoglycan staining in the majority of tumor cells, and/or no discernable podocalyxin staining), "1" (a mixture of weak and intense membrane staining for endoglycan and/or podocalyxin), "2" (weak endoglycan, and/or strong podocalyxin, staining in the majority of tumor cells) or "3" (no discernable endoglycan staining, and/or high podocalyxin staining). Tissue samples exhibiting no discernable endoglycan staining in the majority of tumor cells and/or high podocalyxin staining (designated "3") have a significantly poorer outcome when compared with the other three designations.

II. Kits

The methods described herein may be performed by utilizing pre-packaged diagnostic kits comprising the necessary reagents to perform any of the methods of the disclosure. For example, the kits may include at least one specific nucleic acid or antibody described herein, which may be conveniently used, e.g., in clinical settings, to screen and diagnose patients and to screen and identify those individuals exhibiting a predisposition to developing cancer. The kits may also include nucleic acid primers for amplifying nucleic acids encoding endoglycan and/or podocalyxin in the polymerase chain reaction. The kits can also include nucleotides, enzymes and buffers useful in the method of the disclosure as well as electrophoretic markers such as a 200 bp ladder. The kit will also include detailed instructions for carrying out the methods of the disclosure.

III. Therapeutic Methods

The finding by the present inventors that endoglycan and podocalyxin are involved in tumor progression allows the development of therapies to treat cancer including the identification of compounds that modulate endoglycan and/or podocalyxin. The present disclosure includes methods of treating cancer by modulating, optionally activating or stimulating, the levels of endoglycan on the cancer and/or optionally suppressing or inhibiting the levels of podocalyxin. The application also includes methods for the identification of compounds that modulate the biological activity of endoglycan and/or podocalyxin that may be used for the treatment of cancers with decreased expression of endoglycan and/or increased expression of podocalyxin.

Accordingly, the present disclosure provides a method of modulating cancer cell growth by administering an effective amount of an agent that modulates endoglycan and/or podocalyxin to a cell or animal in need thereof. The present disclosure also provides a use of an agent that modulates endoglycan and/or podocalyxin to modulate cancer cell growth. The present disclosure further provides a use of an agent that modulates endoglycan and/or podocalyxin in the manufacture of a medicament to modulate cancer cell growth.

The terms "endoglycan", "podocalyxin" and "cancer" as used herein are as defined above in Section I.

The phrase "agent that modulates podocalyxin" includes any agent that can stimulate or activate podocalyxin (i.e. podocalyxin agonists) as well as any agent that can inhibit or suppress podocalyxin (i.e. podocalyxin antagonists). Specific examples of podocalyxin modulators are given below.

The phrase "agent that modulates endoglycan" includes any agent that can stimulate or activate endoglycan (i.e. endoglycan agonists) as well as any agent that can inhibit or suppress endoglycan (i.e. endoglycan antagonists). Specific examples of endoglycan modulators are given below.

The phrase "modulate cancer cell growth" as used herein refers to the inhibition or suppression as well as the activation or stimulation of the formation, differentiation, growth or development of cancer cells.

The phrase "effective amount" as used herein means an amount effective, at dosages and for periods of time necessary to achieve the desired results (e.g. the modulation of cancer cell growth). Effective amounts of a molecule may vary according to factors such as the disease state, age, sex, weight of the animal. Dosage regima may be adjusted to provide the optimum therapeutic response. For example, several divided doses may be administered daily or the dose may be proportionally reduced as indicated by the exigencies of the therapeutic situation.

The term "animal" as used herein includes all members of the animal kingdom which express endoglycan and/or podocalyxin, optionally humans.

The term "a cell" includes a single cell as well as a plurality or population of cells. Administering an agent to a cell includes both in vitro and in vivo administrations.

In one aspect, the present disclosure provides a method of inhibiting cancer cell growth or treating cancer comprising administering an effective amount of podocalyxin antagonist to a cell or animal in need thereof. The disclosure also provides a use of an effective amount of podocalyxin antagonist to inhibit cancer cell growth or treat cancer. The disclosure further provides a use of an effective amount of podocalyxin antagonist in the manufacture of a medicament to inhibit cancer cell growth or treat cancer.

In another aspect, the present disclosure provides a method of inhibiting cancer cell growth or treating cancer comprising administering an effective amount of endoglycan agonist to a cell or animal in need thereof. The disclosure also provides a use of an effective amount of endoglycan agonist to inhibit cancer cell growth or treat cancer. The disclosure further provides a use of an effective amount of endoglycan agonist in the manufacture of a medicament to inhibit cancer cell growth or treat cancer.

The phrase "inhibiting cancer cell growth" means that the growth of the cancer cell is decreased or reduced as compared to the growth of the cancer cell in the absence of the endoglycan agonist and/or podocalyxin antagonist.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treating" can also mean prolonging survival as compared to expected survival if not receiving treatment.

The phrase "podocalyxin antagonist" means any agent that can inhibit or reduce the activity, function or levels of expression of podocalyxin on a cancer cell. Examples of podocalyxin antagonists include, but are not limited to, an antibody, shRNA, small molecule, peptide mimetic, an antisense oligonucleotide to podocalyxin or any molecule or protein that can crosslink podocalyxin on the surface of the tumor cell or can block the interaction between or the colocalization of podocalyxin and CXCR4.

The term "CXCR4" as used herein refers to chemokine (C-X-C) receptor 4, which is also known as fusin and includes all of the known CXCR4 molecules from any species or source, optionally human, including without limitation those deposited in GenBank under accession number BT006660.1 and AY242129.1 as well as any isoforms, variants, analogs, derivatives or fragments thereof that are useful in detecting cancer.

It was reported in 2004 (Balkwill, Semin Cancer Biol. 2004 June; 14(3):171-9) that CXCR4 is expressed in 23 types of cancers. Accordingly, in one embodiment, the therapeutic methods of the disclosure are used to prevent or treat metastasis. In another embodiment, the therapeutic methods of the disclosure are used to treat breast cancer, ovarian cancer, prostate cancer, hepatocellular cancer, hematologic malignancies, lung metastasis, osteosarcoma, melanoma, vaculogenic gliomas or glioblastoma. In one embodiment, the therapeutic methods of the disclosure are used to treat breast cancer. In another embodiment, the therapeutic methods of the disclosure are used to treat teratoma inducing cells.

In one embodiment, the podocalyxin antagonist is a small molecule that binds to podocalyxin. Accordingly, the present disclosure provides a method of treating cancer comprising administering an effective amount of an antagonist that can bind podocalyxin to a cell or animal in need thereof. In yet another embodiment, the podocalyxin antagonist is a small molecule that inhibits the interaction between or colocalization of CXCR4 to podocalyxin. Accordingly, the present disclosure provides a method of treating cancer comprising administering an effective amount of an antagonist that inhibits the colocalization of podocalyxin to CXCR4.

In another embodiment, the podocalyxin antagonist is an antibody that binds podocalyxin and/or CXCR4. The preparation of antibodies to podocalyxin are described above in Section I and the same procedures can be used to prepare antibodies with therapeutic efficacy to podocalyxin or CXCR4. In one embodiment, the antibody will selectively bind a tumor specific isoform of podocalyxin but not the isoform found on normal cells. In yet another embodiment, the podocalyxin antagonist is a monoclonal antibody. Accordingly, the present disclosure provides a method of treating cancer comprising administering an effective amount of an antibody that can bind podocalyxin and/or CXCR4 to a cell or animal in need thereof. The disclosure also provides a use of an effective amount of podocalyxin and/or CXCR4 antibody to inhibit cancer cell growth or treat cancer. The disclosure further provides a use of an effective amount of podocalyxin and/or CXCR4 antibody in the manufacture of a medicament to inhibit cancer cell growth or treat cancer. Coating cancer cells with anti-podocalyxin and/or CXCR4 antibodies may inhibit cell growth or induce apoptosis. In specific embodiments, the antibody could be coupled to a toxin that can cause the death of the cancer cell.

In another embodiment, the podocalyxin antagonist is an antisense oligonucleotide that can modulate the expression and/or activity of podocalyxin and/or CXCR4 on cancer cells.

The term "antisense oligonucleotide" as used herein means a nucleotide sequence that is complimentary to its target.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the disclosure may be joined to form a chimeric oligonucleotide.

In yet another embodiment, the podocalyxin antagonist is a small hairpin or short hairpin RNA or shRNA. The term "shRNA" as used herein refers to a sequence of RNA that forms a tight hairpin turn that can silence gene expression by interfering with RNA. The shRNA is cleaved by cellular machinery into siRNA, which is then bound to the RNA-induced silencing complex. This complex then binds to and cleaves mRNAs which match the siRNA bound to it. In one embodiment, the nucleotide sequence coding podocalyxin shRNA comprises the sequence as shown in SEQ ID NOs: 11-13. These sequences correspond to nucleotides at approximately 2564, 3244, 4446 in the podocalyxin 3'UTR. The 3'UTR appears to be the best place to make shRNA vectors for inhibiting expression. In another embodiment, the podocalyxin antagonist is siRNA.

The phrase "endoglycan agonist" means any agent that can activate or stimulate the activity, function or levels of expression of endoglycan on a cancer cell. Examples of endoglycan agonists include, but are not limited to, an antibody, small molecule, peptide mimetic, a nucleic acid encoding endoglycan or fragment thereof, or any molecule or protein that can antagonize podocalyxin on the surface of the tumor cell.

In one embodiment, the endoglycan agonist is a small molecule that binds to endoglycan. Accordingly, the present disclosure provides a method of treating cancer comprising administering an effective amount of an agonist that can bind endoglycan to a cell or animal in need thereof.

The nucleic acids of the present disclosure (for example, podocalyxin antisense oligonucleotides and nucleic acids encoding endoglycan and fragments thereof) may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other nucleic acids of the disclosure may contain modified phosphorous, oxygen heteroatoms in the phosphate backbone, short chain alkyl or cycloalkyl intersugar linkages or short chain heteroatomic or heterocyclic intersugar linkages. For example, the nucleic acid may contain phosphorothioates, phosphotriesters, methyl phosphonates, and phosphorodithioates. In an embodiment there are phosphorothioate bonds links between the four to six 3'-terminus bases. In another embodiment phosphorothioate bonds link all the nucleotides.

The nucleic acid of the disclosure may also comprise nucleotide analogs that may be better suited as therapeutic or experimental reagents. An example of a nucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acids may contain nucleotides containing polymer backbones, cyclic backbones, or acyclic backbones. For example, the nucleotides may have morpholino backbone structures (U.S. Pat. No. 5,034,506). Nucleic acids may also contain groups such as reporter groups, a group for improving the pharmacokinetic properties of a nucleic acid, or a group for improving the pharmacodynamic properties of a nucleic acid. Nucleic acids may also have sugar mimetics.

The nucleic acids may be constructed using chemical synthesis and enzymatic ligation reactions using procedures known in the art. The nucleic acids of the disclosure or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The sequences may be produced biologically using an expression vector introduced into cells in the form of a recombinant plasmid, phagemid or attenuated virus in which sequences are produced under the control of a high efficiency regulatory region, the activity of which may be determined by the cell type into which the vector is introduced.

The nucleic acids may be introduced into tissues or cells using techniques in the art including vectors (retroviral vectors, adenoviral vectors and DNA virus vectors) or physical techniques such as microinjection. The nucleic acids may be directly administered in vivo or may be used to transfect cells in vitro which are then administered in vivo. In one embodiment, the nucleic acids may be delivered to macrophages and/or endothelial cells in a liposome formulation.

Peptide mimetics of endoglycan and/or podocalyxin may also be prepared as endoglycan modulators or agonists and/or podocalyxin modulators or antagonists. Such peptides may include competitive inhibitors, enhancers, peptide mimetics, and the like. All of these peptides as well as molecules substantially homologous, complementary or otherwise functionally or structurally equivalent to these peptides may be used for purposes of the present disclosure.

"Peptide mimetics" are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of a peptide, or enhancer or inhibitor of the disclosure. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to an endoglycan peptide of the disclosure.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Peptides derived from endoglycan isoforms and/or podocalyxin isoforms may also be used to identify lead compounds for drug development. The structure of the peptides described herein can be readily determined by a number of methods such as NMR and X-ray crystallography. A comparison of the structures of peptides similar in sequence, but differing in the biological activities they elicit in target molecules can provide information about the structure-activity relationship of the target. Information obtained from the examination of structure-activity relationships can be used to design either modified peptides, or other small molecules or lead compounds that can be tested for predicted properties as related to the target molecule. The activity of the lead compounds can be evaluated using assays similar to those described herein.

Information about structure-activity relationships may also be obtained from co-crystallization studies. In these studies, a peptide with a desired activity is crystallized in association with a target molecule, and the X-ray structure of the complex is determined. The structure can then be compared to the structure of the target molecule in its native state, and information from such a comparison may be used to design compounds expected to possess the desired activity. Accordingly, in one embodiment, endoglycan may be cocrystallized with podocalyxin and the structure can then be compared to the structure of podocalyxin in its native state, to obtain information that may be used to design compounds that mimic endoglycan antagonism of podocalyxin.

IV. Screening Assays

The present disclosure also includes screening assays for identifying agents that modulate endoglycan and/or podocalyxin and that are useful in modulating cancer cell growth. Agents that modulate include agents that stimulate endoglycan and/or podocalyxin (endoglycan and/or podocalyxin agonists) and agents that inhibit endoglycan and/or podocalyxin (endoglycan and/or podocalyxin antagonists).

In accordance with one embodiment, the disclosure provides a method for screening candidate compounds for their ability to modulate the activity of endoglycan and/or podocalyxin. The method comprises providing an assay system for assaying endoglycan and/or podocalyxin levels, assaying the levels in the presence or absence of the candidate or test compound and determining whether the compound has increased or decreased endoglycan and/or podocalyxin levels.

Accordingly, the present disclosure provides a method for identifying a compound that modulates podocalyxin comprising:

(a) incubating a test compound with podocalyxin or a nucleic acid encoding podocalyxin; and (b) determining the effect of the compound on podocalyxin activity or expression and comparing with a control (i.e. in the absence of the test substance), wherein a change in the podocalyxin activity or expression as compared to the control indicates that the test compound modulates podocalyxin.

In another embodiment, the present disclosure provides a method for identifying a compound that modulates endoglycan comprising:

(a) incubating a test compound with endoglycan or a nucleic acid encoding endoglycan; and (b) determining the effect of the compound on endoglycan activity or expression and comparing with a control (i.e. in the absence of the test substance), wherein a change in the endoglycan activity or expression as compared to the control indicates that the test compound modulates endoglycan.

The present disclosure also provides a screening assay that can be used to identify endoglycan agonists and/or podocalyxin antagonists.

Accordingly, the present disclosure provides a screening assay for identifying an antagonist of podocalyxin comprising the steps of:
(a) incubating a test substance with podocalyxin; and
(b) determining whether or not the test substance inhibits podocalyxin activity, function or expression levels.

In yet another embodiment, there is provided a screening assay that can be used to identify a podocalyxin antagonist comprising the steps of:
(a) incubating a test substance with cells expressing podocalyxin and CXCR4; and
(b) determining whether or not the test substance inhibits the colocalization of podocalyxin with CXCR4.

In another embodiment, the present disclosure provides a screening assay for identifying an agonist of endoglycan comprising the steps of:
(a) incubating a test substance with endoglycan; and
(b) determining whether or not the test substance activates endoglycan activity, function or expression levels.

The endoglycan and/or podocalyxin is generally immobilized in the above assays. In one embodiment, the endoglycan and/or podocalyxin is expressed on the surface of a cell, optionally a cancer cell.

Since endoglycan and podocalyxin both bind to NHERF, the disclosure also provides a method for identifying a compound that modulates NHERF comprising:
(a) incubating a test compound with NHERF or with cells expressing NHERF on its surface; and
(b) determining the effect of the compound on NHERF activity or expression and comparing with a control (i.e. in the absence of the test substance), wherein a change in the NHERF activity or expression as compared to the control indicates that the test compound modulates NHERF. A change in NHERF activity may include a change in response to endoglycan and/or podocalyxin.

Agents that modulate include agents that stimulate NHERF (NHERF agonists) and agents that inhibit NHERF (NHERF antagonists). In one embodiment, the screening assay can be used to identify NHERF antagonists.

In all of the above screening assays, the test compound can be any compound which one wishes to test including, but not limited to, proteins, peptides, nucleic acids (including RNA, DNA, antisense oligonucleotides, peptide nucleic acids), carbohydrates, organic compounds, small molecules, natural products, library extracts, bodily fluids and other samples that one wishes to test for modulators of endoglycan or NHERF.

One skilled in the art will appreciate that many methods can be used in order to determine whether or not a test substance can activate endoglycan, inhibit podocalyxin or modulate NHERF and therefore inhibit cancer cell growth. Once a compound is identified in a screening assay (Endoglycan agonist, podocalyxin antagonist or NHERF modulator), it may be tested in in vitro or in vivo assays to determine its effect on cancer cell growth.

The screening methods of the disclosure include high-throughput screening applications. For example, a high-throughput screening assay may be used which comprises any of the methods according to the disclosure wherein aliquots of cells transfected with endoglycan and/or podocalyxin are exposed to a plurality of test compounds within different wells of a multi-well plate. Further, a high-throughput screening assay according to the disclosure involves aliquots of transfected cells which are exposed to a plurality of candidate factors in a miniaturized assay system of any kind. Another embodiment of a high-throughput screening assay could involve exposing a transfected cell population simultaneously to a plurality of test compounds.

The method of the disclosure may be "miniaturized" in an assay system through any acceptable method of miniaturization, including but not limited to multi-well plates, such as 24, 48, 96 or 384-wells per plate, micro-chips or slides. The assay may be reduced in size to be conducted on a micro-chip support, advantageously involving smaller amounts of reagent and other materials. Any miniaturization of the process which is conducive to high-throughput screening is within the scope of the disclosure.

The disclosure extends to any compounds or modulators of endoglycan and/or podocalyxin identified using the screening method of the disclosure that are useful in treating cancer.

The disclosure also includes a pharmaceutical composition comprising a modulator of endoglycan and/or podocalyxin identified using the screening method of the disclosure in admixture with a suitable diluent or carrier. The disclosure further includes a method of preparing a pharmaceutical composition for use in modulating cancer cell growth comprising mixing a modulator of endoglycan and/or podocalyxin identified according to the screening assay of the disclosure with a suitable diluent or carrier.

The present disclosure also includes all business applications of the screening assay of the disclosure including conducting a drug discovery business. Accordingly, the present disclosure also provides a method of conducting a drug discovery business comprising:
(a) providing one or more assay systems for identifying a modulator of podocalyxin;
(b) conducting therapeutic profiling of modulators identified in step (a), or further analogs thereof, for efficacy and toxicity in animals; and
(c) formulating a pharmaceutical preparation including one or more modulators identified in step (b) as having an acceptable therapeutic profile.

In another embodiment, the present disclosure also provides a method of conducting a drug discovery business comprising:
(a) providing one or more assay systems for identifying a modulator of endoglycan;
(b) conducting therapeutic profiling of modulators identified in step (a), or further analogs thereof, for efficacy and toxicity in animals; and
(c) formulating a pharmaceutical preparation including one or more modulators identified in step (b) as having an acceptable therapeutic profile.

In certain embodiments, the subject method can also include a step of establishing a distribution system for distributing the pharmaceutical preparation for sale, and may optionally include establishing a sales group for marketing the pharmaceutical preparation.

The present disclosure also provides a method of conducting a target discovery business comprising:
(a) providing one or more assay systems for identifying modulators of podocalyxin;
(b) (optionally) conducting therapeutic profiling of modulators identified in step (a) for efficacy and toxicity in animals; and
(c) licensing, to a third party, the rights for further drug development and/or sales for modulators identified in step (a), or analogs thereof.

In another embodiment, the present disclosure provides a method of conducting a target discovery business comprising:

(a) providing one or more assay systems for identifying modulators of endoglycan;

(b) (optionally) conducting therapeutic profiling of modulators identified in step (a) for efficacy and toxicity in animals; and (c) licensing, to a third party, the rights for further drug development and/or sales for modulators identified in step (a), or analogs thereof.

V. Pharmaceutical Compositions

The present disclosure includes pharmaceutical compositions containing one or more modulators of endoglycan and/or podocalyxin. Accordingly, the present disclosure provides a pharmaceutical composition for use in modulating cancer cell growth comprising an effective amount of podocalyxin modulator in admixture with a suitable diluent or carrier. In another embodiment, the present disclosure provides a pharmaceutical composition for use in modulating cancer cell growth comprising an effective amount of endoglycan modulator in admixture with a suitable diluent or carrier. In a further embodiment, the present disclosure provides a pharmaceutical composition for use in modulating cancer cell growth comprising an effective amount of endoglycan modulator and podocalyxin modulator in admixture with a suitable diluent or carrier. In one embodiment, the pharmaceutical composition comprises a podocalyxin antagonist and a suitable diluent or carrier. In another embodiment, the pharmaceutical composition comprises a podocalyxin and/or CXCR4 antibody and a suitable diluent or carrier. In yet another embodiment, the pharmaceutical composition comprises a shRNA against podocalyxin and/or CXCR4 and a suitable diluent or carrier. In one embodiment the shRNA against podocalyxin is coded by the sequence as shown in SEQ ID NOs: 11, 12 or 13.

In one embodiment, the present disclosure provides a pharmaceutical composition for use in treating cancer comprising an effective amount of a podocalyxin antagonist in admixture with a suitable diluent or carrier. In another embodiment, the present disclosure provides a pharmaceutical composition for use in treating cancer comprising an effective amount of an endoglycan agonist in admixture with a suitable diluent or carrier. In a further embodiment, the present disclosure provides a pharmaceutical composition for use in treating cancer comprising an effective amount of an endoglycan agonist and a podocalyxin antagonist in admixture with a suitable diluent or carrier.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions. The endoglycan and/or podocalyxin or ligand is optionally injected in a saline solution either intravenously, intraperitoneally or subcutaneously.

The pharmaceutical compositions of the disclosure can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other anti-cancer agents.

A pharmaceutical composition comprising the nucleic acid molecules of the disclosure may be used in gene therapy to treat cancer. Recombinant molecules comprising a nucleic acid sequence encoding endoglycan molecule of the disclosure, or fragment thereof or an antisense podocalyxin molecule or fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. The nucleic acid molecules of the disclosure may also be applied extracellularly such as by direct injection into cells.

The following non-limiting examples are illustrative of the present disclosure:

EXAMPLES

Example 1

Podocalyxin

Materials and Methods
Tissue Microarray Construction

A total of 270 formalin-fixed, paraffin-embedded primary invasive breast cancer tissue blocks (archival cases from Vancouver General Hospital from the period 1974-1995) that had been graded according to the Nottingham modification of the Scarth, Bloom, Richardson method (Elston and Ellis, 1991) were used to construct a tissue microarray (TMA) as described previously (Parker et al., 2002). Briefly, a tissue-arraying instrument (Beecher Instruments, Silver Springs Md.) was used to create holes in a recipient block with defined array coordinates. Two 0.6 mm diameter tissue cores were taken from each case and transferred to the recipient block using a solid stylet. Three composite high-density tissue microarray blocks were designed and serial 4 µm sections were then cut with a microtome and transferred to adhesive-coated slides. Normal breast and kidney tissues were used as controls.

TMA Immunohistochemistry, Scoring and Correlation Analysis

Array and control tissue sections were deparaffinized and treated for 30 min at 90° C. with citrate buffer (pH 6.00) for antigen retrieval. The sections were then treated with 3% hydrogen peroxide in PBS for 30 min followed by incubation with the mouse monoclonal anti-human podocalyxin antibody 3D3 (1:80 dilution in 1% BSA in PBS; Kershaw et al., 1997a) overnight. Antibody binding was detected using the Envision detection system (Dako) and the sections were then counterstained with hematoxylin, dehydrated and mounted.

Staining of the TMA sections was scored semi-quantitatively based on the intensity of cytoplasmic staining and the proportion of cells stained: 0—no specific staining in the tumor cells; 1—diffuse, weak immunoreactivity or strong cytoplasmic staining reaction in <10% of the tumor cells; 2—diffuse intermediate immunoreactivity or strong cytoplasmic staining in 10-50% of cells; 3—strong cytoplasmic staining in >50% of the tumor cells. In the case of discrepancy between two cores from the same tumor sample, the higher score was used. All samples were evaluated and scored independently without knowledge of the patient's outcome information.

All scores were entered into a standardized Excel spreadsheet and processed using the software TMA-deconvoluter 1.06, Cluster and TreeView programs as previously described (Liu et al., 2002). Survival analysis was performed using the Kaplan-Meier method. Paired correlation analysis to nodal status, grade, size and p53, ER, PR, and HER2 status, all of which were previously assessed on the TMA (Parker et al., 2002, Liu et al., 2002; Makretsov et al., 2003) was performed using the bivariate two-tailed Pearson test. Multivariate survival analysis was performed using the Cox proportional hazard regression model. Differences were considered significant at $p<0.05$.

Cell Culture, Transfection and Podocalyxin Localization

T47D, MCF-7 and MDA-231 human breast cancer cell lines were maintained in DMEM/F12 medium supplemented with 5% FBS (Hyclone) and insulin (5 mg/ml). Endogenous podocalyxin expression was determined by Western blotting of whole cell lysates (20 µg total protein) using the antibody described above for the tissue array analysis.

MCF7 cells, which expressed low levels of endogenous human podocalyxin (see FIG. 2A) were transfected with a control empty pIRES-EGFP expression vector (BD biosciences) or with the same vector containing a full length mouse podocalyxin cDNA inserted into the multiple cloning site (BD Biosciences) using DMRIE-C reagent (Life Technologies/BRL). Stable transfectants were generated by continuous selection under G418 (500 µg/ml; Life Technologies/BRL). Successful transfection was determined by EGFP expression which, as expected, was heterogenous given that the transfectants were uncloned pools. Podocalyxin transgene expression, (which was also heterogeneous) was determined by immunofluorescence of confluent monolayers using an antibody specific for mouse podocalyxin (Doyonnas et al., 2001). The precise subcellular localization of the mouse podocalyxin was determined by confocal microscopy after dual staining of either the adherens junction protein E-cadherin (mouse monoclonal, Pharmingen, San Diego Calif.) or of the tight junction proteins occludin and ZO-1 (mouse and rat monoclonals respectively, Zymed, San Francisco Calif.). Here the heterogenous nature of the pooled populations was useful as it clearly demarcated consistent differences in the cell junctions of podocalyxin expressing cells.

Results

Podocalyxin Expression is Weak to Negative in Normal Breast Tissue

Normal kidney sections were immunostained with anti-human podocalyxin as a positive control for antibody specificity (Kershaw D B et. al., 1997a). As expected, podocalyxin was highly expressed on glomerular podocytes cells while expression was low to negative on tubular cells (FIG. 1A). This confirmed the specificity of immunocytochemical staining under the conditions used. Podocalyxin was also present in normal breast tissue but its expression was limited and it was spatially restricted. Specifically, podocalyxin was localized to the apical-most border in luminal epithelial cells (FIG. 1B; arrows). In addition, podocalyxin was present on the apical face of vascular endothelial cells as has been described previously (FIG. 1A, B; arrowheads, Kershaw et al. 1995, McNagny et al. 1997).

Podocalyxin is Expressed by Invasive Breast Carcinoma

To determine whether podocalyxin is upregulated by neoplastic breast tissue, an array of breast tissue samples was screened using an anti-podocalyxin antibody as probe. The clinicopathological characteristics of the 270 cases that made up the tissue microarray (TMA) are shown in Table 1. Sixty-one percent (165/270) of the invasive breast carcinoma cases on the TMA exhibited no discernable podocalyxin staining and were given a designation of '0' (FIG. 1C). Twenty-three percent (61/270) of the cases on the TMA exhibited weak staining in the majority of the tumor cells and they were given a designation of '1' (FIG. 1D). Eleven percent (31/270) of the cases exhibited a mixture of weak and intense-membrane staining (FIG. 1E). These three groups could not be distinguished from each other on the basis of clinical outcome. Specifically, Kaplan-Meier analysis of the overall survival (data not shown) and disease free survival (FIG. 2A) indicated that these three classifications were indistinguishable in terms of outcome.

Five percent (13/270) of the cases on the TMA exhibited a strong staining in the majority of the tumor cells and were originally given a designation of '3' (FIG. 1F). This designation had a significantly poorer outcome compared to the other three original designations as assessed by Kaplan Meier curve analysis (FIG. 2A; $p<0.02$). Therefore, this difference was statistically significant and readily observable when the 0, 1, and 2 designations were grouped and described as 'low or no podocalyxin' and compared to designation 3 described as 'high podocalyxin' (FIG. 2B $p<0.02$). In addition, the high podocalyxin tumors had a mean survival time of 9.5+/−1.9 years, which was significantly shorter than the mean survival time of 15+/−0.5 years for the combined low or no podocalyxin tumors. It was concluded that high level expression of podocalyxin is selective to the most metastatic tumors.

High Podocalyxin Expression is an Independent Marker of Poor Outcome

The same TMA that was used for podocalyxin staining has been previously stained for a number of markers that have prognostic significance for breast cancer outcome (Makretsov et al., Submitted and see www.pathology.ubc.ca/immuno). Thus, the inventors were able to perform a multi-variant Cox regression analysis in which high podocalyxin expression was compared with 6 other breast cancer-associated markers (Table 2). As expected, nodal status and HER2 overexpression were independent markers of poor outcome, which is an internal validation of the array analysis. Therefore, the fact that high podocalyxin expression on its own was associated with increased relative risk ($p<0.006$) indicates that it is an independent progonostic indicator of poor outcome. Interestingly, however, a Pearson correlation analysis of the same data indicated that high podocalyxin expression positively correlated with p53 mutations, Estrogen receptor loss, and increased tumor grade (Table 3; all p values <0.01). Thus, the data suggest that podocalyxin is an independent marker of metastatic tumors.

Figure 3:
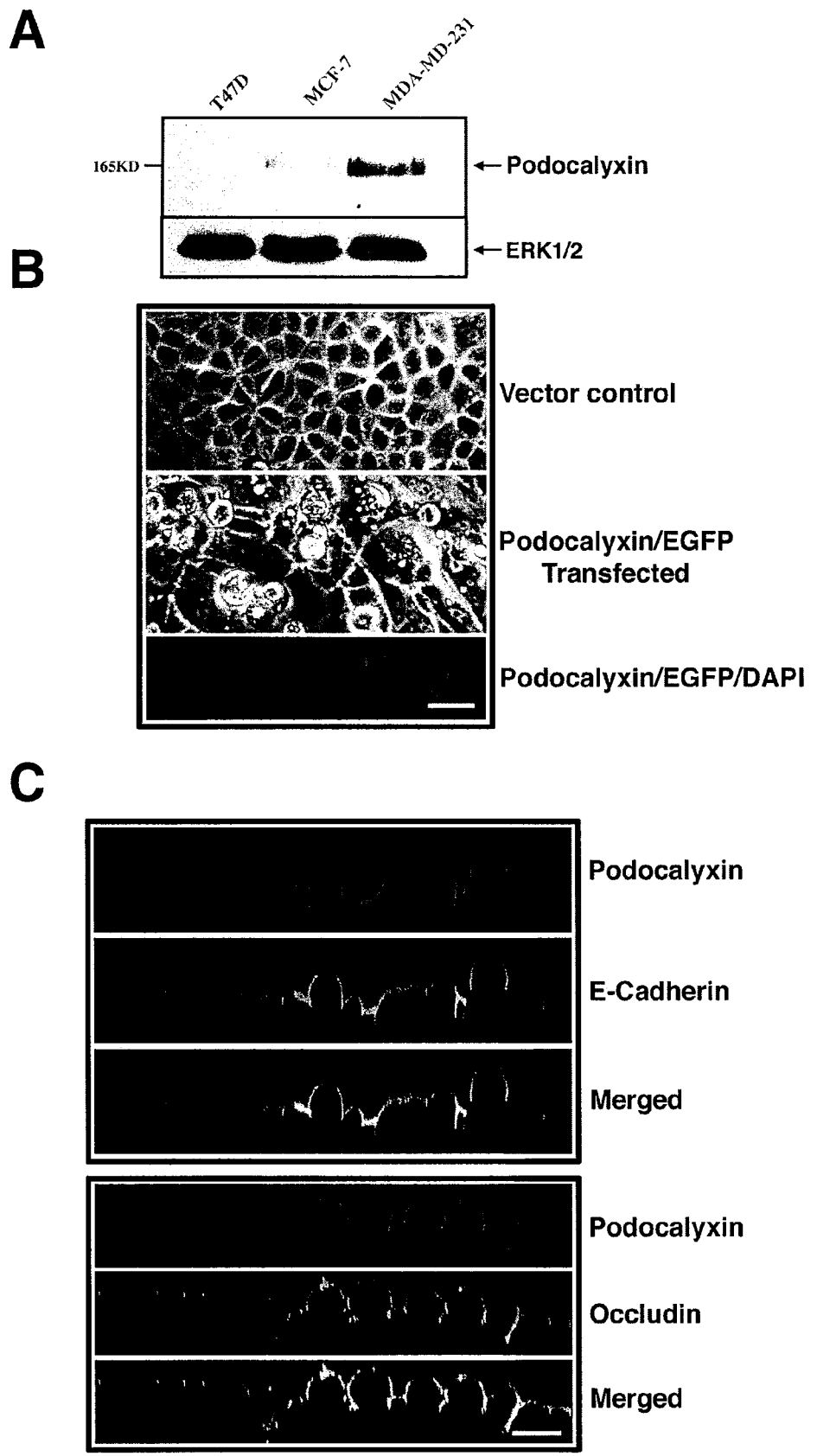
FIG. 3 illustrates the functional significance of podocalyxin overexpression in MCF-7 breast carcinoma cells.

Ectopic Podocalyxin Expression Leads to Disruption of Tight Junctions and Delamination of MCF-7 Breast Tumor Cells Previously it has been shown that ectopic expression of podocalyxin in kidney epithelial cells (MDCK), leads to disruption of cell junctions (Takeda et al., 2000). To determine if the same is true of breast carcinoma cells the inventors first examined endogenous levels of podocalyxin in human breast tumor lines. Specifically, MCF-7 and T-47D cells, which both are capable of forming cell junctions and morphogenic structures, expressed low levels of endogenous human podocalyxin compared to the high levels of expression in the highly invasive and metastatic MDA231 cells which do not form cell junctions (FIG. 3A). To test the functional significance of this expression, human MCF-7 cells were transfected with a control EGFP-expressing vector, or the same vector encoding EGFP and a full-length mouse podocalyxin. After selection drug resistance, the morphology of pooled heterogeneous populations of primary transfectants was examined. Control monolayers formed flat confluent monolayers that were undistinguishable from the parent line (data not shown). In contrast, pooled populations stably transfected with the EGFP/Podocalyxin vector contained areas where cells bulged outward from the monolayers (FIG. 3B). As these cultures reached confluence they often shed podocalyxin-expressing cells into the media. Coordinate, yet heterogeneous, expression of EGFP and mouse podocalyxin was confirmed by dual green channel fluorescence and immunostaining (FIG. 3B). Note also that podocalyxin was appropriately targeted to the apical membrane domain in the transfected cells (FIG. 3B lower panel).

Attempts to subclone high podocalyxin expressing cells failed as these cells were constantly shed from the substratum and were difficult to maintain in suspension. The inventors therefore attempted to more fully analyze the heterogeneous pooled populations produced in the primary transfections. This allowed the effects of heterogeneous podocalyxin overexpression on cell junctions to be analyzed by dual immunostaining. Interestingly, cells expressing low to negligible levels of the podocalyxin transgene formed normal adherens junctions with the expected basolateral expression of E-cadherin and apical expression of the tight junction protein, occludin along the lateral membranes at sites of cell-cell interaction (FIG. 3C). In contrast, E-cadherin and occludin both became widely distributed on the entire surface of highly overexpressing podocalyxin expressing cells (FIG. 3C). The latter cells were clearly being extruded from the monolayers as evidenced by their morphology and upward migration of their DAPI-stained nuclei. These data suggested that high levels of Podocalyxin expression can disrupt tight junction-dependent apical/basal polarity in mammary carcinoma cells. This conclusion was further supported by the finding that transepithelial resistance, which is a functional measure of tight junctions, was reduced from 497+/−37.2 ohms/cm2 in control-transfected MCF-7 monolayers to 210+/−11.9 ohms/cm2 in EGFP/Podocalyxin-transfected monolayers. Upexpression of podocalyxin in breast carcinoma cell lines leads to the disruption of cell-cell junctional complexes, mislocalization of cadherins and occludins and delamination from basement membranes, all features common to more aggressive forms of metastatic breast cancer.

Example 2

Endoglycan

Results
Tissue Distribution of CD34 Family Members

Data was compiled from published analyses on human and mouse CD34, Podocalyxin and Endoglycan (Krause 1996, McNagny 1997, Doyonnas 2001, Sassetti 2000) and from our unpublished observations on mouse Endoglycan. Endoglycan and Podocalyxin expression profiles were generated using unpublished data obtained from: 1) Northern blots of hematopoietic lineage cell lines, 2) RT-PCR of sorted hematopoietic subsets from bone marrow, 3) antibody stains and flow cytometry analysis using existing antibodies to CD34 (RAM34) Podocalyxin (PCLP1) and 4) Immunohistochemistry using the same antibodies. Results are shown in Table 4.

Preparation of Monoclonal Antibody with Specific Binding Against Endoglycan

Figure 6:
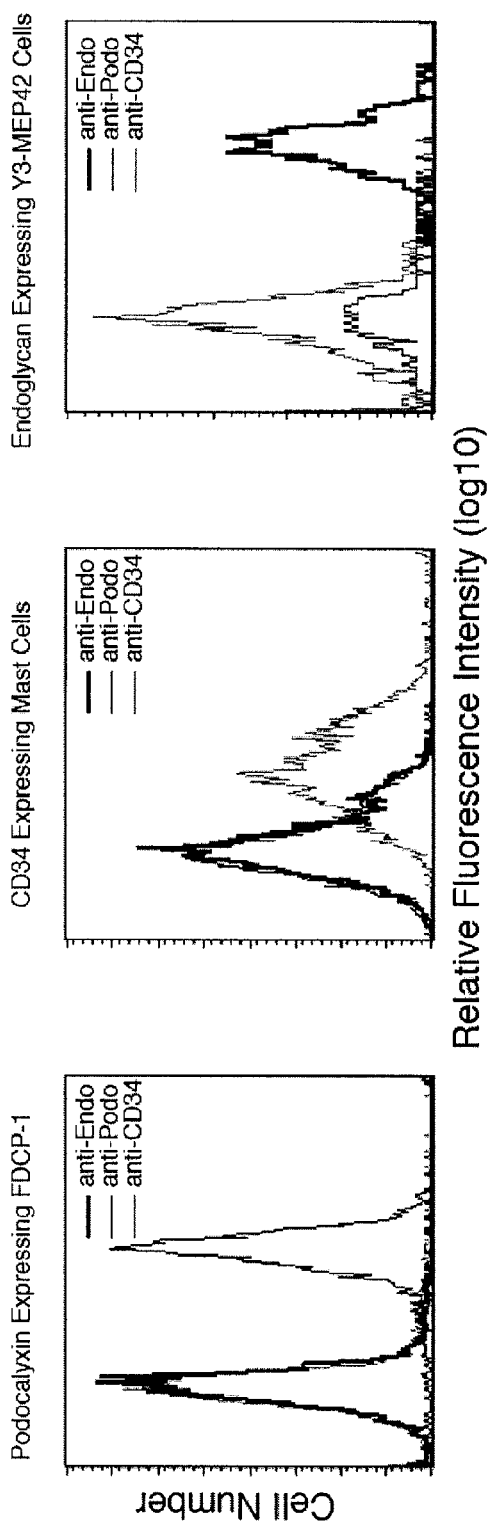
FIG. 6 shows the specificity of rat monoclonal antibody F4B10 to endoglycan compared to other CD34 family members.

To make the rat monoclonal antibody, rats were immunized with a peptide corresponding to sequence from the extracellular domain: V A S M E D P G Q A P D L P N L P S I L P K M D L A E P P W H M P L Q G G C (SEQ ID NO:10) linked to KLH and boosted with the entire extracellular domain fused to the Fc portion of Rabbit IgG1. Hybridomas were made using standard protocols and antibodies from these hybridomas were screened for reactivity with the peptide and Fc-fusion protein by ELISA. They were also screened for the ability to stain a rat myeloma cell line, Y3, which had been transfected to express full length Endoglycan. One antibody passed all criteria (F4B10). This antibody did not react with Y3 cells expressing CD34 or Podocalyxin so the antibody is specific for Endoglycan and not related family members (FIG. 6). In addition, this antibody reacts with mouse and human Endoglycan and so it may be a useful reagent for both species.

Expression of Endoglycan in Relation to Podocalyxin

Figure 7:
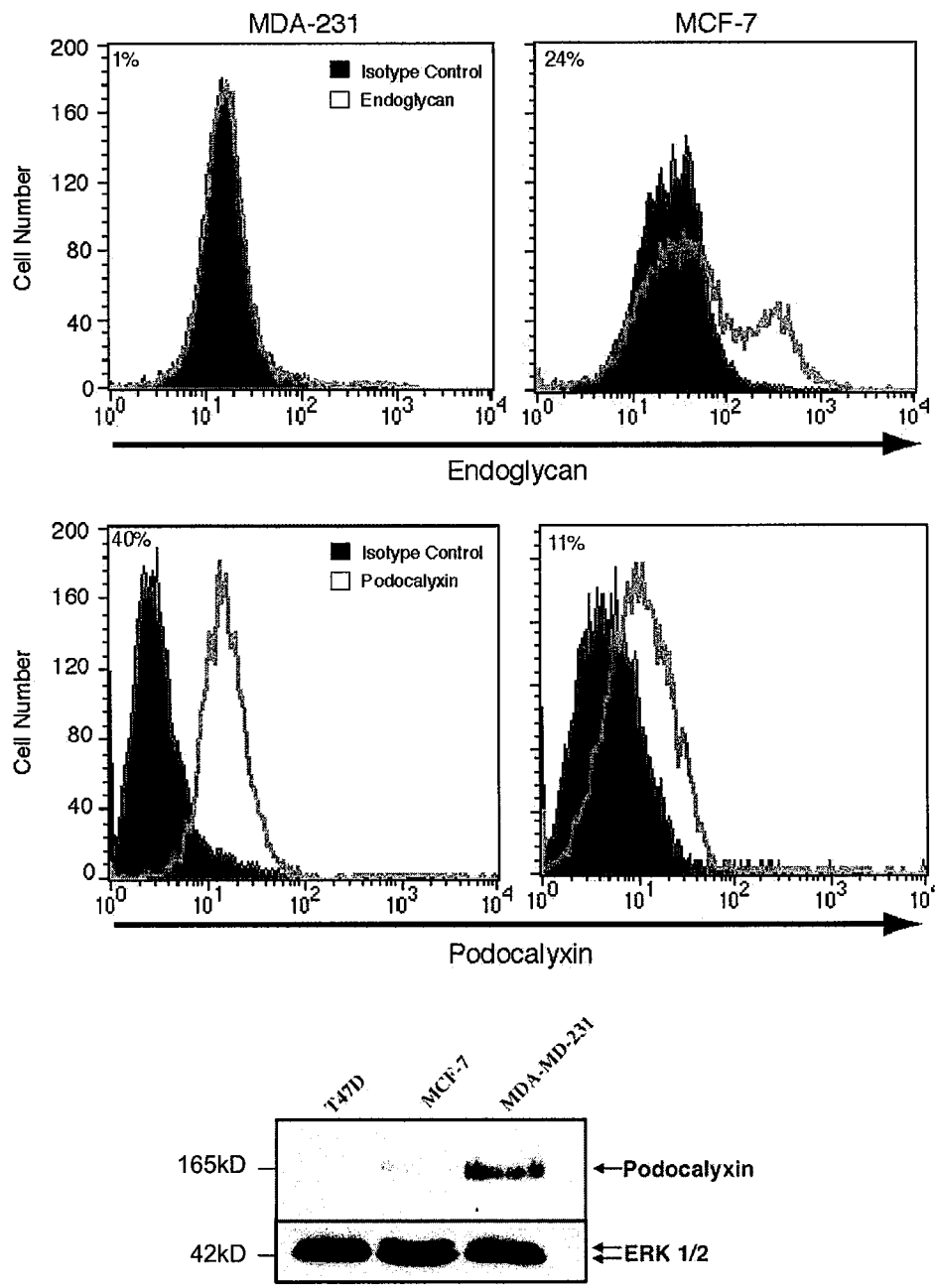
FIG. 7 shows reciprocal expression of Endoglycan and Podocalyxin by metastatic and non-metastatic breast carcinoma lines. FACS profiles showing Endoglycan and Podocalyxin expression by the metastatic, non-polarized cell, MDA-231 and the non-metastatic, polarized cell line MCF-7. Green lines=specific antibody staining. Below is a western blot to show relative levels of Podocalyxin in these lines. MCF-7 and a second non-metastatic line (T47D) express high levels of Endoglycan but little if any Podocalyxin. MDA-231, a metastatic line expresses high levels of Podocalyxin and no Endoglycan.

Endoglycan and Podocalyxin have a mirror image pattern of expression in breast cancer cell lines (FIG. 7). In MDA-231: metastatic tumor line where cells are non-polarized, Podocalyxin expression is high, whereas Endoglycan expression is negative. In MCF-7, a relatively non-metastatic line, cells maintain normal polarity, Podocalyxin expression is low, whereas Endoglycan is highly expressed. In T47D: a relatively non-metastatic line, cells maintain normal polarity, Podocalyxin expression is low, whereas Endoglycan expression is high. This was determined by indirect immunofluorescence using our new antibody and flow cytometry (FACS).

Figure 8:
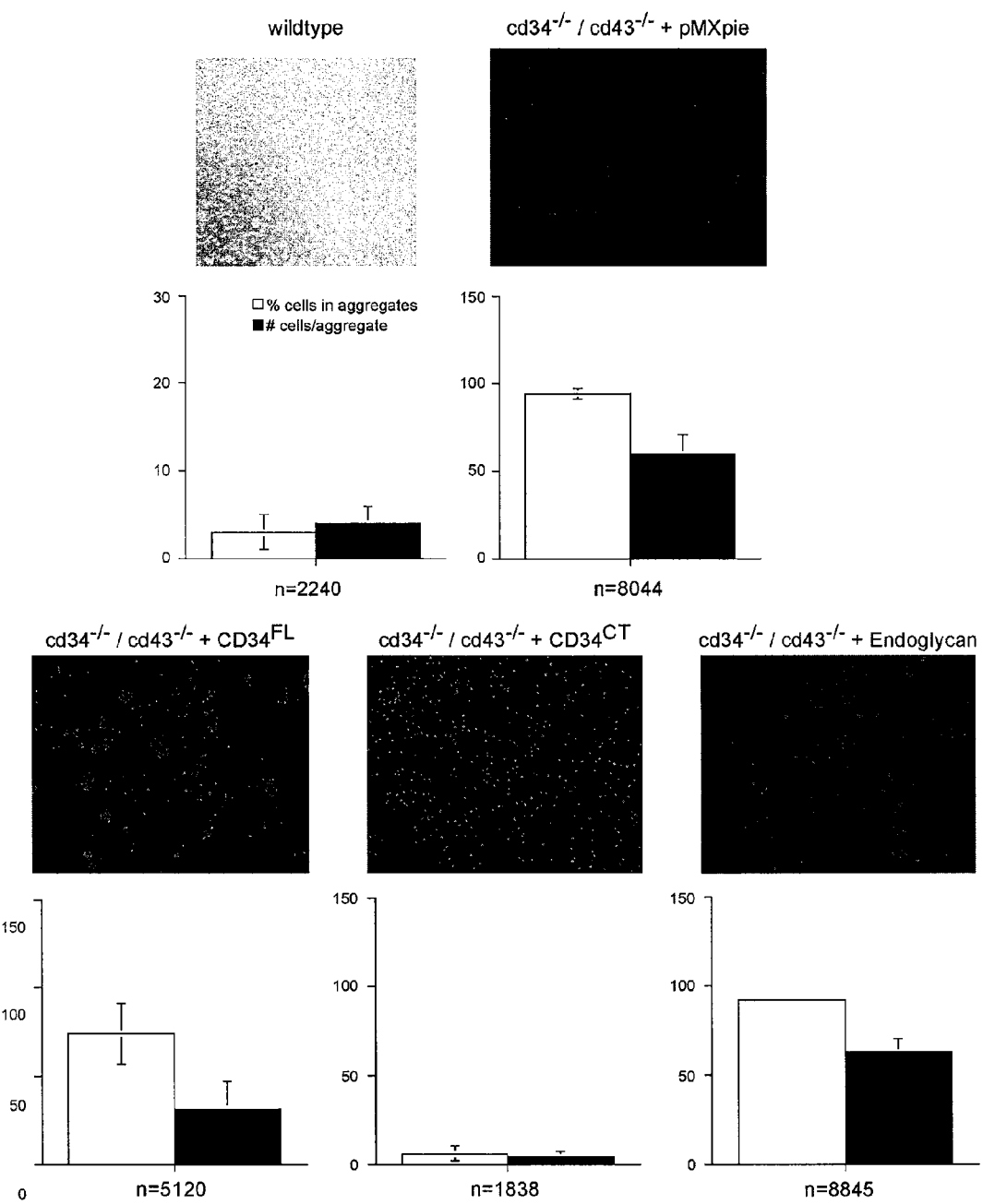
FIG. 8 shows failure of ectopic Endoglycan expression to block mast cell aggregation. (A) Mast cells from Wild type and cd34$^{-/-}$/cd43$^{-/-}$ infected with pMXpie retrovirus alone were plated at similar densities for assessment of aggregation. Graphs show data from two independently derived bone marrow mast cell cultures. (B) cd34$^{-/-}$/cd43$^{-/-}$ mast cells infected with pMXpie containing CD34$^{FL}$, CD34$^{CT}$ or Endoglycan. Graphs show data from two independent infections.

Function of Endoglycan:

Despite Endoglycan's similarity to CD34 and Podocalyxin, it may have a different function. Endoglycan was expressed in CD34/CD43 deficient mast cells. Pure mast cell cultures can be obtained by culturing mouse bone marrow in IL-3 for >4 weeks. Although normal mast cells grow in single cell suspensions, mast cells grown from CD34/CD43 KO mice tend to form large aggregates. Infection of mast cells with a retrovirus expressing ectopic CD34 reverses this aggregation and suggests that the normal function of CD34 is to block adhesion. In side by side experiments, ectopic expression of Endoglycan had no effect suggesting that it does not block adhesion and may instead have a pro-adhesive function. (FIG. 8).

Discussion

The present inventors have demonstrated that abnormally high podocalyxin expression and low endoglycan expression is a novel prognostic indicator of poor outcome in invasive breast carcinoma.

Tissue microarrays afford investigators the opportunity to carry out a rapid and relatively thorough screening of molecules that are believed to be important in specific tissues or pathologies (Kononen et al., 1998). The power of this technology is exemplified here where only 13 of the 270 cases on our TMA had uniformally high podocalyxin expression and yet this is clearly informative with respect to prognostic outcome. The inventors are currently assembling a 3000 case invasive breast cancer TMA linked to treatment and outcome that should allow this resolving power to be increased significantly and evaluate the role of different therapies on podocalyxin status of tumors.

Locally invasive breast cancers can have markedly different treatment responses and outcomes. Thus, it is extremely difficult to predict which patients will most benefit, or not benefit, from adjuvant therapy (Eifel et al., 2001). Genome-wide searches and large-scale expression profiling followed by cluster analysis have had some impact on this problem (Polyak et al., 2002), particularly with respect to identifying those tumors that do not progress (van't Veer et al., 2002). Despite these advances, the identification of novel independent indicators of poor outcome continues to be useful, even if they are only important in a small proportion of tumors, because they facilitate the development of new classification parameters that increase the resolving power of high throughput genomic and expression approaches. In addition, if these markers play a functional role in the biology of metastatic progression they may be rational therapeutic targets and further experimental investigations may lead to the discovery of other functionally relevant molecules in progression. This has clearly been proven to be the case with erbB2 (Nabholtz and Slamon, 2001).

CD34 and podocalyxin, expressed by high endothelial venules (HEV) are decorated with the appropriate glycosylations to make them adhesive ligands for L-selectin expressed by circulating lymphocytes. This type of posttranslational modification is exquisitely tissue-specific and the vast majority of endothelial cells and hematopoietic cells expressing CD34 type proteins lack this modification. On all other cell types, the data suggest that these molecules serve as blockers of adhesion via their bulky, negatively-charged mucin domains, as has been demonstrated by both loss- and gain-of-function experiments (Doyonnas et al. 2001 and Takeda et al. 2000). The experiments described here clearly delineate an anti-adhesive role for podocalyxin.

Initial functional experiments suggest that forced podocalyxin over-expression disrupts tight junctions in well-behaved MCF-7 breast carcinoma cells. Specifically, transepithelial resistance, a functional indicator of tight junction patency was significantly reduced and the spatially-restricted tight junction-associated protein occludin became very diffusely localized. Moreover, it was found that the tight junction-associated, PDZ domain-containing protein ZO-1 was mislocalized and relocalized basally in podocalyxin expressing cells (data not shown). These observations indicate that podocalyxin can function as an anti-adhesive molecule in breast cancer cells and they agree with previous findings in kidney epithelial cells where podocalyxin overexpression was shown to disrupt tight junction function and protein localization (Takeda et al., 2000) in vitro and podocalyxin loss was shown to lead to inappropriate tight-junction maintenance in vivo. In future experiments it will be interesting to determine if the potential PDZ-binding site at the extreme C-terminus of the podocalyxin cytoplasmic domain (Doyonnas et al., 2001; Takeda et al., 2001) contributes to this disruption of the tight junction. As this site also contributes to the association of podocalyxin with the actin cytoskeleton it may be involved in the cytoplasmic mislocalization of the protein itself that we observed in high expressing breast tumors (see FIG. 1F).

The adherens junction protein E-cadherin is often down-regulated in lobular breast carcinomas but not in the much more prevalent ductal forms of the disease. Forced expression of podocalyxin did not cause a loss of E-cadherin expression in MCF-7 cells. Instead, it altered its localization. Specifically, E-cadherin remained at the membrane but rather than being restricted to the basolateral domain the adherens junction protein was found along the entire circumference of high podocalyxin expressing cells that were being extruded from the MCF-7 monolayers. This could explain the somewhat paradoxical observation that circumferential E-cadherin localization is associated with poor outcome in grade III ductal breast carcinomas (Gillet et al., 2001). It also suggests that high podocalyxin expression may be disrupting apical-basal polarity in breast epithelial cells, which is also one function of abnormal erbB2 signaling (Brugge). A loss of polarity has been assumed to be functionally important in breast carcinoma progression, but this possibility has not yet been formally tested (Roskelley and Bissell, 2002). The inventors are currently carrying out such experiments using a 3-dimensional model of normal, polarized mammary epithelial cell morphogenesis (Roskelley et al., 2000).

Although a detailed dissection of the podocalyxin promoter regulatory elements has not yet been performed, it has recently been shown to be a direct transcriptional target of the Wilm's Tumor suppressor protein, WT1 (Palmer R E et al. Current Biology 2001). The role of WT1 in tumor progression is, at present, contentious. A tumor suppressive effect of this protein is supported by its loss in renal tumors and its ability to induce differentiation and cell cycle arrest of kidney and hematopoietic lineage cells. On the other hand, upregulation of WT1 expression is frequently observed in acute myeloid and lymphoid leukemias. An explanation for this apparent paradox could be the disrupted circuitry in tumor cells. For example WT1 may induce both a differentiation and cell cycle arrest program in normal cells, whereas tumor cells may have become refractory to the cell cycle arrest and only express differentiation antigens like podocalyxin.

Since Endoglycan and Podocalyxin have very similar sequences in the cytoplasmic domain, they may be natural antagonists of each other: Endoglycan may promote adhesion, maintain cell polarity, and block metastasis, and Podocalyxin may block adhesion and decrease cell polarity and increase metastasis. One theory is that endoglycan and podocalyxin compete for binding to NHERF1; a molecule that has previously been shown to link Podocalyxin to the actin cytoskeleton (Takeda et al., 2001). This then would allow these molecules (with opposing functions) to compete for localization in adhesion structures.

Example 3

Material and Methods:
FDC-P1 Cells

For all experiments and maintenance purposes (unless otherwise indicated), factor dependent cell-Paterson1 cells (FDC-P1) were grown in complete RPMI (Hyclone, Logan, Utah) media (10% FBS, 4 mM L-glutamine, penicillin and streptomycin (all from Gibco-Invitrogen, Burlington, ON)) with the addition (10% v/v) of WEHI-3B conditioned media as a source of mIL-3.

Lentiviral shRNA Infection of FDC-P1

Silencing-RNA target sequences were designed using PSI Oligomaker v1.5 (http://web.mit.edu/jacks-lab/protocols/pSico.html) and the resulting oligos were generated by Invitrogen (Burlington, ON). Lentiviral infection was performed using an adaptation of a protocol previously described (Rubinson et al., 2003). The expression vector, pLL3.7 kb+2.0 kb spacer, was a generous gift from Dr. Fabio Rossi (University of British Columbia, Vancouver, BC). shRNA oligos were annealed at 55° C. for 40 cycles, cloned into pLL3.7 plasmids and propagated in E. coli. Plasmids were transfected via calcium phosphate into 293T along with packing plasmids, pVSVg, p-MDLgag/pol and p-RSV-rev. FDC-P1 cells were incubated for 48 hours at 37° C. in viral supernatants collected from infected 293T cells 36 hours after transfection. FDC-P1 cells expressing GFP were selected by FACS and then cultured with 1 μg/mL G418 (Sigma-Aldrich, Oakville, ON) to enrich for positively-infected cells. Drug-selection was discontinued two weeks prior to experiments. Cells expressing silencing RNA vector transgenes were routinely screened for GFP co-expression by flow cytometry.

Antibodies

The endoglycan-specific monoclonal antibody (F4/B10, mouse IgM) was generated inhouse using the extracellular domain peptide N-VASMEDPGQAPDLPNLPSILPKMD-LAEPPWHMPLQGGC-C (SEQ ID NO:10) of mouse endoglycan as immunogen (Merkens and McNagny, in preparation). Anti-CD44 was a gift from Dr. Pauline Johnson (UBC, Vancouver, BC). CD43 (rat IgG2a$_\kappa$, clone S11) was generated from hybridomas in-house. Anti-podocalyxin (clone 192703) and rat IgG2b isotype control antibodies were purchased from R&D Systems (Minneapolis, Minn.). All other antibodies used were from commercial sources including anti-$\alpha$4 integrin, Ter119-PE, c-Kit and PECAM (BD Pharmingen, Mississauga, ON) and $\beta$1-integrin (BD Transduction Labs). All secondary antibodies for immunocytochemistry (goat anti-rat AlexaFluor488 and donkey anti-goat AlexaFluor568) were from Molecular Probes-Invitrogen (Burlington, ON). Horse-radish peroxidase (HRP) conjugated detection secondary antibody for immunoblots was from Dako (Mississauga, ON). CXCR4 antibody for immuoblotting applications was from Abcam (Cambridge, Mass.) or, for flow cytometry applications, from BD Biosciences (Mississauga, ON). pAkt (S473) antibody was from Cell Signaling Technology (NEB, Pickering, ON).

Proliferation (MTS) Assay

Cells ($1\times10^3$) were added to each well with fresh FDC-P1 growth media with or without test factors and incubated at 37° C. for the times indicated in the figures and legends. An MTS assay (Promega, Madison, Wis.) optimized for a 96-well format was performed according to the manufacturer's instructions as a surrogate assay of FDC-P1 proliferation. Briefly, a fixed volume aliquot of freshly resuspended cells was transferred to a test well with the MTS reagents and then incubated for 1 to 4 hours at 37° C. Chemifluorescence was recorded at 495 nm absorbance using a Spectromax 3000 and analyzed with SoftMax-pro software.

Flow Cytometry, Cell Sorting and Immunofluorescence Microscopy

Cells were fixed with 4% paraformaldehyde (Sigma) for 15 minutes, washed four times with blocking buffer (1% BSA in PBS), permeabilized with 0.1% Triton X-100 (Sigma) for 15 minutes and washed and additional four times with blocking buffer (all at room temperature). After permeabilization, cells were blocked with 10% goat serum for 20 minutes. Cells were incubated with 2 µg/ml anti-podocalyxin antibodies for 15 minutes, washed four times with blocking buffer and labelled with fluorescent goat anti-rat AlexaFluor antibodies for 15 minutes prior to analysis flow cytometry (FACSCalibur; BD Biosciences, Mississauga, ON). For confocal immunofluorescence microscopy, cells were fixed, permeabilized and labeled as described above but then allowed to settle on poly-L-lysine (Sigma) coated slides for 30 minutes in the dark. Slides were then mounted with Fluoromount G (Southern Biotech, Birmingham, Ala.) with a cover slip for analysis using an inverted-objective confocal microscope (Olympus FV1600).

In vitro Migration Assay

FDC-P1 cells were washed twice with pre-warmed RPMI, resuspended in complete RPMI media (without WEHI-3B IL-3-conditioned media) and starved of IL-3 for three hours at 37° C. One day prior to migration assays transwell filters (5 µm; Costar, Corning, Lowell, Mass.) were coated with 100 µg/ml fibronectin (Chemicon-Millipore, Temecula, Calif.) or plated with $2.5\times10^4$ M210B4 stromal cells (a generous gift from Dr. Connie Eaves, BC Cancer Research Centre, Vancouver, Canada). For transwells coated with fibronectin, wells were washed four times with PBS and blocked with 5% BSA in PBS for 2 hours at 37° C. For stroma-coated transwells, the monolayer of each well was verified visually to ensure full coverage of the filter surface area. For the migration assay using both matrices, $1\times10^6$ of test cells were added into the upper chamber of the transwell filter and 500 µl of media with 100 nM CXCL12 (made from the BRC in house peptide facility) or 200 ng/ml SCF (R&D Systems) or a pre-mixed cocktail of both was added to the lower chamber. Cells were then incubated for six hours at 37° C. The upper chamber was carefully removed and cells that passed into the lower chamber were resuspended in a fixed volume and counted manually using a calibrated hemacytometer.

Mice and Harvest of E15.5 Fetal Liver Cells

The generation and maintenance of Podxl−/− mice has been described (Doyonnas et al., 2001; Doyonnas et al., 2005). Podocalyxin-deficient fetal liver cells (FTL) were obtained from timed-matings of Podxl+/− mice. At E15.5, pregnant females were sacrificed by $CO_2$ asphyxiation and embryos were carefully extracted. Sample tissues (tail snip) were obtained from each embryo for genotyping and, in parallel, fetal livers were carefully removed from the embryo. Sterile PBS was used to generate single cell suspensions of each fetal liver. FTL cells were subsequently labeled with PE-coupled Ter119 antibodies (eBiosciences, San Diego, Calif.) for 15 minutes, washed, and then incubated with magnetic anti-PE microbeads (autoMACS, Miltenyi Biotec, Auburn, Calif.) and then applied to a MACs magnetic-column (autoMACS) to deplete Ter119+ cells. Ter119-negative FTL was recovered from the column flow-through and washed twice with sterile RPMI media supplemented with 10% WEHI-3B. Cells were counted and resuspended to the appropriate concentration before loading into the transwells.

Adhesion Assay

Flat bottom 96-well plates (Nunc, Thermo Fisher Scientific, Rochester, N.Y.) were coated overnight at 4° C. with 100 µg/ml fibronectin. Wells were washed four times with Hanks Balanced Salt Solution (HBSS) (Gibco) and blocked with 3% BSA in PBS at 37° C. for two hours. After blocking, wells were washed again three times with HBSS. FDC-P1 were washed twice with HBSS and $1\times10^6$ cells were re-suspended in 1 mL RPMI media containing 3 µg of Calcein-AM (Invitrogen) and labeled according the manufacturer's instructions. After labeling, cells were washed three times with HBSS and re-suspended in RPMI complete media without phenol-red (Gibco). Cells were IL-3-deprived for 3 hours, and then $2\times10^5$ cells were added (in triplicate) to pre-blocked wells and then stimulated with 200 ng/ml of SCF or 100 nM of CXCL12 or both for the times indicated. At each time point, a pre-wash and a post-wash (each well was carefully washed four times) measurement were recorded with a spectrofluorimeter (450 nm). Percent adhesion was calculated based on the post-washed fluorescence divided by prewashed fluorescence.

Short-term Bone Marrow Homing Assay

Fetal liver cells from E15.5 embryos were labelled with Calcein-AM and a total of $8\times10^6$ cells were infused into each non-irradiated C57Bl/6 recipient by tail vein injection. After 3 hours, recipients were sacrificed by $CO_2$ asphyxiation and femurs and tibias removed. Bones were flushed with sterile PBS using a 25 G needle and resuspended in FACS buffer (PBS containing 1% FBS). Cells suspensions were analyzed by flow cytometry (FACSCalibur) ~$1\times10^6$ million events were collected for each mouse and the number of Calcein AM-labelled cells recovered was determined.

Immunoblotting

SDS-page fractionation of FDC-P1 cell lysates was performed as previously described (Tan et al., 2006). For immunoblotting, nitrocellulose membranes were blocked with 10% BSA or skim milk (in TBS-Tween) for two hours at room temperature. Membranes were incubated with primary antibodies overnight at 4° C. and, after thorough washing with TBS-Tween, incubated with HRP-conjugated secondary antibodies for 1 hr before analysis by chemiluminescence (ECL, Amersham-GE Health Biosciences, Piscataway, N.J.).

Analytical Tools and Statistics

All statistical analyses were performed using student's paired t-test (95% confidence interval) and error bars in the figures represent the standard deviation from the mean unless otherwise indicated. Flow cytometry data was analyzed using FlowJo (TreeStar Inc., Ashland, Oreg.) and all cell image analyses with Fluoview 006.

Results:

Podocalyxin Gene-silencing

FDC-P1 cells are a growth factor dependent myeloid progenitor cell line derived from a long-term culture of bone marrow cells from normal mice (Dexter et al., 1980). These cells express all three members of the CD34-family on the cell membrane surface to varying degree with high levels of podocalyxin, modest to low CD34 surface expression and very low to barely detectable expression of endoglycan. To assess the importance of podocalyxin in hematopoietic precursor function, FDC-P1 cells were infected with podocalyxin specific short-hairpin (sh)RNA lentiviral vectors to silence podocalyxin expression (FIG. 9A). Three independent podocalyxin-inhibitory lentiviral constructs were generated (shPodoA, B and C) and the efficiency of suppression was assessed by flow cytometry (FIG. 9B) and confocal microscopy (FIG. 9C). Two constructs, shPodoA and shPodoB, effectively ablated podocalyxin expression while another, shPodoC, reduced expression by 85% (shift in mean fluorescence intensity from 101 to 15). FDC-P1 control cells containing only an empty or luciferase-specific shRNA vector (shLuc) proved to have similar podocalyxin surface expression as the non-infected FDC-P1 parental line. Subsequently, the stably expressing FDC-P1 lines expressing shPodoA and shPodoB were used for further functional analyses. The results of these studies described below focus primarily on the data obtained using the shPodoA line (with appropriate controls) but the results were identical to those obtained with shPodoB.

Podocalyxin-suppression Does not Affect FDC-P1 Proliferation

Figure 10:
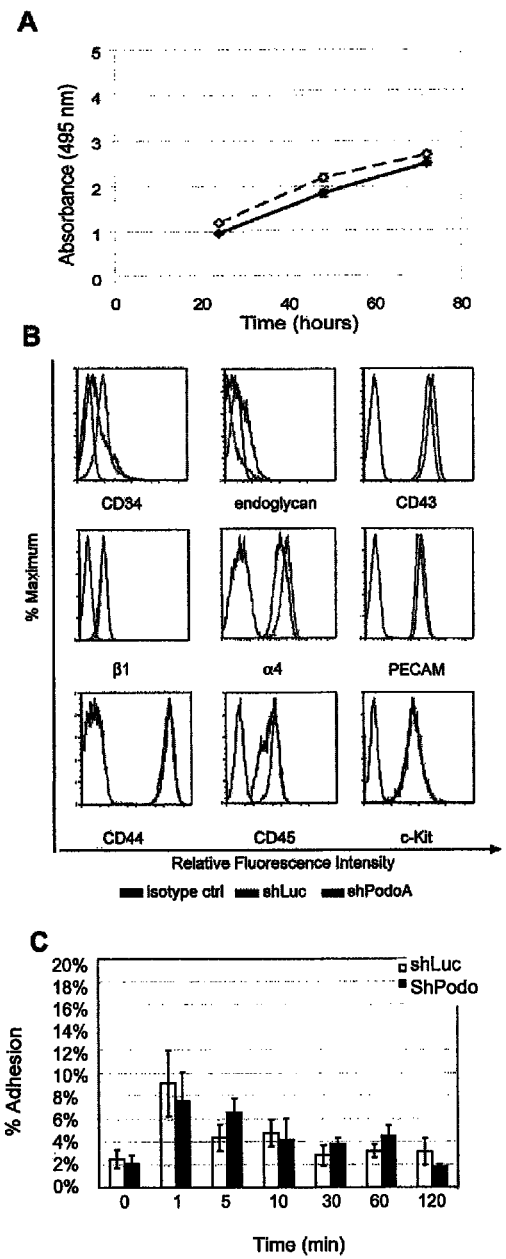
FIG. 10 shows podocalyxin-deficient FDC-P1 cells proliferate normally and express normal levels of adhesion and differentiation surface antigens. (A) MTS assay as a surrogate for monitoring proliferation of FDC-P1 expressing shLuc (open symbol, dotted line) and shPodoA (closed symbols, solid line) over a 72 hr time course. (B) Expression levels of surface antigens in shLuc and shPodo-infected FDC-P1. Isotype controls for shPodo was identical for shLuc in each experiment, thus only the isotype controls for shLuc are shown. (C) Adhesion of FDC-P1 to fibronectin matrix (% of total cells added) after stimulation of starved cells with media alone or media containing SCF, CXCL12 or SCF+CXCL12 for the times indicated (0-120 min).

It was first determined whether silencing podocalyxin expression influenced proliferation and viability of FDC-P1 cells. As shown in FIG. 10A, no major differences were observed in the proliferation of shLuc and shPodo cells over 72 hours. In addition, shLuc and shPodo cells consistently exhibited over 90% viability by trypan blue dye exclusion cell counts over the same time period. These results are consistent with previous observations that Podxl−/− fetal liver cells from E15.5 embryos do not display perturbed growth or survival (Doyonnas et al., 2005). Since it has been postulated that the members of the CD34-family share overlapping and compensatory functions in cells expressing more than one member (Doyonnas et al., 2001; Doyonnas et al., 2005), the surface expression profiles of CD34 and endoglycan were next examined in cells expressing podocalyxin-silencing siRNA. While the expression of endoglycan in shPodoA FDC-P1 is similar to shLuc controls cells (or perhaps slightly reduced), the expression of CD34 is increased above the shLuc control by 3 to 5 fold (FIG. 10B).

Deletion of Podocalyxin Does not Affect FDCP-1 Adhesion to Fibronectin

It has been shown that when over-expressed by adherent tumor cell lines, podocalyxin acts as an anti-adhesive molecule and results in reduced cell aggregation, increased apical membrane domain expansion and a disruption of cell-cell junctions (Nielsen et al., 2007; Somasiri et al., 2004). Correspondingly, it was predicted that loss of podocalyxin from hematopoietic precursor cells would result in excessive adhesion to fibronectin or stromal cells—an effect with the potential to influence cell migration.

In advance of addressing this possibility, shLuc and shPodo cells were first examined for levels of $\alpha 4\beta 1$ integrin (VLA4) expression, a well-known hematopoietic precursor receptor for fibronectin. Fibronectin was chosen since it is an extracellular matrix component secreted by cells in bone marrow stem- and progenitor-cell niche, and, previous work has suggested that $\alpha 4\beta 1$ integrin is key for HSC homing and migration (Papayannopoulou and Nakamoto, 1993; Williams et al., 1991). As shown in FIG. 10B, flow cytometric analyses revealed no major changes in the expression levels of the VLA4 $\beta 1$ subunit but perhaps a small increase in the expression of $\alpha 4$. FDCP1, shLuc and shPodo cells were also assessed for the expression of a panel of hematopoietic cell adhesion antigens and differentiation markers via flow cytometry (FIG. 10B). These included CD45, c-kit, the cell surface sialomucin CD43, and cell adhesion molecules CD44 and PECAM-1 (CD31). No major changes were observed in the levels of surface expression of these markers. Thus, shRNA podocalyxin-specific vectors were highly selective for the target gene and do not indiscriminately influence the surface expression profile or differentiation state of FDC-P1.

It was found that FDC-P1 do not adhere robustly to fibronectin in response to IL-3, and, deletion of podocalyxin does not significantly alter FDC-P1 adhesiveness. Although FDC-P1 cells are not known to grow in the presence of SCF alone (unless otherwise conditioned) (Engstrom et al., 2003), by flow cytometry analysis expression of its receptor, c-kit, was detected in these cells. Therefore SCF, CXCL12 and a pre-mixed cocktail of SCF+CXCL12 were tested in a fibronectin adhesion assay. The results show that suppression of podocalyxin expression in FDC-P1 did not influence fibronectin adhesion in response to these factors alone or in combination (FIG. 10C). In summary, the data suggest that suppression of Podocalyxin in FDC-P1 cells has only minimal effects on proliferation, differentiation, surface marker expression and adhesion.

Podocalyxin Enhances SCF+CXCL12 Mediated Hematopoietic Cell-migration

Figure 11:
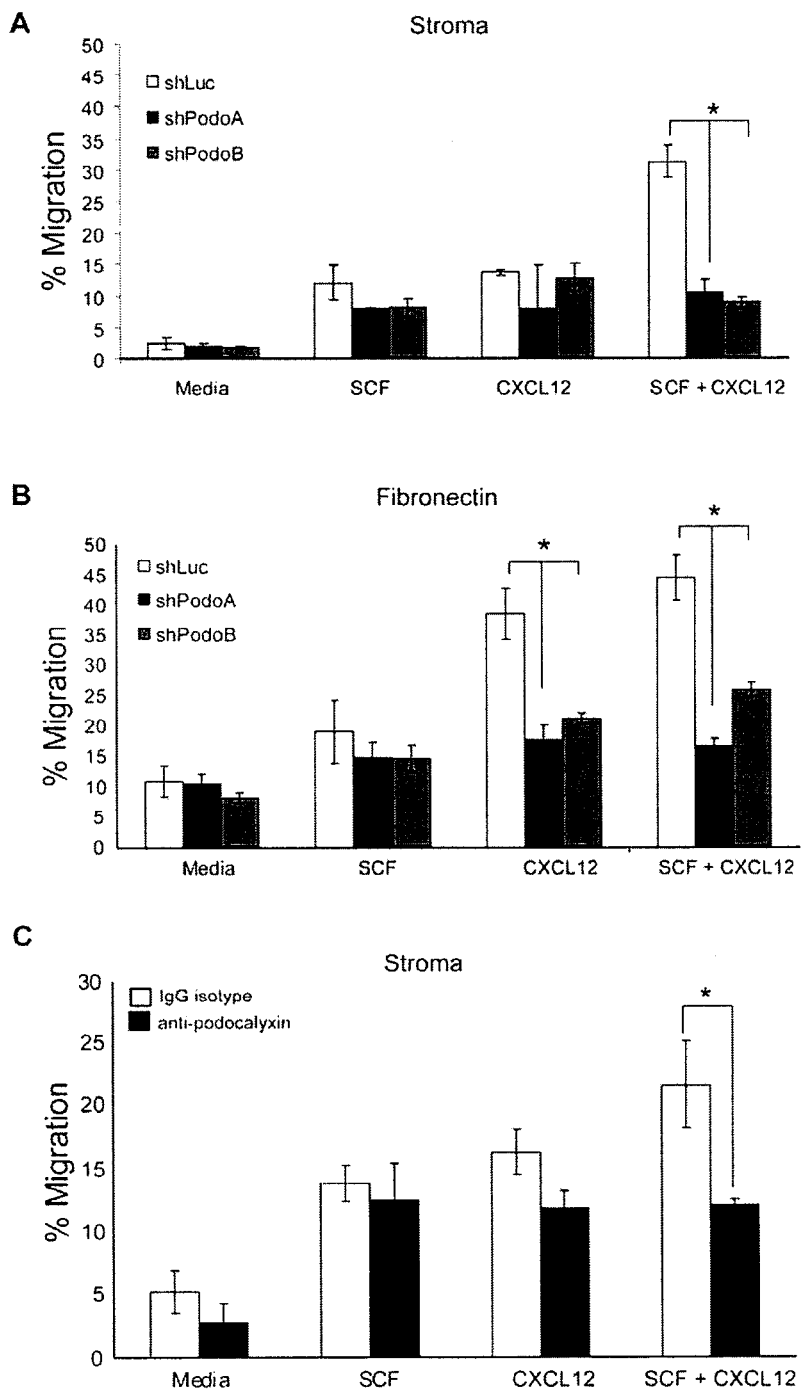
FIG. 11 shows suppression of podocalyxin-expression by shRNA or blocking surface exposure of podocalyxin specific-antibodies impairs migration of FDC-P1 towards SCF+CXCL12. In vitro migration assay of shLuc (open bars), shPodoA (solid bars) and shPodoB (shaded bars)-expressing FDC-P1. Cells from the upper chamber of (A) stromal cell layer or (B) fibronectin-coated transwells were exposed to a concentration gradient of stimulant consisting of media alone, SCF, CXCL12 or SCF+CXCL12. Percent of cells passing into the lower chamber after 6 hrs were enumerated and plotted as a function of total cells applied to the upper chamber. (C) Migration of FDC-P1 cells treated with podocalyxin-specific antibodies (black bars) or isotype control (open bars) across stroma-coated transwell filters. Cells passing through to the lower chamber after 6 hrs were enumerated and plotted as a percentage of total cells. *Statistically significant difference, $p<0.05$.

The in vitro migration of wild-type and podocalyxin knock-down FDC-P1 cells were evaluated using transwell assays. Stromal monolayers were grown on the surface of the filter in the upper chamber of each transwell filter (5 μm pores) and chemotactic factors were added to the bottom chamber to produce a gradient. Upon testing several concentrations of IL-3, SCF and CXCL12 in these assays it was found that IL-3, SCF or CXCL12 as lone factors yield no detectable (eg, IL-3) to modest (eg, SCF or CXCL12) cell migration through the stroma-coated transwell (FIG. 11A). In addition, there was no significant difference detected in migration between the control and podocalyxin-deficient FDCP-1. However, in four independent experiments it was found that podocalyxin-deficient cells were severely impaired (63±2.2%) in their ability to migrate across stroma-coated transwells when a pre-mixed cocktail of SCF+ CXCL12 was used as chemoattractant (FIG. 11A). The requirement for both factors is consistent with previous reports suggesting that activation of receptor tyrosine kinases augments CXCR4-dependent chemotaxis (Hart et al., 2004; Lapidot and Kollet, 2002).

In order to determine whether the effects of podocalyxin on chemotaxis required factors modified or produced by stromal cells, or, if an adhesive matrix alone was sufficient for FDC-P1 migration, these migration assays were repeated using fibronectin-coated transwells. Under these conditions, migration of shPodo-expressing cells was also severely impaired (68±2.2%) compared to control FDC-P1 (FIG. 11B). Thus podocalyxin-dependent migration of FDC-P1 in response to CXCL12 or SCF+CXCL12 is mediated, at least in part, through an integrin-fibronectin adhesion mechanism.

To test if the observed migration defect in podocalyxin-deficient FDC-P1 was also applicable to primary cells, similar migration assays were repeated using fetal liver (FTL) cells derived from wild-type and Podxl−/− E15.5 embryos. Previously, it was shown that Podxl−/− mice die perinatally—likely due to a variety of non-hematopoietic defects (Doyonnas et al., 2001). However, Podxl−/− mice display normal fetal hematopoietic development and lethally-irradiated wild-type recipients transplanted with Podxl−/− bone marrow become fully-engrafted (>95% donor cells) and exhibit normal adult blood homeostasis (Doyonnas et al., 2001; Doyonnas et al., 2005). Finally, blood lineage analysis was performed by flow cytometry and methylcellulose colony-forming assays with Podxl−/− E15.5 fetal liver and no differences were detected in the balance of progenitors or lineages in the FTL, colony-forming cell plating efficiencies or, colony morphologies (Doyonnas et al., 2005).

Since mouse fetal liver at E15.5 primarily consists of definitive erythroblasts, in order to examine the migration of earlier progenitors, Ter119+ erythroid cells from wild-type and podocalyxin-deficient embryos were first depleted and then the migration of the remaining cells was assessed across fibronectin-coated transwells. As shown in FIG. 12, Podxl−/− fetal liver cells, like podocalyxin-deficient FDC-P1 cells, are impaired (53.5%±2.4) in their ability to migrate towards a SCF+CXCL12 gradient. Thus, podocalyxin enhances the migration of primary, definitive hematopoietic cells.

To test whether podocalyxin-dependent migration could be blocked at the protein level, assays were performed in the presence of a podocalyxin-specific monoclonal antibody. Similar to the results with shPodo cells, impaired chemotaxis of control FDC-P1 cells was observed when these were pre-treated with a podocalyxin-specific monoclonal antibody for 15 minutes prior to the migration assay (FIG. 11C). Turnover of antibody-bound podocalyxin on the cell surface is extremely slow and therefore it is likely that podocalyxin antibody serves to inhibit formation of either intracellular or extracellular protein complexes rather than leading to the internalization of podocalyxin ((Graf et al., 1992). Thus, podocalyxin expression is important for chemotactic migration and this can be inhibited by either blocking antibodies or inhibition of podocalyxin protein expression.

Podocalyxin Enhances Short-term Homing of Fetal Liver Cells to the Bone Marrow of Non-irradiated Recipients Previously, it has been noted that the podocalyxin-positive subset of bone marrow cells with a LSK surface phenotype were superior in long-term engraftment of lethally-irradiated primary and secondary recipients (Doyonnas et al., 2005). Despite this observation, however, it was found that podocalyxin wild-type and knockout fetal liver cells have similar capacities to reconstitute lethally-irradiated recipient mice in competitive hematopoietic stem cell transplantation assays, possibly due to functional compensation from CD34 and other related sialomucins (Doyonnas 2005).

Although these experiments did not reveal a significant difference in competitive longterm engraftment studies, the possibility remained that Podocalyxin deficient cells would have a more subtle deficiency in short term homing experiments. To test this possibility, Ter119-depleted fetal liver cells from wild-type and Podxl−/− embryos were labelled (Calcein AM) and transplanted into wild-type, non-irradiated cogeneic recipients and the frequency of donor cell homing to the bone marrow of recipients was monitored three hours later. Strikingly, it was found that Podxl−/− FTL were severely attenuated (approximately 60%) in their ability to home to bone marrow three hours after their injection into a tail-vein (FIG. 12). These results further support that podocalyxin enhances hematopoietic cell migration.

Podocalyxin Associates with CXCR4

Figure 13:
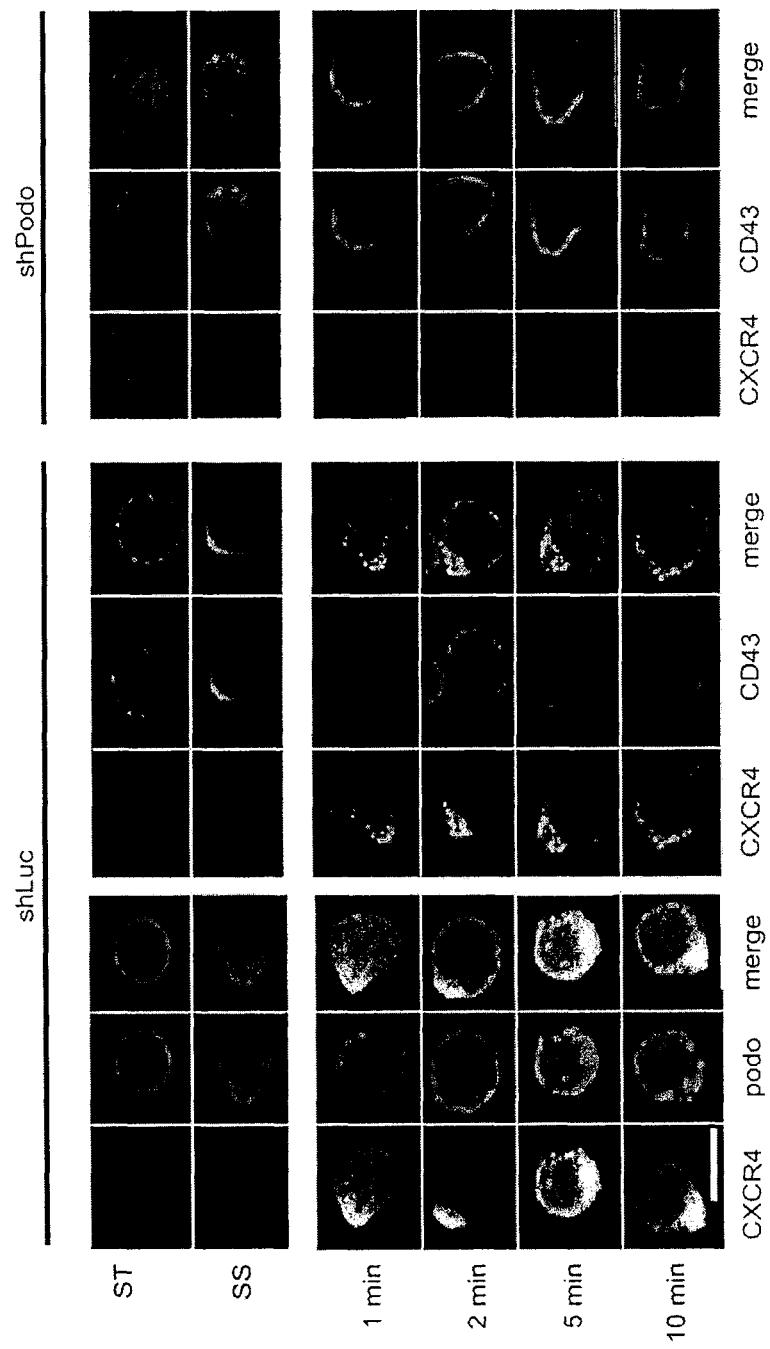
FIG. 13 shows podocalyxin and CXCR4 co-localize to a sub-cellular membrane compartment in response to SCF+CXCL12. Confocal microscope images (X-Y sections) of shLuc (left panels) and shPodo (right panels) infected FDC-P1 following IL-3-deprivation (ST, starved), during log-phase growth in IL-3 (SS, steady-state), or, cells starved and restimulated with SCF+CXCL12 for the times indicated (1 to 10 min). Cells are labeled with antibodies to CXCR4, podocalyxin, or isotype control antibody (as indicated for each column of images) and then detected using fluorochrome-labelled secondary antibodies. DAPI was used to stain the nucleus before mounting the cells on poly-L-lysine coated slides. The fluorescence intensities of the images shown were collected using a fixed detector voltage.

It has been demonstrated that sialomucins are capable of not only associating with chemokine receptors but that they can also modulate the activity of receptor signalling (Forde et al., 2007; Veerman et al., 2007). One possible mechanism by which podocalyxin could regulate CXCR4 signaling is by direct physical interaction of podocalyxin and CXCR4 at the cell membrane. To explore this possibility, confocal microscopy was used to determine if podocalyxin and CXCR4 colocalize to a subcellular compartment in FDC-P1 cells. Although surface expression of CXCR4 was not initially detected in log-phase FDC-P1 cells maintained in IL-3, or after IL-3-starvation (using an N-terminal domain specific CXCR4 antibody), rapid upregulation of the CXCR4 on the cell surface was found within one minute of stimulation with a SCF+CXCL12 cocktail (FIG. 13, left panel). This result likely reflects activation-mediated surface translocation of pre-formed intracellular receptor as has been reported previously (Schimanski et al., 2006). Although only minimal colocalization of CXCR4 with podocalyxin was detected at a membrane surface compartment initially, within two minutes of SCF+CXCL12 stimulation, CXCR4-podocalyxin co-localization was detectable at a polarized membrane compartment, peaking ten minutes after stimulation. As a testament to the specificity of the podocalyxin-CXCR4 interaction, colocalization of CXCR4 with CD43 (a distantly related cell surface sialomucin) could not be demonstrated in a similar experiment (FIG. 13).

To next test whether CXCR4 surface expression required the presence of podocalyxin, podocalyxin-deficient FDC-P1 cells were examined under the same experiment conditions (FIG. 13, right panel). In the absence of podocalyxin, extracellular surface expression of CXCR4 was undetectable following SCF+CXCL12 stimulation. Thus, the data suggest that podocalyxin plays an essential role in functional surface expression of CXCR4 in response to chemotactic or chemotactic-enhancing signals.

To further characterize the CXCR4-podocalyxin association, coimmunoprecipitation studies were performed (FIG. 14A). Consistent with the confocal microscopy experiments, it was found that, within one minute of stimulation, CXCR4 and podocalyxin began to form a complex that co-immunoprecipitates with anti-CXCR4. It was also found that the amount of podocalyxin associated with CXCR4 increases with time following SCF+CXCL12 stimulation. As expected, no such complex was observed with podocalyxin knockdown cells. Total (surface and intracellular) CXCR4 protein expression levels were comparable in both shLuc and shPodo-expressing cells (FIG. 14A; CXCR4 immunoblot) indicating an effect of Podocalyxin on the localization, but not the expression, of CXCR4.

Next, to explore the downstream consequences of podocalyxin-mediated CXCR4 signaling, the level of phospho-Akt (serine 473) in response to SCF+CXCL12 stimulation as a surrogate for Akt activity was compared. It was found that podocalyxin-deficient FDC-P1 displayed attenuated Akt-phosphorylation compared to control cells (FIG. 14B). In the context of the surface confocal findings, these data suggest that CXCR4 is maintained within an intracellular pool and that podocalyxin is required for maximal surface translocation or retention of a ligand-binding, functional CXCR4. These data suggest that, by influencing the localization of CXCR4, podocalyxin can affect the activation of downstream effectors of SCF+CXCL12-induced signaling.

Discussion

By using a lentiviral shRNA system to silence podocalyxin, its importance in adhesion to extracellular matrix components and homing of hematopoietic precursor lines in vitro and using primary Podxl−/− fetal liver cells, in a short-term homing assay, in vivo, was examined. Although the hypothesis was that loss of podocalyxin (a proposed anti-adhesin) would result in enhanced adhesion to matrix, no major alterations in adhesion were found in conditions that activated migration through a transwell towards a chemoattractant (SCF+CXCL12). One possibility is that podocalyxin's ability to block adhesion is linked to its translocation to specific plasma membrane sub-compartments. When overexpressed in epithelial lines, podocalyxin induces an apical domain expansion, leading to marginalization of cell-cell junctions and eventual delamination (Meder et al., 2005; Nielsen et al., 2007; Somasiri et al., 2004; Takeda et al., 2000; Yu et al., 2007). Thus, a block in adhesion may require abundant surface expression of podocalyxin and loss of basal membranes. Thus, deletion of podocalyxin in hematopoietic cells may only give a strong phenotype on resting hematopoietic cells where, for the most part, the cell surface exhibits a "pseudo-apical" membrane domain. Previously it was shown that IL-3 activation of FDC-P1 induces membrane polarization and rapid re-localization of podocalyxin (Tan et al., 2006) and, here in a similar polarization of podocalyxin in response to SCF+CXCL12 is demonstrated. It is possible that, under these circumstances, no major changes in activated cell adhesion are observed due to podocalyxin's natural tendency to be cleared from the adhesive, "basolateral-like" domains and redistributed to more "apical-like" domains.

Podocalyxin plays a clear role as a competence factor for the fidelity of chemotactic migration in response to CXCL12—this difference is enhanced in the presence of SCF as co-stimulant. Thus, shRNA deletion of podocalyxin in cell lines or targeted deletion in normal hematopoietic precursors leads to severely impaired chemotactic migration. With or without podocalyxin, a robust chemotactic response requires costimulation with SCF since CXCL12 alone produces a weak chemotactic response (across a stromal layer) in these cells. HSCs exposed for a very short time to SCF prior to transplantation into irradiated recipients engraft at a much higher frequency, and, c-kit and CXCR4 have been widely published to play important roles in the HSC homing to the bone marrow (Guo et al., 2007; Son et al., 2006; Yu et al., 2007). With regard to their synergy, previous literature has suggested that receptor tyrosine kinase ligation enhances the chemotaxis of both normal cells and tumors to CXCL12, likely due to de novo translocation of additional CXCR4 to the cell surface (Guo et al., 2007; Son et al., 2006). This may be particularly important for CXCR4-dependent chemotaxis since there is also evidence that cell surface CXCR4 is subject to inactivation via proteolytic cleavage of its amino-terminal, ligand-binding domain (Levesque et al., 2003). Thus, SCF may be required for stable surface expression of functional, non-cleaved, receptor.

There are several ways in which podocalyxin could facilitate SCF+CXCL12 synergistic homing. Since there were no differences in the total cellular levels of c-kit or CXCR4 expression in shPodo cells compared to control cells, the impaired migration is not the result of a lack of or decreased receptor expression (FIG. 10B (c-kit) and FIG. 14; immunoblot for CXCR4). The fact that upregulated expression of CXCR4 in the presence of SCF was not observed in podocalyxin-deficient cells suggest that it plays a role in either the surface transport, or the stable maintenance of CXCR4 on the plasma membrane. Finally, as discussed above, it has been shown that CXCR4 is subject to inactivation via amino-terminal proteolysis. It is therefore conceivable that podocalyxin, as a highly glycosylated mucin, may protect CXCR4 from proteolysis when they are colocalized to a subcellular membrane domain or even tightly associated in a complex. This is supported by evidence that immunoprecipitation of CXCR4 from whole cell lysates co-precipitates podocalyxin in SCF+CXCL12 stimulated but not non-stimulated cells. It is noted that c-kit was not detected in this complex and therefore likely exerts its effects on CXCR4 surface expression and cross-talk via intracellular signaling intermediates.

Finally, podocalyxin has recently been associated with an ever-widening array of epithelia tumors, (Casey et al., 2006; Heukamp et al., 2006; Ito et al., 2007; Ney et al., 2007; Schopperle et al., 2003; Sizemore et al., 2007; Somasiri et al., 2004) most of which exhibit an extremely poor disease outcome. In this regard, CXCL12 has also been shown to play an important role in the bone and peripheral metastasis of these tumors. Thus, podocalyxin upregulation on these tumors may enhance the acquisition of competence for CXCL12-dependent metastasis. Further, podocalyxin antibodies inhibit this behavior in vitro.

Although a difference between wild type and Podxl−/− fetal liver HSCs in the long term engraftment of lethally-irradiated recipients was not detected, a deficit in short term homing was observed. Similar transplant experiments with Cxcr4−/− (ubiquitous knock-out) fetal liver demonstrated a more modest defect in long-term reconstitution and HSC maintenance (Kawabata et al., 1999; Ma et al., 1999) compared to the observed depletion of HSC pools following induced deletion of Cxcr4−/− in adult mice (Sugiyama et al., 2006). Although other interpretations are possible, the results showing that Ter119-negative fetal liver cells display defective short-term homing to the bone marrow indicate that podocalyxin expression may enhance homing or retention of hematopoietic cells in the marrow.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Tissue Microarray Population Characteristics

Lymph node status:

| | | |
|---|---|---|
| Negative | 160 | (66.9%) |
| Positive | 79 | (29.3%) |
| Unknown | 31 | (11.5%) |

Tumor grade:

| | | |
|---|---|---|
| 1 | 55 | (20.4%) |
| 2 | 148 | (54.8%) |
| 3 | 67 | (24.8%) |

Tumor Size

| | | |
|---|---|---|
| <10 mm | 20 | (7.4%) |
| 10 mm-20 mm | 43 | (15.9%) |
| >20 mm | 72 | (26.7%) |
| Unknown | 135 | (50%) |

Overall Survival

| | |
|---|---|
| Mean | 14.9 years |
| Median | 15.0 years |

TABLE 2

Cox Regression Multi-Variant Analysis

| Marker | Degree of Freedom | Significance (p)* | Relative Risk (RR) | 95% Confidence Interval for RR Lower | 95% Confidence Interval for RR Upper |
|---|---|---|---|---|---|
| Podocalyxin | 1 | 0.006 | 7.271 | 1.747 | 30.255 |
| P53 | 1 | 0.121 | 2.794 | 0.764 | 10.222 |
| ER** | 1 | 0.541 | 0.866 | 0.547 | 01.372 |
| HER2 | 1 | 0.008 | 4.661 | 1.485 | 14.624 |
| Nodes | 1 | 0.003 | 3.688 | 1.581 | 08.601 |
| Grade | 2 | 0.257 | 3.088 | 0.798 | 11.946 |
| Tumor Size | 2 | 0.482 | 1.115 | 0.475 | 02.620 |

*Correlation is significant at the 0.05 level.
**PR gives the same result.

TABLE 3

Pearson Correlation Analysis Between Podocalyxin and Other Known Clinicohistopathological Markers.

| Marker | Pearson Correlation | Significance | Number of Cases |
|---|---|---|---|
| Podocalyxin | 1.0 | — | 270 |
| p53 | 0.180 | 0.006 | 236 |
| ER | −0.214 | 0.001 | 240 |
| HER2 | −0.032 | 0.613 | 258 |
| Nodes | −0.069 | 0.285 | 239 |
| Grade | 0.191 | 0.002 | 270 |

TABLE 4

Tissue Distribution of CD34 Family Members

| | Cells | | |
|---|---|---|---|
| Tissue | Endoglycan | Podocalyxin | CD34 |
| Multipotent hematopoetic precursors | | | |
| Adult | + | + | + |
| Embryo | + | + | + |
| Monopotent precursors | | | |
| Erythroid | + | + | − |
| Thrombocytic | ? | + | + |
| Myeloid | +/− | − | + |
| Lymphoid (subset of thymocytes) | +? | + | + |
| Mature hematopoetic cells | | | |
| B Cells (LPS activated) | + | − | − |
| T Cells | − | − | − |
| Macrophages | − | − | − |
| Granulocytes | − | − | − |
| Eosinophils | − | − | − |
| Mast Cells | − | − | + |
| Erythrocytes | +* | +* | − |
| Platelets | ? | + | − |
| Vessels | | | |
| Vascular endothelial | − | + | + |
| Vascular smooth muscle | + | − | − |
| Intestinal Epithelial | + | − | − |
| Podocytes | +/− | + | − |
| Brain (Neurons) | + | +** | ? |
| Boundary Elements(mesothelial) | − | + | − |

*embryonic erythrocytes only
**ependymal layer only

Full Citations for References Referred to in the Specification

Acs, G., Lawton, T. J., Rebbeck, T. R., LiVolsi, V. A., Zhang, P. J. Differential expression of E-cadherin in lobular and ductal neoplasms of the breast and its biologic and diagnostic implications. Am J Clin Pathol. 2001 January; 115 (1):85-98.

Adams, G. B., Chabner, K. T., Alley, I. R., Olson, D. P., Szczepiorkowski, Z. M., Poznansky, M. C., Kos, C. H., Pollak, M. R., Brown, E. M. and Scadden, D. T. (2006). Stem cell engraftment at the endosteal niche is specified by the calcium-sensing receptor. Nature 439, 599-603.

Adeyinka A., Emberley E., Niu Y., Snell L., Murphy L. C., Sowter H., Wykoff C. C., Harris A. L., Watson P. H. (2002) Analysis of gene expression in ductal carcinoma in situ of the breast. Clin. Cancer Res. 8(12):3788-95.

Aiuti, A., Turchetto, L., Cota, M., Cipponi, A., Brambilla, A., Arcelloni, C., Paroni, R., Vicenzi, E., Bordignon, C. and Poli, G. (1999). Human CD34(+) cells express CXCR4 and its ligand stromal cell-derived factor-1. implications for infection by T-cell tropic human immunodeficiency virus. Blood 94, 62-73.

Aiuti, A., Webb, I. J., Bleul, C., Springer, T. and Gutierrez-Ramos, J. C. (1997). The chemokine SDF-1 is a chemoattractant for human CD34+ hematopoietic progenitor cells and provides a new mechanism to explain the mobilization of CD34+ progenitors to peripheral blood. Journal of Experimental Medicine 185, 111-20.

Alderuccio, F., Siatskas, C., Chan, J., Field, J., Murphy, K., Nasa, Z. and Toh, B. H. (2006). Haematopoietic stem cell gene therapy to treat autoimmune disease. Curr. Stem Cell. Res. Ther. 1, 279-287.

Aubele, M., Mattis, A., Zitzelsberger, H., Walch, A., Kremer, M., Welzl, G., Hofler, H., and Werner M. (2000). Extensive ductal carcinoma In situ with small foci of invasive ductal carcinoma: evidence of genetic resemblance by CGH. Int J Cancer. 85, 82-86.

Barrett, A. J. and Savani, B. N. (2008). Allogeneic stem cell transplantation for myelodysplastic syndrome. Semin. Hematol. 45, 49-59.

Baumhueter, S., Singer, M. S., Henzel, W., Hemmerich, S., Renz, M., Rosen, S. D., Lasky, L. A. (1993) Binding of L-selectin to the vascular sialomucin CD34. Science 262, 436-8

Berx, G., and Van Roy, F. (2001). The E-cadherin/catenin complex: an important gatekeeper in breast cancer tumorigenesis and malignant progression. Breast Cancer Res. 3, 289-293.

Bistrup, A., Bhakta, S., Lee, J. K., Belov, Y. Y., Gunn, M. D., Zuo, F. R., Huang, C. C., Kannagi, R., Rosen, S. D., and Hemmerich, S. (1999). Sulfotransferases of two specificities function in the reconstitution of high endothelial cell ligands for L-selectin. J. Cell Biol. 145, 899-910.

Blanchet, M. R., Maltby, S., Haddon, D. J., Merkens, H., Zbytnuik, L. and McNagny, K. M. (2007). CD34 facilitates the development of allergic asthma. Blood 110, 2005-2012.

Blechman, J. M., Lev, S., Givol, D. and Yarden, Y. (1993). Structure-function analyses of the kit receptor for the steel factor. Stem Cells 11 Suppl 2, 12-21.

Blechman, J. M. and Yarden, Y. (1995). Structural aspects of receptor dimerization. c-kit as an example. Ann N Y Acad Sci 766, 344-62.

Bos R., van der Groep P., Greijer A. E., Shvarts A., Meijer S., Pinedo H. M., Semenza G. L., van Diest P. J., van der Wall E. (2003) Levels of hypoxia-inducible factor-1alpha independently predict prognosis in patients with lymph node negative breast carcinoma. Cancer 97(6):1573-81.

Broudy, V. C. (1997). Stem cell factor and hematopoiesis. Blood 90, 1345-64.

Broxmeyer, H. E. (2008). Chemokines in hematopoiesis. Curr. Opin. Hematol. 15, 49-58.

Burger, J. A. and Burkle, A. (2007). The CXCR4 chemokine receptor in acute and chronic leukaemia: A marrow homing receptor and potential therapeutic target. Br. J. Haematol. 137, 288-296.

Burger, J. A. and Kipps, T. J. (2006). CXCR4: A key receptor in the crosstalk between tumor cells and their microenvironment. Blood 107, 1761-1767.

Campbell, T. B. and Broxmeyer, H. E. (2008). CD26 inhibition and hematopoiesis: A novel approach to enhance transplantation. Front. Biosci. 13, 1795-1805.

Cancelas, J. A., Jansen, M. and Williams, D. A. (2006). The role of chemokine activation of rac GTPases in hematopoietic stem cell marrow homing, retention, and peripheral mobilization. Exp. Hematol. 34, 976-985.

Cano, A., Perez-Moreno, M. A., Rodrigo, I., Locascio, A., Blanco, M. J., del Barrio, M. G., Portillo, F., Nieto, M. A. The transcription factor snail controls epithelial-mesenchymal transitions by repressing E-cadherin expression. Nat Cell Biol. 2000 February; 2(2):76-83.

Casey, G., Neville, P. J., Liu, X., Plummer, S. J., Cicek, M. S., Krumroy, L. M., Curran, A. P., McGreevy, M. R., Catalona, W. J., Klein, E. A. et al. (2006). Podocalyxin variants and risk of prostate cancer and tumor aggressiveness. Hum. Mol. Genet. 15, 735-741.

Cheshier, S. H., Morrison, S. J., Liao, X. and Weissman, I. L. (1999). In vivo proliferation and cell cycle kinetics of long-term self-renewing hematopoietic stem cells. Proc. Natl. Acad. Sci. U.S.A. 96, 3120-3125.

Cleton-Jansen, A. M. (2002). E-cadherin and loss of heterozygosity at chromosome 16 in breast carcinogenesis: different genetic pathways in ductal and lobular breast cancer? Breast Cancer Res. 4, 5-8.

Dekan, G., Gabel, C. and Farquhar, M. G. (1991). Sulfate contributes to the negative charge of podocalyxin, the major sialoglycoprotein of the glomerular filtration slits. Proc Natl Acad Sci USA 88, 5398-402.

Dexter, T. M., Garland, J., Scott, D., Scolnick, E. and Metcalf, D. (1980). Growth of factor-dependent hemopoietic precursor cell lines. J. Exp. Med. 152, 1036-1047.

Diaz, L. K., Wiley, E. L., Morrow, M. Expression of epithelial mucins Muc1, Muc2, and Muc3 in ductal carcinoma in situ of the breast. Breast J. 2001 January-February; 7(1):40-5.

Doyonnas, R., Kershaw, D. B., Duhme, C., Merkens, H., Chelliah, S., Graf, T. and McNagny, K. M. (2001). Anuria, omphalocele, and perinatal lethality in mice lacking the CD-34-related protein Podocalyxin. J Exp Med, 194:13-27.

Doyonnas, R., Nielsen, J. S., Chelliah, S., Drew, E., Hara, H., Miyajima, A. and McNagny, K. M. (2005). Podocalyxin is a CD34-related marker of murine hematopoietic stem cells and embryonic erythroid cells. Blood 105, 4170-4178.

Drew, E., Merkens, H., Chelliah, S., Doyonnas, R. and McNagny, K. (2002). CD34 is a specific marker of mature murine mast cells. Exp Hematol 30, 1211.

Drew, E., Merzaban, J. S., Seo, W., Ziltener, H. J. and McNagny, K. M. (2005). CD34 and CD43 inhibit mast cell adhesion and are required for optimal mast cell reconstitution. Immunity 22, 43-57.

Driessen, R. L., Johnston, H. M. and Nilsson, S. K. (2003). Membrane-bound stem cell factor is a key regulator in the initial lodgment of stem cells within the endosteal marrow region. Exp Hematol 31, 1284-91.

Dvorak, C. C. and Cowan, M. J. (2008). Hematopoietic stem cell transplantation for primary immunodeficiency disease. Bone Marrow Transplant. 41, 119-126.

Elston, C. W. and Ellis, I. O. (1991). Pathological prognostic factors in breast cancer. I. the value of histological grade in breast cancer: experience from a large study with long-term follow-up. Histopathology 19, 403-410.

Engstrom, M., Karlsson, R. and Jonsson, J. I. (2003). Inactivation of the forkhead transcription factor FoxO3 is essential for PKB-mediated survival of hematopoietic progenitor cells by kit ligand. Exp. Hematol. 31, 316-323.

Fackler M. J., Krause D. S., Smith O. M., Civin C. I., May W. S. (1995) Full-length but not truncated CD34 inhibits hematopoietic cell differentiation of M1 cells. Blood 85(11):3040-7.

Fieger, C. B., Sassetti, C. M., and Rosen, S. D. (2003) Endoglycan, a Member of the CD34 Family, Functions as an L-selectin Ligand through Modification with Tyrosine Sulfation and Sialyl Lewis X. J. Biol. Chem. 278(30), 27390-27398.

Forde, S., Tye, B. J., Newey, S. E., Roubelakis, M., Smythe, J., McGuckin, C. P., Pettengell, R. and Watt, S. M. (2007). Endolyn (CD164) modulates the CXCL12-mediated migration of umbilical cord blood CD133+ cells. Blood 109, 1825-33.

Furness, S. G. and McNagny, K. (2006). Beyond mere markers: Functions for CD34 family of sialomucins in hematopoiesis. Immunol Res 34, 13-32.

Gillett, C. E., Miles, D. W., Ryder, K., Skilton, D., Liebman, R. D., Springall, R. J., Barnes, D. M., Hanby, A. M. (2001). Retention of the expression of E-cadherin and catenins is associated with shorter survival in grade III ductal carcinoma of the breast. J Pathol, 193:433-441.

Glodek, A. M., Le, Y., Dykxhoorn, D. M., Park, S. Y., Mostoslaysky, G., Mulligan, R., Lieberman, J., Beggs, H. E., Honczarenko, M. and Silberstein, L. E. (2007). Focal adhesion kinase is required for CXCL12-induced chemotactic and pro-adhesive responses in hematopoietic precursor cells. Leukemia 21, 1723-1732.

Gluckman, E. and Wagner, J. E. (2008). Hematopoietic stem cell transplantation in childhood inherited bone marrow failure syndrome. Bone Marrow Transplant. 41, 127-132.

Graf, T., McNagny, K., Brady, G. and Frampton, J. (1992). Chicken "erythroid" cells transformed by the gag-myb-ets-encoding E26 leukemia virus are multipotent. Cell 70, 201-13.

Guaita, S., Puig, I., Franci, C., Gamido, M., Dominguez, D., Bathe, E., Sancho, E., Dedhar, S., De Herreros, A. G., Baulida, J. Snail induction of epithelial to mesenchymal transition in tumor cells is accompanied by MUC1 repression and ZEB1 expression. J Biol Chem. 2002 Oct. 18; 277(42):39209-16. Epub 2002 Aug. 2.

Guo, Z., Cai, S., Fang, R., Chen, H., Du, J., Tan, Y., Ma, W., Hu, H., Cai, S, and Liu, Y. (2007). The synergistic effects of CXCR4 and EGFR on promoting EGF-mediated metastasis in ovarian cancer cells. Colloids Surf B Biointerfaces 60, 1-6.

Hart, C., Drewel, D., Mueller, G., Grassinger, J., Zaiss, M., Kunz-Schughart, L. A., Andreesen, R., Reichle, A., Holler, E. and Hennemann, B. (2004). Expression and function of homing-essential molecules and enhanced in vivo homing ability of human peripheral blood-derived hematopoietic progenitor cells after stimulation with stem cell factor. Stem Cells 22, 580-9.

Hartmann, T. N., Burger, J. A., Glodek, A., Fujii, N. and Burger, M. (2005). CXCR4 chemokine receptor and integrin signaling co-operate in mediating adhesion and chemoresistance in small cell lung cancer (SCLC) cells. Oncogene 24, 4462-71.

Helczynska K., Kronblad A., Jogi A., Nilsson E., Beckman S., Landberg G., Pahlman S. (2003) Hypoxia promotes a dedifferentiated phenotype in ductal breast carcinoma in situ. Cancer Res. 63(7):1441-4.

Heukamp, L. C., Fischer, H. P., Schirmacher, P., Chen, X., Breuhahn, K., Nicolay, C., Buttner, R. and Gutgemann, I. (2006). Podocalyxin-like protein 1 expression in primary hepatic tumours and tumour-like lesions. Histopathology 49, 242-7.

Hiraoka, N., Petryniak, B., Nakayama, J., Tsuboi, S., Suzuki, M., Yeh, J. C., Izawa, D., Tanaka, T., Miyasaka, M., Lowe, J. B. et al. (1999). A novel, high endothelial venule-specific sulfotransferase expresses 6-sulfo sialyl lewis(x), an L-selectin ligand displayed by CD34. Immunity 11, 79-89.

Hoover, K. B., Liao, S.-Y., and Bryant, P. J. (1997). Loss of tight junction MAGUK ZO-1 in breast cancer. Am. J. Pathol. 153, 1767-1773.

Horvat, R., Hovorka, A., Dekan, G., Poczewski, H. and Kerjaschki, D. (1986). Endothelial cell membranes contain podocalyxin—the major sialoprotein of visceral glomerular epithelial cells. J Cell Biol 102, 484-91.

Ito, T., Maki, N., Hazeki, O., Sasaki, K. and Nekooki, M. (2007). Extracellular and transmembrane region of a podocalyxin-like protein 1 fragment identified from colon cancer cell lines. Cell Biol Int 31, 1518-24.

Kaplan, R. N., Psaila, B. and Lyden, D. (2007). Niche-to-niche migration of bone marrow-derived cells. Trends in Molecular Medicine 13, 72-81.

Kapur, R., Cooper, R., Zhang, L. and Williams, D. A. (2001). Cross-talk between alpha(4)beta(1)/alpha(5)beta(1) and c-kit results in opposing effect on growth and survival of hematopoietic cells via the activation of focal adhesion kinase, mitogenactivated protein kinase, and akt signaling pathways. Blood 97, 1975-1981.

Kawabata, K., Ujikawa, M., Egawa, T., Kawamoto, H., Tachibana, K., Iizasa, H., Katsura, Y., Kishimoto, T. and Nagasawa, T. (1999). A cell-autonomous requirement for CXCR4 in long-term lymphoid and myeloid reconstitution. Proc. Natl. Acad. Sci. U.S.A. 96, 5663-5667.

Kerjaschki, D., Sharkey, D. J., and Farquhar, M. G. (1984) Identification and characterization of podocalyxin—the major sialoprotein of the renal glomerular epithelial cell. J. Cell Biol. 98, 1591-1596.

Kershaw, D. B., Thomas, P. E., Wharram, B. L., Goyal, M., Wiggins, J. E., Whiteside, C. I., and Wiggins, R. C. (1995). Molecular cloning, expression, and characterization of podocalyxin-like protein 1 from rabbit as a transmembrane protein of glomerular podocytes and vascular endothelium. J. Biol. Chem. 270, 29439-29446.

Kershaw, D. B., Beck, S. G., Wharram, B. L., Wiggins, J. E., Goyal, M., Thomas, P. E., and Wiggins, R. C. (1997a) Molecular cloning and characterization of human podocalyxin-like protein. J. Biol. Chem. 272, 15708-15714.

Kershaw, D. B., Wiggins, J. E., Wharram, B. L., and Wiggins, R. C. (1997) Assignment of the human podocalyxin-like protein (PODXL) gene to 7g32-q33. Genomics 45, 239-240.

Knowles, H. J., and Harris, A. L. (2001) Hypoxia and oxidative stress in breast cancer. Hypoxia and tumorigenesis. Breast Cancer Res. 3, 318-322.

Kominsky, S. L., Argani, P., Korz, D., Everon, E., Raman, V., Garrett, E., Rein, A., Sauter, G., Kallioniemi, O.-P., and Sukumar, S. (2003). Loss of the tight junction protein claudin-7 correlates with histological grade in both ductal carcinoma in situ and invasive ductal carcinoma of the breast. Oncogene 22, 2021-2033.

Kononen, J., Bubendorf, L., Kallioniemi, A., Barlund, M., Schraml, P., Leighton, S., Torhorst, J., Mihatsch, M. J., Sauter, G., and Kallioniemi, O. P. (1998). Tissue microarrays for high-throughput molecular profiling of tumor specimens. Nat Med. 4, 844-7.

Kramer, F., White, K., Kubbies, M., Swisshelm, K. and Weber, B. H. F. (2000). Genomic organization of claudin-1 and its assessment in hereditary and sporadic breast cancer. Hum Genet. 107, 249-256.

Krause, D. S., Fackler, M. J., Civin, C. I., and May, W. S. (1996) CD34: structure, biology and clinical utility. Blood 87(1):1-13.

Laird, D. J., von Andrian, U. H. and Wagers, A. J. (2008). Stem cell trafficking in tissue development, growth, and disease. Cell 132, 612-630.

Lanza F., Healy L., Sutherland D. R. (2001) Structural and functional features of the CD34 antigen: an update. J. Biol. Regul. Homeost. Agents 15(1):1-13.

Lapidot, T. and Kollet, O. (2002). The essential roles of the chemokine SDF-1 and its receptor CXCR4 in human stem cell homing and repopulation of transplanted immunodeficient NOD/SCID and NOD/SCID/B2m(null) mice. Leukemia 16, 1992-2003.

Lee, Y., Gotoh, A., Kwon, H. J., You, M., Kohli, L., Mantel, C., Cooper, S., Hangoc, G., Miyazawa, K., Ohyashiki, K. et al. (2002). Enhancement of intracellular signalling associated with hematopoietic progenitor cell survival in response to SDF-1/CXCL12 in synergy with other cytokines. Blood 99, 4307-4317.

Levesque, J. P., Hendy, J., Takamatsu, Y., Simmons, P. J. and Bendall, L. J. (2003). Disruption of the CXCR4/CXCL12 chemotactic interaction during hematopoietic stem cell mobilization induced by GCSF or cyclophosphamide. J Clin Invest 111, 187-96.

Li, Y., Li, J. Straight S W, Kershaw D B. PDZ domain-mediated interaction of rabbit podocalyxin and Na(+)/H(+) exchange regulatory factor-2. Am J Physiol Renal Physiol. 2002 June; 282(6):F1129-39.

Liu, C. L., Prapong, W., Natkuman, Y., Alizadeh, A., Montgomery, K., Gilks, C. B., van de Rijn, M. (2002). Software tools for high-throughput analysis and archiving of immunohistochemistry staining data obtained with tissue microarrays. Am. J. Pathol. 161, 1557-1564.

Ma, Q., Jones, D. and Springer, T. A. (1999). The chemokine receptor CXCR4 is required for the retention of B lineage and granulocytic precursors within the bone marrow microenvironment. Immunity 10, 463-471.

Makretsov, N., Gilks, B., Goldman, A., Hayes, M., and Huntsman, D. (2003). tissue microarray analysis of neuroendocrine differentiation and its prognostic significance in breast cancer. In Press.

McGuckin, M. A., Walsh, M. D., Hohn, B. G., Ward, B. G., Wright, R. G. Prognostic significance of MUC1 epithelial mucin expression in breast cancer. Hum Pathol. 1995 April; 26(4):432-9.

McNagny, K. M., Pettersson, I., Rossi, F., Flamme, I., Shevchenko, A., Mann, M., and Graf, T. (1997). Thrombomucin, a novel cell surface protein that defines thrombocytes and multipotent hematopoietic progenitors. J. Cell Biol. 138, 1395-1407.

Meder, D., Shevchenko, A., Simons, K. and Fullekrug, J. (2005). Gp135/podocalyxin and NHERF-2 participate in the formation of a preapical domain during polarization of MDCK cells. J Cell Biol 168, 303-13.

Mehta, P. A. and Davies, S. M. (2008). Allogeneic transplantation for childhood ALL. Bone Marrow Transplant. 41, 133-139.

Miettinen, A., Solin, M. L., Reivinen, J., Juvonen, E., Vaisanen, R. and Holthofer, H. (1999). Podocalyxin in rat platelets and megakaryocytes. Am. J. Pathol. 154, 813-822.

Mommers, E. C., Leonhart, A. M., von Mensdorff-Pouilly, S., Schol, D. J., Hilgers, J., Meijer, C. J., Baak, J. P., van Diest, P. J. Aberrant expression of MUC1 mucin in ductal hyperplasia and ductal carcinoma in situ of the breast. Int J Cancer. 1999 Oct. 22; 84(5):466-9.

Nabholtz, J. M., and Slamon, D. (2001). New adjuvant strategies for breast cancer: meeting the challenge of integrating chemotherapy and trastuzumab (Herceptin). Semin. Oncol. 28, 1-12.

Nervi, B., Link, D. C. and DiPersio, J. F. (2006). Cytokines and hematopoietic stem cell mobilization. Journal of Cellular Biochemistry 99, 690-705.

Ney, J. T., Zhou, H., Sipos, B., Buttner, R., Chen, X., Kloppel, G. and Gutgemann, I. (2007). Podocalyxin-like protein 1 expression is useful to differentiate pancreatic ductal adenocarcinomas from adenocarcinomas of the biliary and gastrointestinal tracts. Hum Pathol 38, 359-64.

Nielsen, J. S, and McNagny, K. M. (2007). Influence of host irradiation on long-term engraftment by CD34-deficient hematopoietic stem cells. Blood 110, 1076-7.

Palmer, R. E., Kotsianti, A., Cadman, B., Boyd, T., Gerald, W., Haber, D. A. (2001) WT1 regulates the expression of the major glomerular podocyte membrane protein Podocalyxin. Curr Biol. 11, 1805-1809.

Page, D. L. and Simpson, J. F. Pathology of preinvasive and excellent-prognosis breast cancer. Curr Opin Oncol. 2000 November; 12(6):526-31.

Papayannopoulou, T. and Craddock, C. (1997). Homing and trafficking of hemopoietic progenitor cells. Acta Haematol 97, 97-104.

Papayannopoulou, T. and Nakamoto, B. (1993). Peripheralization of hemopoietic progenitors in primates treated with anti-VLA4 integrin. Proc Natl Acad Sci USA 90, 9374-8.

Parker, R. L., Huntsman, D. G., Lesack, D. W., Cupples, J. B., Grant, D. R., Akbari, M. and Gilks, C. B. (2002). Assessment of interlaboratory variation in the immunohistochemical determination of estrogen receptor status using a breast cancer tissue microarray. Am J Clin Pathol 117, 723-728.

Pelus, L. M. and Fukuda, S. (2008). Chemokine-mobilized adult stem cells; defining a better hematopoietic graft. Leukemia 22, 466-473.

Perez-Albuerne, E. D., Eapen, M., Klein, J., Gross, T. J., Lipton, J. M., Baker, K. S., Woolfrey, A. and Kamani, N. (2008). Outcome of unrelated donor stem cell transplantation for children with severe aplastic anemia. Br. J. Haematol. 141, 216-223.

Pinto, F. O. and Roberts, I. (2008). Cord blood stem cell transplantation for haemoglobinopathies. Br. J. Haematol. 141, 309-324.

Prasad, V. K. and Kurtzberg, J. (2008). Emerging trends in transplantation of inherited metabolic diseases. Bone Marrow Transplant. 41, 99-108.

Puri, K. D., Finger, E. B., Gaudernack, G. and Springer, T. A. (1995). Sialomucin CD34 is the major L-selectin ligand in human tonsil high endothelial venules. J. Cell Biol. 131, 261-270.

Rahn, J. J., Dabbagh, L., Pasdar, M., Hugh, J. C. The importance of MUC1 cellular localization in patients with breast carcinoma: an immunohistologic study of 71 patients and review of the literature. Cancer. 2001 Jun. 1; 91(11):1973-82.

Roskelley, C. D., and Bissell, M. J. (2002). The dominance of the microenvironment in breast and ovarian cancer. Semin. Cancer Biol. 12, 97-104.

Rubinson, D. A., Dillon, C. P., Kwiatkowski, A. V., Sievers, C., Yang, L., Kopinja, J., Rooney, D. L., Zhang, M., Ihrig, M. M., McManus, M. T. et al. (2003). A lentivirus-based system to functionally silence genes in primary mammalian cells, stem cells and transgenic mice by RNA interference. [erratum appears in nat genet. 2003 jun; 34(2):231 note: Zhang, mingdi [added]]. Nature Genetics 33, 401-6.

Sassetti, C., Tangemann, K., Singer, M. S., Kershaw, D. B. and Rosen, S. D. (1998b). Identification of podocalyxin-like protein as a high endothelial venule ligand for L-selectin: Parallels to CD34. J. Exp. Med. 187, 1965-1975.

Sassetti, C., Van Zante, A., and Rosen, S. D. (2000) Identification of Endoglycan, a Member of the CD34/Podocalyxin Family of Sialomucins. J. Biol. Chem. 275(12), 9001-9010.

Sathyanarayana, P., Menon, M. P., Bogacheva, O., Bogachev, O., Niss, K., Kapelle, W. S., Houde, E., Fang, J. and Wojchowski, D. M. (2007). Erythropoietin modulation of podocalyxin, and a proposed erythroblast niche. Blood.

Satomaa T, Renkonen O, Helin J, Kirveskari J, Makitie A, Renkonen R. (2002) O-glycans on human high endothelial CD34 putatively participating in L-selectin recognition. Blood 99(7):2609-11.

Scadden, D. T. (2006). The stem-cell niche as an entity of action. Nature 441, 1075-1079.

Schimanski, C. C., Bahre, R., Gockel, I., Muller, A., Frerichs, K., Horner, V., Teufel, A., Simiantonaki, N., Biesterfeld, S., Wehler, T. et al. (2006). Dissemination of hepatocellular carcinoma is mediated via chemokine receptor CXCR4. Br J Cancer 95, 210-7.

Schopperle, W. M., Kershaw, D. B., and DeWolf, W. C. (2002). Human embryonal carcinoma antigen, Gp200/GCTM-2 is podocalyxin. Biochem Biophys. Res. Comm. 300, 285-290.

Shenoy, S, and Smith, F. O. (2008). Hematopoietic stem cell transplantation for childhood malignancies of myeloid origin. Bone Marrow Transplant. 41, 141-148.

Sierra, J., Martino, R., Sanchez, B., Pinana, J. L., Valcarcel, D. and Brunet, S. (2008). Hematopoietic transplantation from adult unrelated donors as treatment for acute myeloid leukemia. Bone Marrow Transplant. 41, 425-437.

Sizemore, S., Cicek, M., Sizemore, N., Ng, K. P. and Casey, G. (2007). Podocalyxin increases the aggressive phenotype of breast and prostate cancer cells in vitro through its interaction with ezrin. Cancer Res. 67, 6183-6191.

Somasiri, A., Nielsen, J. S., Makretsov, N., McCoy, M. L., Prentice, L., Gilks, C. B., Chia, S. K., Gelmon, K. A., Kershaw, D. B., Huntsman, D. G. et al. (2004). Overexpression of the anti-adhesin podocalyxin is an independent predictor of breast cancer progression. Cancer Res 64, 5068-73.

Son, B. R., Marquez-Curtis, L. A., Kucia, M., Wysoczynski, M., Turner, A. R., Ratajczak, J., Ratajczak, M. Z. and Janowska-Wieczorek, A. (2006). Migration of bone marrow and cord blood mesenchymal stem cells in vitro is regulated by stromal-derived factor-1-CXCR4 and hepatocyte growth factor-c-met axes and involves matrix metalloproteinases. Stem Cells 24, 1254-64.

Stein, A. and Forman, S. J. (2008). Allogeneic transplantation for ALL in adults. Bone Marrow Transplant. 41, 439-446.

Sugiyama, T., Kohara, H., Noda, M. and Nagasawa, T. (2006). Maintenance of the hematopoietic stem cell pool by CXCL12-CXCR4 chemokine signaling in bone marrow stromal cell niches. Immunity 25, 977-988.

Takeda, T., Go, W. Y., Orlando, R. A., and Farquhar, M. G. (2000). Expression of podocalyxin inhibits cell-cell adhesion and modifies junctional properties in Madin-Darby Canine Kidney Cells. Mol. Biol. Cell 11, 3219-3232.

Takeda, T., McQuistran, T., Orlando, R. A., and Farquhar, M. G. (2001). Loss of glomerular foot processes is associated with uncoupling of podocalyxin from the actin cytoskeleton. J. Clin. Invest. 108, 289-301.

Tan, P. C., Furness, S. G., Merkens, H., Lin, S., McCoy, M. L., Roskelley, C. D., Kast, J. and McNagny, K. M. (2006). Na+/H+ exchanger regulatory factor-1 is a hematopoietic ligand for a subset of the CD34 family of stem cell surface proteins. Stem Cells 24, 1150-61.

Tavor, S., Petit, I., Porozov, S., Avigdor, A., Dar, A., Leider-Trejo, L., Shemtov, N., Deutsch, V., Naparstek, E., Nagler, A. et al. (2004). CXCR4 regulates migration and development of human acute myelogenous leukemia stem cells in transplanted NOD/SCID mice. Cancer Res 64, 2817-24.

THOMAS, E. D., LOCHTE, H. L., Jr, LU, W. C. and FERREBEE, J. W. (1957). Intravenous infusion of bone marrow in patients receiving radiation and chemotherapy. N. Engl. J. Med. 257, 491-496.

Tse, W. W., Zang, S. L., Bunting, K. D. and Laughlin, M. J. (2008). Umbilical cord blood transplantation in adult myeloid leukemia. Bone Marrow Transplant. 41, 465-472.

Ullah, K., Khan, B., Raza, S., Ahmed, P., Satti, T. M., Butt, T., Tariq, W. Z. and Kamal, M. K. (2008). Bone marrow transplant cure for beta-thalassaemia major: Initial experience from a developing country. Ann. Hematol. 87, 655-661.

Veerman, K. M., Williams, M. J., Uchimura, K., Singer, M. S., Merzaban, J. S., Naus, S., Carlow, D. A., Owen, P., Rivera-Nieves, J., Rosen, S. D. et al. (2007). Interaction of the selectin ligand PSGL-1 with chemokines CCL21 and CCL19 facilitates efficient homing of T cells to secondary lymphoid organs. Nat Immunol 8, 532-9.

Weissman, I. L. (1996). From thymic lineages back to hematopoietic stem cells, sometimes using homing receptors. J Immunol 156, 2019-25.

Whetton, A. D. and Graham, G. J. (1999). Homing and mobilization in the stem cell niche. Trends in Cell Biology 9, 233-8.

Williams, D. A., Rios, M., Stephens, C. and Patel, V. P. (1991). Fibronectin and VLA-4 in haematopoietic stem cell-microenvironment interactions. Nature 352, 438-41.

Williams, D. A., Zheng, Y. and Cancelas, J. A. (2008). Rho GTPases and regulation of hematopoietic stem cell localization. Methods Enzymol. 439, 365-393.

Yu, C. Y., Chen, J. Y., Lin, Y. Y., Shen, K. F., Lin, W. L., Chien, C. L., ter Beest, M. B. and Jou, T. S. (2007). A bipartite signal regulates the faithful delivery of apical domain marker podocalyxin/Gp135. Mol Biol Cell 18, 1710-22.

---

We claim:

1. A method of inhibiting cancer metastasis or treating cancer having a poor outcome comprising:
   (i) obtaining a sample from an animal;
   (ii) measuring the expression level of podocalyxin peptide in said sample;
   (iii) comparing the expression level of (ii) to a control,
   (iv) identifying the animal as having, or having a risk of metastatic cancer or cancer having a poor outcome if the animal overexpresses the podocalyxin polypeptide compared to the control; and
   (v) administering an effective amount of an agent that modulates the podocalyxin polypeptide to the animal having, or having a risk of metastatic cancer or cancer having a poor outcome;
   wherein the agent that modulates the podocalyxin polypeptide is a podocalyxin antagonist comprising an antibody that binds the podocalyxin polypeptide.

2. The method of claim 1, for inhibiting cancer metastasis.

3. The method according to claim 1, wherein the cancer is breast cancer, ovarian cancer, prostate cancer, hepatocellular cancer, hematologic malignancies, lung metastasis, osteosarcoma, melanoma, vaculogenic gliomas or glioblastoma.

4. The method according to claim 1, wherein the cancer is breast cancer.

* * * * *

SEQUENCE LISTING

```
<160> NUMBER OF SEQ ID NOS: 13

<210> SEQ ID NO 1
<211> LENGTH: 605
<212> TYPE: PRT
<213> ORGANISM: Homo sapiens

<400> SEQUENCE: 1

Met Gly Arg Leu Leu Arg Ala Ala Arg Leu Pro Pro Leu Leu Ser Pro
1               5                   10                  15

Leu Leu Leu Leu Leu Val Gly Gly Ala Phe Leu Gly Ala Cys Val Ala
            20                  25                  30

Gly Ser Asp Glu Pro Gly Pro Glu Gly Leu Thr Ser Thr Ser Leu Leu
        35                  40                  45

Asp Leu Leu Leu Pro Thr Gly Leu Glu Pro Leu Asp Ser Glu Glu Pro
    50                  55                  60

Ser Glu Thr Met Gly Leu Gly Ala Gly Leu Gly Ala Pro Gly Ser Gly
65                  70                  75                  80

Phe Pro Ser Glu Glu Asn Glu Glu Ser Arg Ile Leu Gln Pro Pro Gln
                85                  90                  95

Tyr Phe Trp Glu Glu Glu Glu Leu Asn Asp Ser Ser Leu Asp Leu
```

```
            100                 105                 110
Gly Pro Thr Ala Asp Tyr Val Phe Pro Asp Leu Thr Glu Lys Ala Gly
            115                 120                 125

Ser Ile Glu Asp Thr Ser Gln Ala Gln Glu Leu Pro Asn Leu Pro Ser
            130                 135             140

Pro Leu Pro Lys Met Asn Leu Val Glu Pro Pro Trp His Met Pro Pro
145             150                 155                 160

Arg Glu Glu Glu Glu Glu Glu Glu Glu Glu Arg Glu Lys Glu
                165                 170                 175

Glu Val Glu Lys Gln Glu Glu Glu Glu Glu Glu Leu Leu Pro Val
            180                 185                 190

Asn Gly Ser Gln Glu Glu Ala Lys Pro Gln Val Arg Asp Phe Ser Leu
            195                 200                 205

Thr Ser Ser Ser Gln Thr Pro Gly Ala Thr Lys Ser Arg His Glu Asp
            210                 215                 220

Ser Gly Asp Gln Ala Ser Ser Gly Val Glu Val Glu Ser Ser Met Gly
225                 230                 235                 240

Pro Ser Leu Leu Leu Pro Ser Val Thr Pro Thr Thr Val Thr Pro Gly
                245                 250                 255

Asp Gln Asp Ser Thr Ser Gln Glu Ala Glu Ala Thr Val Leu Pro Ala
                260                 265                 270

Ala Gly Leu Gly Val Glu Phe Glu Ala Pro Gln Glu Ala Ser Glu Glu
                275                 280                 285

Ala Thr Ala Gly Ala Ala Gly Leu Ser Gly Gln His Glu Glu Val Pro
            290                 295                 300

Ala Leu Pro Ser Phe Pro Gln Thr Thr Ala Pro Ser Gly Ala Glu His
305                 310                 315                 320

Pro Asp Glu Asp Pro Leu Gly Ser Arg Thr Ser Ala Ser Ser Pro Leu
                325                 330                 335

Ala Pro Gly Asp Met Glu Leu Thr Pro Ser Ser Ala Thr Leu Gly Gln
                340                 345                 350

Glu Asp Leu Asn Gln Gln Leu Leu Glu Gly Gln Ala Ala Glu Ala Gln
            355                 360                 365

Ser Arg Ile Pro Trp Asp Ser Thr Gln Val Ile Cys Lys Asp Trp Ser
            370                 375                 380

Asn Leu Ala Gly Lys Asn Tyr Ile Ile Leu Asn Met Thr Glu Asn Ile
385                 390                 395                 400

Asp Cys Glu Val Phe Arg Gln His Arg Gly Pro Gln Leu Leu Ala Leu
                405                 410                 415

Val Glu Glu Val Leu Pro Arg His Gly Ser His Gly Ala Trp
            420                 425                 430

His Ile Ser Leu Ser Lys Pro Ser Glu Lys Glu Gln His Leu Leu Met
            435                 440                 445

Thr Leu Val Gly Glu Gln Gly Val Val Pro Thr Gln Asp Val Leu Ser
            450                 455             460

Met Leu Gly Asp Ile Arg Arg Ser Leu Glu Glu Ile Gly Ile Gln Asn
465                 470                 475                 480

Tyr Ser Thr Thr Ser Ser Cys Gln Ala Arg Ala Ser Gln Val Arg Ser
                485                 490                 495

Asp Tyr Gly Thr Leu Phe Val Val Leu Val Val Ile Gly Ala Ile Cys
                500                 505                 510

Ile Ile Ile Ile Ala Leu Gly Leu Leu Tyr Asn Cys Trp Gln Arg Arg
            515                 520                 525
```

Leu Pro Lys Leu Lys His Val Ser His Gly Glu Glu Leu Arg Phe Val
            530                 535                 540

Glu Asn Gly Cys His Asp Asn Pro Thr Leu Asp Val Ala Ser Asp Ser
545                 550                 555                 560

Gln Ser Glu Met Gln Glu Lys His Pro Ser Leu Asn Gly Gly Gly Ala
                565                 570                 575

Leu Asn Gly Pro Gly Ser Trp Gly Ala Leu Met Gly Gly Lys Arg Asp
            580                 585                 590

Pro Glu Asp Ser Asp Val Phe Glu Glu Asp Thr His Leu
            595                 600                 605

<210> SEQ ID NO 2
<211> LENGTH: 605
<212> TYPE: PRT
<213> ORGANISM: Mus musculus

<400> SEQUENCE: 2

Met Ala Arg Pro Leu Arg Ala Ala Arg Leu Pro Pro Pro Leu Leu Leu
1               5                   10                  15

Leu Leu Ala Ala Gly Ala Ser Leu Gly Ala Tyr Ala Val Gly Val Asp
            20                  25                  30

Glu Pro Gly Pro Glu Gly Leu Thr Ser Thr Ser Leu Leu Asp Leu Leu
        35                  40                  45

Leu Pro Thr Asp Phe Glu Pro Leu Asp Ser Glu Glu Pro Ser Glu Ala
50                  55                  60

Met Gly Leu Asp Ala Gly Leu Ala Pro Gly Ser Gly Phe Pro Ser Glu
65                  70                  75                  80

Asp Ser Glu Glu Ser Arg Leu Leu Gln Pro Pro Gln Tyr Phe Trp Glu
                85                  90                  95

Glu Glu Glu Leu Asn Gly Ser Ser Leu Asp Leu Gly Pro Thr Ala Asp
            100                 105                 110

Tyr Val Phe Pro Asp Leu Thr Glu Lys Val Ala Ser Met Glu Asp Pro
        115                 120                 125

Gly Gln Ala Pro Asp Leu Pro Asn Leu Pro Ser Ile Leu Pro Lys Met
130                 135                 140

Asp Leu Ala Glu Pro Pro Trp His Met Pro Leu Gln Glu Glu Glu Glu
145                 150                 155                 160

Glu Glu Glu Glu Glu Glu Glu Arg Glu Glu Glu Arg Glu Lys
                165                 170                 175

Glu Ala Glu Glu Glu Glu Lys Gly Lys Ser Leu Leu Pro Val Asn
            180                 185                 190

Arg Val Pro Lys Glu Pro Pro Ala Gln Ala His Ala Pro Ser Pro Ser
        195                 200                 205

Thr Ser Ser Ser Thr Ser Ser Gln Ser Pro Gly Ala Thr Arg His Arg
210                 215                 220

Gln Glu Asp Ser Gly Asp Gln Ala Thr Ser Gly Met Glu Val Glu Ser
225                 230                 235                 240

Ser Val Lys Pro Thr Leu Ser Val Pro Ser Val Thr Pro Ser Thr Val
                245                 250                 255

Ala Pro Gly Val Gln Asn Tyr Ser Gln Glu Ser Gly Gly Thr Glu Trp
            260                 265                 270

Pro Thr Gly Gly Leu Gly Val Gln Ser Glu Val Pro Gln Gly Ala Gly
        275                 280                 285

Glu Gly Ala Thr Val Gly Ala Ala Asp Phe Asp Gly Gln Gln Gly Ala

```
            290                 295                 300
Leu Pro Ser Ser Leu Pro Gln Thr Val Pro Pro Ser Gly Thr Glu
305                 310                 315                 320

Val Pro Ser Glu Gly Pro Leu Tyr Pro Arg Ile Pro Asp Ser Leu Pro
                325                 330                 335

Pro Gly Pro Gln Asp Thr Glu Ser Thr Pro Ser Ser Ala Thr Trp Gly
                340                 345                 350

Gln Glu Gly Leu Ser Glu Gln Pro Leu Glu Gly Gln Ala Ala Glu Ala
                355                 360                 365

His Ser Leu Thr Pro Trp Asp Ser Thr Gln Val Ile Cys Lys Asp Trp
            370                 375                 380

Ser Asn Leu Ala Gly Lys Ser Tyr Ile Ile Leu Asn Met Thr Glu Asn
385                 390                 395                 400

Ile Asp Cys Glu Val Phe Arg Arg His Arg Gly Leu Arg Leu Leu Ala
                405                 410                 415

Leu Val Glu Glu Val Leu Pro Arg His Arg Ser Gly His Arg Gly Asp
                420                 425                 430

Trp His Ile Ser Leu Ser Lys Pro Ser Glu Lys Glu Gln His Leu Leu
            435                 440                 445

Met Thr Leu Val Gly Glu Gln Gly Val Val Pro Thr Gln Asp Val Leu
450                 455                 460

Ser Met Leu Ser Gly Ile Arg Arg Ser Leu Glu Glu Ile Gly Ile Gln
465                 470                 475                 480

Asn Tyr Ser Thr Thr Ser Ser Cys Gln Ala Arg Ala Thr Gln Val Arg
                485                 490                 495

Ser Asp Tyr Gly Thr Leu Phe Val Val Leu Val Ile Ile Gly Val Ile
                500                 505                 510

Cys Phe Ile Ile Ile Val Leu Gly Leu Leu Tyr Asn Cys Trp Gln Arg
            515                 520                 525

Arg Met Pro Lys Leu Lys His Val Ser His Gly Glu Glu Leu Arg Phe
            530                 535                 540

Val Glu Asn Gly Cys His Asp Asn Pro Thr Leu Asp Val Ala Ser Asp
545                 550                 555                 560

Ser Gln Ser Glu Met Gln Glu Lys Gln Pro Ser Leu Asn Gly Gly Ala
                565                 570                 575

Ile Asn Gly Pro Ser Ser Trp Ser Ala Leu Met Gly Ser Lys Arg Asp
                580                 585                 590

Pro Glu Asp Ser Asp Val Phe Glu Glu Asp Thr His Leu
                595                 600                 605

<210> SEQ ID NO 3
<211> LENGTH: 528
<212> TYPE: PRT
<213> ORGANISM: Homo sapiens

<400> SEQUENCE: 3

Met Arg Cys Ala Leu Ala Leu Ser Ala Leu Leu Leu Leu Leu Ser Thr
1               5                   10                  15

Pro Pro Leu Leu Pro Ser Ser Pro Ser Pro Ser Pro Ser Pro Ser Pro
                20                  25                  30

Ser Gln Asn Ala Thr Gln Thr Thr Asp Ser Ser Asn Lys Thr Ala
                35                  40                  45

Pro Thr Pro Ala Ser Ser Val Thr Ile Met Ala Thr Asp Thr Ala Gln
            50                  55                  60
```

-continued

```
Gln Ser Thr Val Pro Thr Ser Lys Ala Asn Glu Ile Leu Ala Ser Val
 65                  70                  75                  80

Lys Ala Thr Thr Leu Gly Val Ser Ser Asp Ser Pro Gly Thr Thr Thr
                 85                  90                  95

Leu Ala Gln Gln Val Ser Gly Pro Val Asn Thr Thr Val Ala Arg Gly
            100                 105                 110

Gly Gly Ser Gly Asn Pro Thr Thr Ile Glu Ser Pro Lys Ser Thr
        115                 120                 125

Lys Ser Ala Asp Thr Thr Val Ala Thr Ser Thr Ala Thr Ala Lys
    130                 135                 140

Pro Asn Thr Thr Ser Ser Gln Asn Gly Ala Glu Asp Thr Thr Asn Ser
145                 150                 155                 160

Gly Gly Lys Ser Ser His Ser Val Thr Asp Leu Thr Ser Thr Lys
                165                 170                 175

Ala Glu His Leu Thr Thr Pro His Pro Thr Ser Pro Leu Ser Pro Arg
            180                 185                 190

Gln Pro Thr Leu Thr His Pro Val Ala Thr Pro Thr Ser Ser Gly His
        195                 200                 205

Asp His Leu Met Lys Ile Ser Ser Ser Ser Thr Val Ala Ile Pro
210                 215                 220

Gly Tyr Thr Phe Thr Ser Pro Gly Met Thr Thr Thr Leu Pro Ser Ser
225                 230                 235                 240

Val Ile Ser Gln Arg Thr Gln Gln Thr Ser Ser Gln Met Pro Ala Ser
                245                 250                 255

Ser Thr Ala Pro Ser Ser Gln Glu Thr Val Gln Pro Thr Ser Pro Ala
            260                 265                 270

Thr Ala Leu Arg Thr Pro Thr Leu Pro Glu Thr Met Ser Ser Ser Pro
        275                 280                 285

Thr Ala Ala Ser Thr Thr His Arg Tyr Pro Lys Thr Pro Ser Pro Thr
        290                 295                 300

Val Ala His Glu Ser Asn Trp Ala Lys Cys Glu Asp Leu Glu Thr Gln
305                 310                 315                 320

Thr Gln Ser Glu Lys Gln Leu Val Leu Asn Leu Thr Gly Asn Thr Leu
                325                 330                 335

Cys Ala Gly Gly Ala Ser Asp Glu Lys Leu Ile Ser Leu Ile Cys Arg
            340                 345                 350

Ala Val Lys Ala Thr Phe Asn Pro Ala Gln Asp Lys Cys Gly Ile Arg
        355                 360                 365

Leu Ala Ser Val Pro Gly Ser Gln Thr Val Val Lys Glu Ile Thr
    370                 375                 380

Ile His Thr Lys Leu Pro Ala Lys Asp Val Tyr Glu Arg Leu Lys Asp
385                 390                 395                 400

Lys Trp Asp Glu Leu Lys Glu Ala Gly Val Ser Asp Met Lys Leu Gly
                405                 410                 415

Asp Gln Gly Pro Pro Glu Glu Ala Glu Asp Arg Phe Ser Met Pro Leu
            420                 425                 430

Ile Ile Thr Ile Val Cys Met Ala Ser Phe Leu Leu Leu Val Ala Ala
        435                 440                 445

Leu Tyr Gly Cys Cys His Gln Arg Leu Ser Gln Arg Lys Asp Gln Gln
    450                 455                 460

Arg Leu Thr Glu Glu Leu Gln Thr Val Glu Asn Gly Tyr His Asp Asn
465                 470                 475                 480

Pro Thr Leu Glu Val Met Glu Thr Ser Ser Glu Met Gln Glu Lys Lys
```

```
                              485                 490                 495
Val Val Ser Leu Asn Gly Glu Leu Gly Asp Ser Trp Ile Val Pro Leu
                    500                 505                 510

Asp Asn Leu Thr Lys Asp Asp Leu Asp Glu Glu Glu Asp Thr His Leu
                    515                 520                 525

<210> SEQ ID NO 4
<211> LENGTH: 503
<212> TYPE: PRT
<213> ORGANISM: Mus musculus

<400> SEQUENCE: 4

Met Pro Pro Thr Thr Ala Leu Ser Ala Leu Leu Leu Leu Leu Leu Ser
1               5                   10                  15

Pro Ala Ser His Ser His Asn Gly Asn Glu Thr Ser Thr Ser Ala Ile
                20                  25                  30

Lys Ser Ser Thr Val Gln Ser His Gln Ser Ala Thr Thr Ser Thr Glu
            35                  40                  45

Val Thr Thr Gly His Pro Val Ala Ser Thr Leu Ala Ser Thr Gln Pro
        50                  55                  60

Ser Asn Pro Thr Pro Phe Thr Thr Ser Thr Gln Ser Pro Ser Met Pro
65                  70                  75                  80

Thr Ser Thr Pro Asn Pro Thr Ser Asn Gln Ser Gly Gly Asn Leu Thr
                85                  90                  95

Ser Ser Val Ser Glu Val Asp Lys Thr Lys Thr Ser Ser Pro Ser Ser
                100                 105                 110

Thr Ala Phe Thr Ser Ser Gly Gln Thr Ala Ser Ser Gly Gly Lys
                115                 120                 125

Ser Gly Asp Ser Phe Thr Thr Ala Pro Thr Thr Leu Gly Leu Ile
            130                 135                 140

Asn Val Ser Ser Gln Pro Thr Asp Leu Asn Thr Thr Ser Lys Leu Leu
145                 150                 155                 160

Ser Thr Pro Thr Thr Asp Asn Thr Thr Ser Pro Gln Gln Pro Val Asp
                165                 170                 175

Ser Ser Pro Ser Thr Ala Ser His Pro Val Gly Gln His Thr Pro Ala
                180                 185                 190

Ala Val Pro Ser Ser Ser Gly Ser Thr Pro Ser Thr Asp Asn Ser Thr
            195                 200                 205

Leu Thr Trp Lys Pro Thr Thr His Lys Pro Leu Gly Thr Ser Glu Ala
            210                 215                 220

Thr Gln Pro Leu Thr Ser Gln Thr Pro Gly Ile Thr Thr Leu Pro Val
225                 230                 235                 240

Ser Thr Leu Gln Gln Ser Met Ala Ser Thr Val Gly Thr Thr Thr Glu
                245                 250                 255

Glu Phe Thr His Leu Ile Ser Asn Gly Thr Pro Val Ala Pro Pro Gly
                260                 265                 270

Pro Ser Thr Pro Ser Pro Ile Trp Ala Phe Gly Asn Tyr Gln Leu Asn
            275                 280                 285

Cys Glu Pro Pro Ile Arg Pro Asp Glu Glu Leu Leu Ile Leu Asn Leu
            290                 295                 300

Thr Arg Ala Ser Leu Cys Glu Arg Ser Pro Leu Asp Glu Lys Glu Lys
305                 310                 315                 320

Leu Val Glu Leu Leu Cys His Ser Val Lys Ala Ser Phe Lys Pro Ala
                325                 330                 335
```

```
Glu Asp Leu Cys Thr Leu His Val Ala Pro Ile Leu Asp Asn Gln Ala
                340                 345                 350

Val Ala Val Lys Arg Ile Ile Ile Glu Thr Lys Leu Ser Pro Lys Ala
            355                 360                 365

Val Tyr Glu Leu Leu Lys Asp Arg Trp Asp Leu Thr Glu Ala Gly
370                 375                 380

Val Ser Asp Met Lys Leu Gly Lys Glu Gly Pro Pro Glu Val Asn Glu
385                 390                 395                 400

Asp Arg Phe Ser Leu Pro Leu Ile Ile Thr Ile Val Cys Met Ala Ser
                405                 410                 415

Phe Leu Leu Leu Val Ala Ala Leu Tyr Gly Cys Cys His Gln Arg Ile
                420                 425                 430

Ser Gln Arg Lys Asp Gln Gln Arg Leu Thr Glu Glu Leu Gln Thr Val
                435                 440                 445

Glu Asn Gly Tyr His Asp Asn Pro Thr Leu Glu Val Met Glu Thr Pro
                450                 455                 460

Ser Glu Met Gln Glu Lys Lys Val Val Asn Leu Asn Gly Glu Leu Gly
465                 470                 475                 480

Asp Ser Trp Ile Val Pro Leu Asp Asn Leu Thr Lys Asp Asp Leu Asp
                485                 490                 495

Glu Glu Glu Asp Thr His Leu
                500

<210> SEQ ID NO 5
<211> LENGTH: 373
<212> TYPE: PRT
<213> ORGANISM: Homo sapiens

<400> SEQUENCE: 5

Met Pro Arg Gly Trp Thr Ala Leu Cys Leu Leu Ser Leu Leu Pro Ser
1               5                   10                  15

Gly Phe Met Ser Leu Asp Asn Asn Gly Thr Ala Thr Pro Glu Leu Pro
                20                  25                  30

Thr Gln Gly Thr Phe Ser Asn Val Ser Thr Asn Val Ser Tyr Gln Glu
            35                  40                  45

Thr Thr Thr Pro Ser Thr Leu Gly Ser Thr Ser Leu His Pro Val Ser
        50                  55                  60

Gln His Gly Asn Glu Ala Thr Thr Asn Ile Thr Glu Thr Thr Val Lys
65                  70                  75                  80

Phe Thr Ser Thr Ser Val Ile Thr Ser Val Tyr Gly Asn Thr Asn Ser
                85                  90                  95

Ser Val Gln Ser Gln Thr Ser Val Ile Ser Thr Val Phe Thr Thr Pro
                100                 105                 110

Ala Asn Val Ser Thr Pro Glu Thr Thr Leu Lys Pro Ser Leu Ser Pro
            115                 120                 125

Gly Asn Val Ser Asp Leu Ser Thr Thr Ser Thr Ser Leu Ala Thr Ser
        130                 135                 140

Pro Thr Lys Pro Tyr Thr Ser Ser Pro Ile Leu Ser Asp Ile Lys
145                 150                 155                 160

Ala Glu Ile Lys Cys Ser Gly Ile Arg Glu Val Lys Leu Thr Gln Gly
                165                 170                 175

Ile Cys Leu Glu Gln Asn Lys Thr Ser Ser Cys Ala Glu Phe Lys Lys
                180                 185                 190

Asp Arg Gly Glu Gly Leu Ala Arg Val Leu Cys Gly Glu Glu Gln Ala
                195                 200                 205
```

```
Asp Ala Asp Ala Gly Ala Gln Val Cys Ser Leu Leu Leu Ala Gln Ser
    210                 215                 220

Glu Val Arg Pro Gln Cys Leu Leu Leu Val Leu Ala Asn Arg Thr Glu
225                 230                 235                 240

Ile Ser Ser Lys Leu Gln Leu Met Lys Lys His Gln Ser Asp Leu Lys
                245                 250                 255

Lys Leu Gly Ile Leu Asp Phe Thr Glu Gln Asp Val Ala Ser His Gln
            260                 265                 270

Ser Tyr Ser Gln Lys Thr Leu Ile Ala Leu Val Thr Ser Gly Ala Leu
        275                 280                 285

Leu Ala Val Leu Gly Ile Thr Gly Tyr Phe Leu Met Asn Arg Arg Ser
    290                 295                 300

Trp Ser Pro Thr Gly Glu Arg Leu Gly Glu Asp Pro Tyr Tyr Thr Glu
305                 310                 315                 320

Asn Gly Gly Gly Gln Gly Tyr Ser Ser Gly Pro Gly Thr Ser Pro Glu
                325                 330                 335

Ala Gln Gly Lys Ala Ser Val Asn Arg Gly Ala Gln Lys Asn Gly Thr
            340                 345                 350

Gly Gln Ala Thr Ser Arg Asn Gly His Ser Ala Arg Gln His Val Val
        355                 360                 365

Ala Asp Thr Glu Leu
    370

<210> SEQ ID NO 6
<211> LENGTH: 382
<212> TYPE: PRT
<213> ORGANISM: Mus musculus

<400> SEQUENCE: 6

Met Gln Val His Arg Asp Thr Arg Ala Gly Leu Leu Leu Pro Trp Arg
1               5                   10                  15

Trp Val Ala Leu Cys Leu Met Ser Leu Leu His Leu Asn Asn Leu Thr
            20                  25                  30

Ser Ala Thr Thr Glu Thr Ser Thr Gln Gly Ile Ser Pro Ser Val Pro
        35                  40                  45

Thr Asn Glu Ser Val Glu Glu Asn Ile Thr Ser Ser Ile Pro Gly Ser
    50                  55                  60

Thr Ser His Tyr Leu Ile Tyr Gln Asp Ser Ser Lys Thr Thr Pro Ala
65              70                  75                  80

Ile Ser Glu Thr Met Val Asn Phe Thr Val Thr Ser Gly Ile Pro Ser
            85                  90                  95

Gly Ser Gly Thr Pro His Thr Phe Ser Gln Pro Gln Thr Ser Pro Thr
        100                 105                 110

Gly Ile Leu Pro Thr Thr Ser Asp Ser Ile Ser Thr Ser Glu Met Thr
    115                 120                 125

Trp Lys Ser Ser Leu Pro Ser Ile Asn Val Ser Asp Tyr Ser Pro Asn
130                 135                 140

Asn Ser Ser Phe Glu Met Thr Ser Pro Thr Glu Pro Tyr Ala Tyr Thr
145                 150                 155                 160

Ser Ser Ser Ala Pro Ser Ala Ile Lys Gly Glu Ile Lys Cys Ser Gly
            165                 170                 175

Ile Arg Glu Val Arg Leu Ala Gln Gly Ile Cys Leu Glu Leu Ser Glu
        180                 185                 190

Ala Ser Ser Cys Glu Glu Phe Lys Lys Glu Lys Gly Glu Asp Leu Ile
```

```
                195                 200                 205
Gln Ile Leu Cys Glu Lys Glu Ala Glu Ala Asp Ala Gly Ala Ser
    210                 215                 220

Val Cys Ser Leu Leu Ala Gln Ser Glu Val Arg Pro Glu Cys Leu
225                 230                 235                 240

Leu Met Val Leu Ala Asn Ser Thr Glu Leu Pro Ser Lys Leu Gln Leu
                    245                 250                 255

Met Glu Lys His Gln Ser Asp Leu Arg Lys Leu Gly Ile Gln Ser Phe
            260                 265                 270

Asn Lys Gln Asp Ile Gly Ser His Gln Ser Tyr Ser Arg Lys Thr Leu
        275                 280                 285

Ile Ala Leu Val Thr Ser Gly Val Leu Leu Ala Ile Leu Gly Thr Thr
    290                 295                 300

Gly Tyr Phe Leu Met Asn Arg Arg Ser Trp Ser Pro Thr Gly Glu Arg
305                 310                 315                 320

Leu Gly Glu Asp Pro Tyr Tyr Thr Glu Asn Gly Gly Gly Gln Gly Tyr
                325                 330                 335

Ser Ser Gly Pro Gly Ala Ser Pro Glu Thr Gln Gly Lys Ala Asn Val
            340                 345                 350

Thr Arg Gly Ala Gln Glu Asn Gly Thr Gly Gln Ala Thr Ser Arg Asn
        355                 360                 365

Gly His Ser Ala Arg Gln His Val Val Ala Asp Thr Glu Leu
    370                 375                 380

<210> SEQ ID NO 7
<211> LENGTH: 104
<212> TYPE: PRT
<213> ORGANISM: Mus musculus

<400> SEQUENCE: 7

Glu Asp Arg Phe Ser Leu Pro Leu Ile Ile Thr Ile Val Cys Met Ala
1               5                   10                  15

Ser Phe Leu Leu Leu Val Ala Ala Leu Tyr Gly Cys Cys His Gln Arg
            20                  25                  30

Ile Ser Gln Arg Lys Asp Gln Gln Arg Leu Thr Glu Glu Leu Gln Thr
        35                  40                  45

Val Glu Asn Gly Tyr His Asp Asn Pro Thr Leu Glu Val Met Glu Thr
    50                  55                  60

Pro Ser Glu Met Gln Glu Lys Lys Val Val Asn Leu Asn Gly Glu Leu
65                  70                  75                  80

Gly Asp Ser Trp Ile Val Pro Leu Asp Asn Leu Thr Lys Asp Asp Leu
                85                  90                  95

Asp Glu Glu Glu Asp Thr His Leu
            100

<210> SEQ ID NO 8
<211> LENGTH: 110
<212> TYPE: PRT
<213> ORGANISM: Mus musculus

<400> SEQUENCE: 8

Arg Ser Asp Tyr Gly Thr Leu Phe Val Val Leu Val Ile Ile Gly Val
1               5                   10                  15

Ile Cys Phe Ile Ile Ile Val Leu Gly Leu Leu Tyr Asn Cys Trp Gln
            20                  25                  30

Arg Arg Met Pro Lys Leu Lys His Val Ser His Gly Glu Glu Leu Arg
```

```
                35                  40                  45

Phe Val Glu Asn Gly Cys His Asp Asn Pro Thr Leu Asp Val Ala Ser
 50                  55                  60

Asp Ser Gln Ser Glu Met Gln Glu Lys Gln Pro Ser Leu Asn Gly Gly
 65                  70                  75                  80

Ala Ile Asn Gly Pro Ser Ser Trp Ser Ala Leu Met Gly Ser Lys Arg
                 85                  90                  95

Asp Pro Glu Asp Ser Asp Val Phe Glu Glu Asp Thr His Leu
            100                 105                 110

<210> SEQ ID NO 9
<211> LENGTH: 109
<212> TYPE: PRT
<213> ORGANISM: Mus musculus

<400> SEQUENCE: 9

Lys Gln Asp Ile Gly Ser His Gln Ser Tyr Ser Arg Lys Thr Leu Ile
 1                5                  10                  15

Ala Leu Val Thr Ser Gly Val Leu Leu Ala Ile Leu Gly Thr Thr Gly
                 20                  25                  30

Tyr Phe Leu Met Asn Arg Arg Ser Trp Ser Pro Thr Gly Glu Arg Leu
             35                  40                  45

Gly Glu Asp Pro Tyr Tyr Thr Glu Asn Gly Gly Gly Gln Gly Tyr Ser
 50                  55                  60

Ser Gly Pro Gly Ala Ser Pro Glu Thr Gln Gly Lys Ala Asn Val Thr
 65                  70                  75                  80

Arg Gly Ala Gln Glu Asn Gly Thr Gly Gln Ala Thr Ser Arg Asn Gly
                 85                  90                  95

His Ser Ala Arg Gln His Val Val Ala Asp Thr Glu Leu
            100                 105

<210> SEQ ID NO 10
<211> LENGTH: 38
<212> TYPE: PRT
<213> ORGANISM: Mus musculus

<400> SEQUENCE: 10

Val Ala Ser Met Glu Asp Pro Gly Gln Ala Pro Asp Leu Pro Asn Leu
 1                5                  10                  15

Pro Ser Ile Leu Pro Lys Met Asp Leu Ala Glu Pro Pro Trp His Met
                 20                  25                  30

Pro Leu Gln Gly Gly Cys
             35

<210> SEQ ID NO 11
<211> LENGTH: 55
<212> TYPE: DNA
<213> ORGANISM: Artificial Sequence
<220> FEATURE:
<223> OTHER INFORMATION: SHRNA coding sequence

<400> SEQUENCE: 11
tgagactggc ctatcattta ttcaagagat aaatcatagg ccagtctctt ttttc          55

<210> SEQ ID NO 12
<211> LENGTH: 55
<212> TYPE: DNA
<213> ORGANISM: Artificial Sequence
<220> FEATURE:
<223> OTHER INFORMATION: SHRNA coding sequence
```

```
<400> SEQUENCE: 12
tgtattcttg tggtataagt ttcaagagaa cttataccac aagaatactt ttttc         55

<210> SEQ ID NO 13
<211> LENGTH: 55
<212> TYPE: DNA
<213> ORGANISM: Artificial Sequence
<220> FEATURE:
<223> OTHER INFORMATION: SHRNA Coding Sequence

<400> SEQUENCE: 13
tgaatgtaaa tgtctattta ttcaagagat aaatagacat ttacattctt ttttc         55
```